(12) United States Patent
Kossmann et al.

(10) Patent No.: US 7,186,898 B1
(45) Date of Patent: Mar. 6, 2007

(54) NUCLEIC ACID MOLECULES FROM MAIZE AND THEIR USE FOR THE PRODUCTION OF MODIFIED STARCH

(75) Inventors: Jens Kossmann, Berlin (DE); Michael Emmermann, Rehbrücke (DE)

(73) Assignee: Bayer BioScience GmbH, Potsdam (DE)

( * ) Notice: Subject to any disclaimer, the term of this patent is extended or adjusted under 35 U.S.C. 154(b) by 0 days.

(21) Appl. No.: 09/334,103

(22) Filed: Jun. 16, 1999

Related U.S. Application Data

(63) Continuation of application No. PCT/EP97/07123, filed on Dec. 18, 1997.

(30) Foreign Application Priority Data

Dec. 19, 1996 (DE) ............................... 196 53 176

(51) Int. Cl.
*A01H 5/00* (2006.01)
*A01H 5/10* (2006.01)
*C12N 15/82* (2006.01)
*C12N 15/11* (2006.01)

(52) U.S. Cl. .................. 800/320.1; 536/24.5; 435/412; 435/320.1; 435/41; 435/468; 424/93.2

(58) Field of Classification Search ............... 536/23.6; 800/284, 278, 285, 298, 320.1, 320, 312, 800/300.3, 322, 300.2, 306, 310.2, 317.4; 435/410, 419, 412, 101, 69.1, 320.1, 917, 435/416, 411, 415
See application file for complete search history.

(56) References Cited

U.S. PATENT DOCUMENTS

| 5,283,184 | A | | 2/1994 | Jorgensen et al. | ....... | 435/172.3 |
| 5,824,790 | A | * | 10/1998 | Keeling et al. | ............ | 536/23.6 |

FOREIGN PATENT DOCUMENTS

| AU | 71313/96 | 9/1996 |
| WO | WO 90/12084 | 10/1990 |
| WO | WO 92/11375 | 7/1992 |
| WO | WO 94/09144 | 4/1994 |
| WO | WO 95/07355 | 3/1995 |
| WO | WO 95/26407 | 10/1995 |
| WO | WO 96/15248 | 5/1996 |
| WO | WO 97/11188 | 3/1997 |

OTHER PUBLICATIONS

Bowie, J. U. et al., "Deciphering the Message in Protein Sequences: Tolerance to Amino Acid Substitutions." 1990, Science, vol. 247, pp. 1306-1310.*
Lazar, E. et al., "Transforming Growth Factor a: Mutation of Aspartic Acid 47 and Leucine 48 Results in Different Biological Activities." 1988, Molecular and Cellular Biology, vol. 8, pp. 1247-1252.*
Broun, P. et al., "Catalytic Plasticity of Fatty Acid Modification Enzymes Underlying Chemical Diversity of Plant Lipids." 1998, Science, vol. 282, pp. 1315-1317.*
Kossmann, J. et al., "Transgenic plants as a tool to understand starch biosynthesis." 1995, Progress in Biotechnol., vol. 10, pp. 271-278.*
Sonnewald, U. et al., "A second L-type isozyme of potato glucan phosphorylase: cloning, antisense inhibition and expression analysis." 1995, Plant Molecular Biology, vol. 27, pp. 567-576.*
Kuipers et al. Formation and deposition of amylose in the potato tuber strach granule are affected by the reduction of granule-bound starch synthase gene expression vol. 6,43-52 Jan. 1994 No. 1.*
Denyer et al. Soluble isoforms of starch synthase and starch-branching enzyme also occur withi starch granules in developing pea embryos.*
Colliver et al, 1997, Plant Mol. Biol. 35:509-522.*
Hill et al, 1998, Biochem. Biophys. Res. Comm. 244:573-577.*
Yu et al, 2001, Plant Cell 13:1907-1918.*
Konecki et al., "The primary structure of human chromogranin A and pancreastatin," *J. Biol. Chem.*, 262:17026-17030 (1987).
Bansal et al., "Transient expression from *cab-m1* and *rbcS-m3* promoter sequences is different in mesophyll and bundle sheath cells in maize leaves," *Proc. Natl. Acad. Sci. USA* 89: 3654-3658, 1992.
Bolivar et al., "Construction and characterization of new cloning vehicles. II A multipurpose cloning system," *Gene* 2: 95-113, 1977.
Christensen et al., "Maize polyubiquitin genes: structure, thermal perturbation of expression and transcript splicing, and promoter activity following transfer to protoplasts by electroporation," *Pl. Molec. Biol.* 18: 675-689, 1992.
Depicker et al., "Nopaline synthase: transcript mapping and DNA sequence," *J. Molec. Appl. Genet.* 1: 561-573, 1982.
Franck et al., "Nucleotide sequence of cauliflower mosaic virus DNA," *Cell*, 21: 285-294, 1980.
Gielen et al., "The complete nucleotide sequence of the TL-DNA of the *Agrobacterium tumefaciens* plasmid pTiAch5," *EMBO J.* 3: 835-846, 1984.
Golovkin et al., "Production of transgenic maize plants by direct DNA uptake into embryogenic protoplasts," *Pl. Science* 90:41-52, 1993.
Mórocz et al., "An improved system to obtain fertile regenerants via maize protoplasts isolated from a highly embryogenic suspension culture," *Theor. Appl. Genet.* 80:721-726, 1990.
Nielsen et al., "Starch phosphorylation in potato tubers proceeds concurrently with de novo biosynthesis of starch," *Plant Physiol.* 105: 111-117, 1994.

(Continued)

*Primary Examiner*—Anne Kubelik
(74) *Attorney, Agent, or Firm*—Fish & Neave IP Group of Ropes & Gray; James F. Haley, Jr.

(57) ABSTRACT

Nucleic acid molecules are described encoding a starch granule-bound protein from maize as well as methods and recombinant DNA molecules for the production of transgenic plant cells and plants synthesizing a modified starch. Moreover, the plant cells and plants resulting from those methods as well as the starch obtainable therefrom are described.

23 Claims, 5 Drawing Sheets

OTHER PUBLICATIONS

Omirulleh et al., "Activity of a chimeric promoter with the doubled CaMV 35S enhancer element in protoplast-derived cells and transgenic plants in maize," *Pl. Molec. Biol.* 21:415-428, 1993.

Tomlinson et al., "," *Plant J.* 11: 31-43, 1997.

Yanisch-Perron et al., "Improved M13 phage cloning vectors and host strains: nucleotide sequences of the M13mp18 and pUC19 vectors," *Gene* 33:103-119, 1985.

R. Lorberth, et al., "Inhibition of a Starch-granule-bound Protein Leads to Modified Starch and Repression of Cold Sweetening," *Nature Biotechnology*, 16:473-477 (1998).

Bell et al., "A Chloroplast Lipoxygenase is Required for Wound-Induced Jasmonic Acid Accumulation in Arabidopsis," *Proc. Natl. Acad. Sci USA* 92:8675-7679 (1995).

Cheung et al., "A Floral Transmitting Tissue-Specific Glycoprotein Attracts Pollen Tubes and Stimulates Their Growth," *Cell* 82:383-393 (1995).

Elkind et al., "Abnormal Plant Development and Down-Regulation of Phenylpropanoid Biosynthesis in Transgenic Tobacco Containing a Heterologous Phenylalanine Ammonia-Lyase Gene," *Proc. Natl. Acad. Sci. USA* 87:9057-9061 (1990).

Faske et al., "Transgenic Tobacco Plants Expressing pea Chloroplast Nmdh cDNA in Sense and Antisense Orientation[1]," Plant Physiol. 115:705-715 (1997).

Goring et al., "Transformation of a Partial Nopaline Synthase Gene into Tobacco Suppresses the Expression of a Resident Wild-Type Gene," *Proc. Natl. Acad. Sci. USA* 88:1770-1774 (1991).

Smith et al., "Expression of a Truncated Tomato Polygalacturonase Gene Inhibits Expression of the Endogenous Gene in Transgenic Plants," *Mol. Gen. Genet.* 224:477-481 (1990).

Trevanion et al., "NADP-Malate Dehydrogenase in the $C_4$ Plant Flaveria bidentis," *Plant Physiol.* 113:1153-1165 (1997).

\* cited by examiner

SEQUENCE LISTING

```
<160> NUMBER OF SEQ ID NOS: 11

<210> SEQ ID NO 1
<211> LENGTH: 4856
<212> TYPE: DNA
<213> ORGANISM: Solanum tuberosum
<220> FEATURE:
<221> NAME/KEY: CDS
<222> LOCATION: (105)..(4496)

<400> SEQUENCE: 1
catcttcatc gaatttctcg aagcttcttc gctaatttcc tggtttcttc actcaaaatc        60
gacgtttcta gctgaacttg agtgaattaa gccagtggga ggat atg agt aat tcc       116
                                                Met Ser Asn Ser
                                                  1 tta ggg aat aac ttg ctg tac cag gga ttc cta acc tca aca gtg ttg        164
Leu Gly Asn Asn Leu Leu Tyr Gln Gly Phe Leu Thr Ser Thr Val Leu
  5              10                  15                  20 gaa cat aaa agt aga atc agt cct cct tgt gtt gga ggc aat tct ttg        212
Glu His Lys Ser Arg Ile Ser Pro Pro Cys Val Gly Gly Asn Ser Leu
             25                  30                  35 ttt caa caa caa gtg atc tcg aaa tca cct tta tca act gag ttt cga        260
Phe Gln Gln Gln Val Ile Ser Lys Ser Pro Leu Ser Thr Glu Phe Arg
         40                  45                  50 ggt aac agg tta aag gtg cag aaa aag aaa ata cct atg gaa aag aag        308
Gly Asn Arg Leu Lys Val Gln Lys Lys Lys Ile Pro Met Glu Lys Lys
     55                  60                  65 cgt gct ttt tct agt tct cct cat gct gta ctt acc act gat acc tct        356
Arg Ala Phe Ser Ser Ser Pro His Ala Val Leu Thr Thr Asp Thr Ser
 70                  75                  80 tct gag cta gca gaa aag ttc agt cta ggg ggg aat att gag cta cag        404
Ser Glu Leu Ala Glu Lys Phe Ser Leu Gly Gly Asn Ile Glu Leu Gln
 85                  90                  95                 100
```

```
                                                         -continued
gtt gat gtt agg cct ccc act tca ggt gat gtg tcc ttt gtg gat ttt       452
Val Asp Val Arg Pro Pro Thr Ser Gly Asp Val Ser Phe Val Asp Phe
            105                 110                 115 caa gta aca aat ggt agt gat aaa ctg ttt ttg cac tgg ggg gca gta       500
Gln Val Thr Asn Gly Ser Asp Lys Leu Phe Leu His Trp Gly Ala Val
            120                 125                 130 aaa ttc ggg aaa gaa aca tgg tct ctt ccg aat gat cgt cca gat ggg       548
Lys Phe Gly Lys Glu Thr Trp Ser Leu Pro Asn Asp Arg Pro Asp Gly
        135                 140                 145 acc aaa gtg tac aag aac aaa gca ctt aga act cca ttt gtt aaa tct       596
Thr Lys Val Tyr Lys Asn Lys Ala Leu Arg Thr Pro Phe Val Lys Ser
        150                 155                 160 ggc tct aac tcc atc ctg aga ctg gag ata cga gac act gct atc gaa       644
Gly Ser Asn Ser Ile Leu Arg Leu Glu Ile Arg Asp Thr Ala Ile Glu
165                 170                 175                 180 gct att gag ttt ctc ata tac gat gaa gcc cac gat aaa tgg ata aag       692
Ala Ile Glu Phe Leu Ile Tyr Asp Glu Ala His Asp Lys Trp Ile Lys
                185                 190                 195 aat aat ggt ggt aat ttt cgt gtc aaa ttg tca aga aaa gag ata cga       740
Asn Asn Gly Gly Asn Phe Arg Val Lys Leu Ser Arg Lys Glu Ile Arg
                200                 205                 210 ggc cca gat gtt tct gtt cct gag gag ctt gta cag atc caa tca tat       788
Gly Pro Asp Val Ser Val Pro Glu Glu Leu Val Gln Ile Gln Ser Tyr
            215                 220                 225 ttg agg tgg gag agg aag gga aaa cag aat tac ccc cct gag aaa gag       836
Leu Arg Trp Glu Arg Lys Gly Lys Gln Asn Tyr Pro Pro Glu Lys Glu
        230                 235                 240 aag gag gaa tat gag gct gct cga act gtg cta cag gag gaa ata gct       884
Lys Glu Glu Tyr Glu Ala Ala Arg Thr Val Leu Gln Glu Glu Ile Ala
245                 250                 255                 260 cgt ggt gct tcc ata cag gac att cga gca agg cta aca aaa act aat       932
Arg Gly Ala Ser Ile Gln Asp Ile Arg Ala Arg Leu Thr Lys Thr Asn
                265                 270                 275 gat aaa agt caa agc aaa gaa gag cct ctt cat gta aca aag agt gat       980
Asp Lys Ser Gln Ser Lys Glu Glu Pro Leu His Val Thr Lys Ser Asp
                280                 285                 290 ata cct gat gac ctt gcc caa gca caa gct tac att agg tgg gag aaa      1028
Ile Pro Asp Asp Leu Ala Gln Ala Gln Ala Tyr Ile Arg Trp Glu Lys
            295                 300                 305 gca gga aag ccg aac tat cct cca gaa aag caa att gaa gaa ctc gaa      1076
Ala Gly Lys Pro Asn Tyr Pro Pro Glu Lys Gln Ile Glu Glu Leu Glu
        310                 315                 320 gaa gca aga aga gaa ttg caa ctt gag ctt gag aaa ggc att acc ctt      1124
Glu Ala Arg Arg Glu Leu Gln Leu Glu Leu Glu Lys Gly Ile Thr Leu
325                 330                 335                 340 gat gag ttg cgg aaa acg att aca aaa ggg gag ata aaa act aag gtg      1172
Asp Glu Leu Arg Lys Thr Ile Thr Lys Gly Glu Ile Lys Thr Lys Val
                345                 350                 355 gaa aag cac ctg aaa aga agt tct ttt gcc gtt gaa aga atc caa aga      1220
Glu Lys His Leu Lys Arg Ser Ser Phe Ala Val Glu Arg Ile Gln Arg
                360                 365                 370 aag aag aga gac ttt ggg cat ctt att aat aag tat act tcc agt cct      1268
Lys Lys Arg Asp Phe Gly His Leu Ile Asn Lys Tyr Thr Ser Ser Pro
            375                 380                 385 gca gta caa gta caa aag gtc ttg gaa gaa cca cca gcc tta tct aaa      1316
Ala Val Gln Val Gln Lys Val Leu Glu Glu Pro Pro Ala Leu Ser Lys
        390                 395                 400 att aag ctg tat gcc aag gag aag gag gag cag att gat gat ccg atc      1364
Ile Lys Leu Tyr Ala Lys Glu Lys Glu Glu Gln Ile Asp Asp Pro Ile
405                 410                 415                 420
```

-continued

| | |
|---|---|
| cta aat aaa aag atc ttt aag gtc gat gat ggg gag cta ctg gta ctg<br>Leu Asn Lys Lys Ile Phe Lys Val Asp Asp Gly Glu Leu Leu Val Leu<br>            425                   430                   435 | 1412 |
| gta gca aag tcc tct ggg aag aca aaa gta cat cta gct aca gat ctg<br>Val Ala Lys Ser Ser Gly Lys Thr Lys Val His Leu Ala Thr Asp Leu<br>440                    445                   450 | 1460 |
| aat cag cca att act ctt cac tgg gca tta tcc aaa agt cct gga gag<br>Asn Gln Pro Ile Thr Leu His Trp Ala Leu Ser Lys Ser Pro Gly Glu<br>         455                   460                   465 | 1508 |
| tgg atg gta cca cct tca agc ata ttg cct cct ggg tca att att tta<br>Trp Met Val Pro Pro Ser Ser Ile Leu Pro Pro Gly Ser Ile Ile Leu<br>470                    475                   480 | 1556 |
| gac aag gct gcc gaa aca cct ttt tca gcc agt tct tct gat ggt cta<br>Asp Lys Ala Ala Glu Thr Pro Phe Ser Ala Ser Ser Ser Asp Gly Leu<br>485                    490                   495                   500 | 1604 |
| act tct aag gta caa tct ttg gat ata gta att gaa gat ggc aat ttt<br>Thr Ser Lys Val Gln Ser Leu Asp Ile Val Ile Glu Asp Gly Asn Phe<br>         505                   510                   515 | 1652 |
| gtg ggg atg cca ttt gtt ctt ttg tct ggt gaa aaa tgg att aag aac<br>Val Gly Met Pro Phe Val Leu Leu Ser Gly Glu Lys Trp Ile Lys Asn<br>              520                   525                   530 | 1700 |
| caa ggg tcg gat ttc tat gtt ggc ttc agt gct gca tcc aaa tta gca<br>Gln Gly Ser Asp Phe Tyr Val Gly Phe Ser Ala Ala Ser Lys Leu Ala<br>535                    540                   545 | 1748 |
| ctc aag gct gct ggg gat ggc agt gga act gca aag tct tta ctg gat<br>Leu Lys Ala Ala Gly Asp Gly Ser Gly Thr Ala Lys Ser Leu Leu Asp<br>         550                   555                   560 | 1796 |
| aaa ata gca gat atg gaa agt gag gct cag aag tca ttt atg cac cgg<br>Lys Ile Ala Asp Met Glu Ser Glu Ala Gln Lys Ser Phe Met His Arg<br>565                    570                   575                   580 | 1844 |
| ttt aat att gca gct gac ttg ata gaa gat gcc act agt gct ggt gaa<br>Phe Asn Ile Ala Ala Asp Leu Ile Glu Asp Ala Thr Ser Ala Gly Glu<br>                585                   590                   595 | 1892 |
| ctt ggt ttt gct gga att ctt gta tgg atg agg ttc atg gct aca agg<br>Leu Gly Phe Ala Gly Ile Leu Val Trp Met Arg Phe Met Ala Thr Arg<br>600                    605                   610 | 1940 |
| caa ctg ata tgg aac aaa aac tat aac gta aaa cca cgt gaa ata agc<br>Gln Leu Ile Trp Asn Lys Asn Tyr Asn Val Lys Pro Arg Glu Ile Ser<br>         615                   620                   625 | 1988 |
| aag gct cag gac aga ctt aca gac ttg ttg cag aat gct ttc acc agt<br>Lys Ala Gln Asp Arg Leu Thr Asp Leu Leu Gln Asn Ala Phe Thr Ser<br>              630                   635                   640 | 2036 |
| cac cct cag tac cgt gaa att ttg cgg atg att atg tca act gtt gga<br>His Pro Gln Tyr Arg Glu Ile Leu Arg Met Ile Met Ser Thr Val Gly<br>645                    650                   655                   660 | 2084 |
| cgt gga ggt gaa ggg gat gta gga cag cga att agg gat gaa att ttg<br>Arg Gly Gly Glu Gly Asp Val Gly Gln Arg Ile Arg Asp Glu Ile Leu<br>                665                   670                   675 | 2132 |
| gtc atc cag agg aac aat gac tgc aag ggt ggt atg atg caa gaa tgg<br>Val Ile Gln Arg Asn Asn Asp Cys Lys Gly Gly Met Met Gln Glu Trp<br>680                    685                   690 | 2180 |
| cat cag aaa ttg cat aat aat act agt cct gat gat gtt gtg atc tgt<br>His Gln Lys Leu His Asn Asn Thr Ser Pro Asp Asp Val Val Ile Cys<br>         695                   700                   705 | 2228 |
| cag gca tta att gac tac atc aag agt gat ttt gat ctt ggt gtt tat<br>Gln Ala Leu Ile Asp Tyr Ile Lys Ser Asp Phe Asp Leu Gly Val Tyr<br>710                    715                   720 | 2276 |
| tgg aaa acc ctg aat gag aac gga ata aca aaa gag cgt ctt ttg agt<br>Trp Lys Thr Leu Asn Glu Asn Gly Ile Thr Lys Glu Arg Leu Leu Ser | 2324 |

-continued

| | | | | | | | | | | | | | | |
|---|---|---|---|---|---|---|---|---|---|---|---|---|---|---|
| | 725 | | | | 730 | | | | 735 | | | | 740 | |
| tat | gac | cgt | gct | atc | cat | tct | gaa | cca | aat | ttt | aga | gga | gat caa aag | 2372 |
| Tyr | Asp | Arg | Ala | Ile | His | Ser | Glu | Pro | Asn | Phe | Arg | Gly | Asp Gln Lys | |
| | | | | 745 | | | | 750 | | | | 755 | | |
| ggt | ggt | ctt | ttg | cgt | gat | tta | ggt | cac | tat | atg | aga | aca | ttg aag gca | 2420 |
| Gly | Gly | Leu | Leu | Arg | Asp | Leu | Gly | His | Tyr | Met | Arg | Thr | Leu Lys Ala | |
| | | | 760 | | | | | 765 | | | | 770 | | |
| gtt | cat | tca | ggt | gca | gat | ctt | gag | tct | gct | att | gca | aac | tgc atg ggc | 2468 |
| Val | His | Ser | Gly | Ala | Asp | Leu | Glu | Ser | Ala | Ile | Ala | Asn | Cys Met Gly | |
| | | 775 | | | | | 780 | | | | | 785 | | |
| tac | aaa | act | gag | gga | gaa | ggc | ttt | atg | gtt | gga | gtc | cag | ata aat cct | 2516 |
| Tyr | Lys | Thr | Glu | Gly | Glu | Gly | Phe | Met | Val | Gly | Val | Gln | Ile Asn Pro | |
| | 790 | | | | | 795 | | | | | 800 | | | |
| gta | tca | ggc | ttg | cca | tct | ggc | ttt | cag | gac | ctc | ctc | cat | ttt gtc tta | 2564 |
| Val | Ser | Gly | Leu | Pro | Ser | Gly | Phe | Gln | Asp | Leu | Leu | His | Phe Val Leu | |
| 805 | | | | | 810 | | | | | 815 | | | | 820 |
| gac | cat | gtg | gaa | gat | aaa | aat | gtg | gaa | act | ctt | ctt | gag | aga ttg cta | 2612 |
| Asp | His | Val | Glu | Asp | Lys | Asn | Val | Glu | Thr | Leu | Leu | Glu | Arg Leu Leu | |
| | | | | 825 | | | | 830 | | | | 835 | | |
| gag | gct | cgt | gag | gag | ctt | agg | ccc | ttg | ctt | ctc | aaa | cca | aac aac cgt | 2660 |
| Glu | Ala | Arg | Glu | Glu | Leu | Arg | Pro | Leu | Leu | Leu | Lys | Pro | Asn Asn Arg | |
| | | | 840 | | | | | 845 | | | | 850 | | |
| cta | aag | gat | ctg | ctg | ttt | ttg | gac | ata | gca | ctt | gat | tct | aca gtt aga | 2708 |
| Leu | Lys | Asp | Leu | Leu | Phe | Leu | Asp | Ile | Ala | Leu | Asp | Ser | Thr Val Arg | |
| | | 855 | | | | | 860 | | | | | 865 | | |
| aca | gca | gta | gaa | agg | gga | tat | gaa | gaa | ttg | aac | aac | gct | aat cct gag | 2756 |
| Thr | Ala | Val | Glu | Arg | Gly | Tyr | Glu | Glu | Leu | Asn | Asn | Ala | Asn Pro Glu | |
| | 870 | | | | | 875 | | | | | 880 | | | |
| aaa | atc | atg | tac | ttc | atc | tcc | ctc | gtt | ctt | gaa | aat | ctc | gca ctc tct | 2804 |
| Lys | Ile | Met | Tyr | Phe | Ile | Ser | Leu | Val | Leu | Glu | Asn | Leu | Ala Leu Ser | |
| 885 | | | | | 890 | | | | | 895 | | | | 900 |
| gtg | gac | gat | aat | gaa | gat | ctt | gtt | tat | tgc | ttg | aag | gga | tgg aat caa | 2852 |
| Val | Asp | Asp | Asn | Glu | Asp | Leu | Val | Tyr | Cys | Leu | Lys | Gly | Trp Asn Gln | |
| | | | | 905 | | | | 910 | | | | 915 | | |
| gct | ctt | tca | atg | tcc | aat | ggt | ggg | gac | aac | cat | tgg | gct | tta ttt gca | 2900 |
| Ala | Leu | Ser | Met | Ser | Asn | Gly | Gly | Asp | Asn | His | Trp | Ala | Leu Phe Ala | |
| | | | 920 | | | | | 925 | | | | 930 | | |
| aaa | gct | gtg | ctt | gac | aga | acc | cgt | ctt | gca | ctt | gca | agc | aag gca gag | 2948 |
| Lys | Ala | Val | Leu | Asp | Arg | Thr | Arg | Leu | Ala | Leu | Ala | Ser | Lys Ala Glu | |
| | | 935 | | | | | 940 | | | | | 945 | | |
| tgg | tac | cat | cac | tta | ttg | cag | cca | tct | gcc | gaa | tat | cta | gga tca ata | 2996 |
| Trp | Tyr | His | His | Leu | Leu | Gln | Pro | Ser | Ala | Glu | Tyr | Leu | Gly Ser Ile | |
| | 950 | | | | | 955 | | | | | 960 | | | |
| ctt | ggg | gtg | gac | caa | tgg | gct | ttg | aac | ata | ttt | act | gaa | gaa att ata | 3044 |
| Leu | Gly | Val | Asp | Gln | Trp | Ala | Leu | Asn | Ile | Phe | Thr | Glu | Glu Ile Ile | |
| 965 | | | | | 970 | | | | | 975 | | | | 980 |
| cgt | gct | gga | tca | gca | gct | tca | tta | tcc | tct | ctt | ctt | aat | aga ctc gat | 3092 |
| Arg | Ala | Gly | Ser | Ala | Ala | Ser | Leu | Ser | Ser | Leu | Leu | Asn | Arg Leu Asp | |
| | | | | 985 | | | | 990 | | | | 995 | | |
| ccc | gtg | ctt | cgg | aaa | act | gca | aat | cta | gga | agt | tgg | cag | att atc agt | 3140 |
| Pro | Val | Leu | Arg | Lys | Thr | Ala | Asn | Leu | Gly | Ser | Trp | Gln | Ile Ile Ser | |
| | | | 1000 | | | | | 1005 | | | | 1010 | | |
| cca | gtt | gaa | gcc | gtt | gga | tat | gtt | gtc | gtt | gtg | gat | gag | ttg ctt tca | 3188 |
| Pro | Val | Glu | Ala | Val | Gly | Tyr | Val | Val | Val | Val | Asp | Glu | Leu Leu Ser | |
| | | | 1015 | | | | | 1020 | | | | 1025 | | |
| gtt | cag | aat | gaa | atc | tac | gag | aag | ccc | acg | atc | tta | gta | gca aaa tct | 3236 |
| Val | Gln | Asn | Glu | Ile | Tyr | Glu | Lys | Pro | Thr | Ile | Leu | Val | Ala Lys Ser | |
| | | 1030 | | | | | 1035 | | | | | 1040 | | |
| gtt | aaa | gga | gag | gag | gaa | att | cct | gat | ggt | gct | gtt | gcc | ctg ata aca | 3284 |

```
Val Lys Gly Glu Glu Ile Pro Asp Gly Ala Val Ala Leu Ile Thr
1045                1050                1055                1060 cca gac atg cca gat gtt ctt tca cat gtt tct gtt cga gct aga aat    3332
Pro Asp Met Pro Asp Val Leu Ser His Val Ser Val Arg Ala Arg Asn
                1065                1070                1075 ggg aag gtt tgc ttt gct aca tgc ttt gat ccc aat ata ttg gct gac    3380
Gly Lys Val Cys Phe Ala Thr Cys Phe Asp Pro Asn Ile Leu Ala Asp
        1080                1085                1090 ctc caa gca aag gaa gga agg att ttg ctc tta aag cct aca cct tca    3428
Leu Gln Ala Lys Glu Gly Arg Ile Leu Leu Leu Lys Pro Thr Pro Ser
        1095                1100                1105 gac ata atc tat agt gag gtg aat gag att gag ctc caa agt tca agt    3476
Asp Ile Ile Tyr Ser Glu Val Asn Glu Ile Glu Leu Gln Ser Ser Ser
    1110                1115                1120 aac ttg gta gaa gct gaa act tca gca aca ctt aga ttg gtg aaa aag    3524
Asn Leu Val Glu Ala Glu Thr Ser Ala Thr Leu Arg Leu Val Lys Lys
1125                1130                1135                1140 caa ttt ggt ggt tgt tac gca ata tca gca gat gaa ttc aca agt gaa    3572
Gln Phe Gly Gly Cys Tyr Ala Ile Ser Ala Asp Glu Phe Thr Ser Glu
                1145                1150                1155 atg gtt gga gct aaa tca cgt aat att gca tat ctg aaa gga aaa gtg    3620
Met Val Gly Ala Lys Ser Arg Asn Ile Ala Tyr Leu Lys Gly Lys Val
        1160                1165                1170 cct tcc tcg gtg gga att cct acg tca gta gct ctt cca ttt gga gtc    3668
Pro Ser Ser Val Gly Ile Pro Thr Ser Val Ala Leu Pro Phe Gly Val
        1175                1180                1185 ttt gag aaa gta ctt tca gac gac ata aat cag gga gtg gca aaa gag    3716
Phe Glu Lys Val Leu Ser Asp Asp Ile Asn Gln Gly Val Ala Lys Glu
    1190                1195                1200 ttg caa att ctg atg aaa aaa cta tct gaa gga gac ttc agc gct ctt    3764
Leu Gln Ile Leu Met Lys Lys Leu Ser Glu Gly Asp Phe Ser Ala Leu
1205                1210                1215                1220 ggt gaa att cgc aca acg gtt tta gat ctt tca gca cca gct caa ttg    3812
Gly Glu Ile Arg Thr Thr Val Leu Asp Leu Ser Ala Pro Ala Gln Leu
                1225                1230                1235 gtc aaa gag ctg aag gag aag atg cag ggt tct ggc atg cct tgg cct    3860
Val Lys Glu Leu Lys Glu Lys Met Gln Gly Ser Gly Met Pro Trp Pro
        1240                1245                1250 ggt gat gaa ggt cca aag cgg tgg gaa caa gca tgg atg gcc ata aaa    3908
Gly Asp Glu Gly Pro Lys Arg Trp Glu Gln Ala Trp Met Ala Ile Lys
        1255                1260                1265 aag gtg tgg gct tca aaa tgg aat gag aga gca tac ttc agc aca agg    3956
Lys Val Trp Ala Ser Lys Trp Asn Glu Arg Ala Tyr Phe Ser Thr Arg
    1270                1275                1280 aag gtg aaa ctg gat cat gac tat ctg tgc atg gct gtc ctt gtt caa    4004
Lys Val Lys Leu Asp His Asp Tyr Leu Cys Met Ala Val Leu Val Gln
1285                1290                1295                1300 gaa ata ata aat gct gat tat gca ttt gtc att cac aca acc aac cca    4052
Glu Ile Ile Asn Ala Asp Tyr Ala Phe Val Ile His Thr Thr Asn Pro
                1305                1310                1315 tct tcc gga gac gac tca gaa ata tat gcc gag gtg gtc agg ggc ctt    4100
Ser Ser Gly Asp Asp Ser Glu Ile Tyr Ala Glu Val Val Arg Gly Leu
        1320                1325                1330 ggg gaa aca ctt gtt gga gct tat cca gga cgt gct ttg agt ttt atc    4148
Gly Glu Thr Leu Val Gly Ala Tyr Pro Gly Arg Ala Leu Ser Phe Ile
        1335                1340                1345 tgc aag aaa aag gat ctc aac tct cct caa gtg tta ggt tac cca agc    4196
Cys Lys Lys Lys Asp Leu Asn Ser Pro Gln Val Leu Gly Tyr Pro Ser
    1350                1355                1360
```

```
aaa ccg atc ggc ctt ttc ata aaa aga tct atc atc ttc cga tct gat      4244
Lys Pro Ile Gly Leu Phe Ile Lys Arg Ser Ile Ile Phe Arg Ser Asp
1365                1370                1375                1380 tcc aat ggg gaa gat ttg gaa ggt tat gcc ggt gct ggc ctc tac gac      4292
Ser Asn Gly Glu Asp Leu Glu Gly Tyr Ala Gly Ala Gly Leu Tyr Asp
            1385                1390                1395 agt gta cca atg gat gag gag gaa aaa gtt gta att gat tac tct tcc      4340
Ser Val Pro Met Asp Glu Glu Glu Lys Val Val Ile Asp Tyr Ser Ser
1400                1405                1410 gac cca ttg ata act gat ggt aac ttc cgc cag aca atc ctg tcc aac      4388
Asp Pro Leu Ile Thr Asp Gly Asn Phe Arg Gln Thr Ile Leu Ser Asn
        1415                1420                1425 att gct cgt gct gga cat gct atc gag gag cta tat ggc tct cct caa      4436
Ile Ala Arg Ala Gly His Ala Ile Glu Glu Leu Tyr Gly Ser Pro Gln
    1430                1435                1440 gac att gag ggt gta gtg agg gat gga aag att tat gtc gtt cag aca      4484
Asp Ile Glu Gly Val Val Arg Asp Gly Lys Ile Tyr Val Val Gln Thr
1445                1450                1455                1460 aga cca cag atg tgattatatt ctcgttgtat gttgttcaga aagaccaca           4536
Arg Pro Gln Met gatgtgatca tattctcatt gtatcagatc tgtgaccact tacctgatac ctcccatgaa    4596
gttacctgta tgattatacg tgatccaaag ccatcacatc atgttcacct tcagctattg    4656
gaggagaagt gagaagtagg aattgcaata tgaggaataa taagaaaaac tttgtaaaag    4716
ctaaattagc tgggtatgat ataggggagaa atgtgtaaac attgtactat atatagtata   4776
tacacacgca ttatgtattg cattatgcac tgaataatat cgcagcatca aagaagaaat   4836
cctttgggtg gtttcaaaaa                                                 4856

<210> SEQ ID NO 2
<211> LENGTH: 1464
<212> TYPE: PRT
<213> ORGANISM: Solanum tuberosum

<400> SEQUENCE: 2

Met Ser Asn Ser Leu Gly Asn Asn Leu Leu Tyr Gln Gly Phe Leu Thr
1               5                   10                  15

Ser Thr Val Leu Glu His Lys Ser Arg Ile Ser Pro Pro Cys Val Gly
            20                  25                  30

Gly Asn Ser Leu Phe Gln Gln Gln Val Ile Ser Lys Ser Pro Leu Ser
        35                  40                  45

Thr Glu Phe Arg Gly Asn Arg Leu Lys Val Gln Lys Lys Lys Ile Pro
    50                  55                  60

Met Glu Lys Lys Arg Ala Phe Ser Ser Pro His Ala Val Leu Thr
65                  70                  75                  80

Thr Asp Thr Ser Ser Glu Leu Ala Glu Lys Phe Ser Leu Gly Gly Asn
                85                  90                  95

Ile Glu Leu Gln Val Asp Val Arg Pro Pro Thr Ser Gly Asp Val Ser
            100                 105                 110

Phe Val Asp Phe Gln Val Thr Asn Gly Ser Asp Lys Leu Phe Leu His
        115                 120                 125

Trp Gly Ala Val Lys Phe Gly Lys Glu Thr Trp Ser Leu Pro Asn Asp
    130                 135                 140

Arg Pro Asp Gly Thr Lys Val Tyr Lys Asn Lys Ala Leu Arg Thr Pro
145                 150                 155                 160

Phe Val Lys Ser Gly Ser Asn Ser Ile Leu Arg Leu Glu Ile Arg Asp
                165                 170                 175
```

-continued

```
Thr Ala Ile Glu Ala Ile Glu Phe Leu Ile Tyr Asp Glu Ala His Asp
            180                 185                 190
Lys Trp Ile Lys Asn Asn Gly Gly Asn Phe Arg Val Lys Leu Ser Arg
        195                 200                 205
Lys Glu Ile Arg Gly Pro Asp Val Ser Val Pro Glu Glu Leu Val Gln
    210                 215                 220
Ile Gln Ser Tyr Leu Arg Trp Glu Arg Lys Gly Lys Gln Asn Tyr Pro
225                 230                 235                 240
Pro Glu Lys Glu Lys Glu Glu Tyr Glu Ala Ala Arg Thr Val Leu Gln
                245                 250                 255
Glu Glu Ile Ala Arg Gly Ala Ser Ile Gln Asp Ile Arg Ala Arg Leu
            260                 265                 270
Thr Lys Thr Asn Asp Lys Ser Gln Ser Lys Glu Glu Pro Leu His Val
        275                 280                 285
Thr Lys Ser Asp Ile Pro Asp Asp Leu Ala Gln Ala Gln Ala Tyr Ile
    290                 295                 300
Arg Trp Glu Lys Ala Gly Lys Pro Asn Tyr Pro Pro Glu Lys Gln Ile
305                 310                 315                 320
Glu Glu Leu Glu Glu Ala Arg Arg Glu Leu Gln Leu Glu Leu Glu Lys
                325                 330                 335
Gly Ile Thr Leu Asp Glu Leu Arg Lys Thr Ile Thr Lys Gly Glu Ile
            340                 345                 350
Lys Thr Lys Val Glu Lys His Leu Lys Arg Ser Ser Phe Ala Val Glu
        355                 360                 365
Arg Ile Gln Arg Lys Lys Arg Asp Phe Gly His Leu Ile Asn Lys Tyr
    370                 375                 380
Thr Ser Ser Pro Ala Val Gln Val Gln Lys Val Leu Glu Glu Pro Pro
385                 390                 395                 400
Ala Leu Ser Lys Ile Lys Leu Tyr Ala Lys Glu Lys Glu Glu Gln Ile
                405                 410                 415
Asp Asp Pro Ile Leu Asn Lys Lys Ile Phe Lys Val Asp Asp Gly Glu
            420                 425                 430
Leu Leu Val Leu Val Ala Lys Ser Gly Lys Thr Lys Val His Leu
        435                 440                 445
Ala Thr Asp Leu Asn Gln Pro Ile Thr Leu His Trp Ala Leu Ser Lys
    450                 455                 460
Ser Pro Gly Glu Trp Met Val Pro Pro Ser Ser Ile Leu Pro Pro Gly
465                 470                 475                 480
Ser Ile Ile Leu Asp Lys Ala Ala Glu Thr Pro Phe Ser Ala Ser Ser
                485                 490                 495
Ser Asp Gly Leu Thr Ser Lys Val Gln Ser Leu Asp Ile Val Ile Glu
            500                 505                 510
Asp Gly Asn Phe Val Gly Met Pro Phe Val Leu Leu Ser Gly Glu Lys
        515                 520                 525
Trp Ile Lys Asn Gln Gly Ser Asp Phe Tyr Val Gly Phe Ser Ala Ala
    530                 535                 540
Ser Lys Leu Ala Leu Lys Ala Ala Gly Asp Gly Ser Gly Thr Ala Lys
545                 550                 555                 560
Ser Leu Leu Asp Lys Ile Ala Asp Met Glu Ser Glu Ala Gln Lys Ser
                565                 570                 575
Phe Met His Arg Phe Asn Ile Ala Ala Asp Leu Ile Glu Asp Ala Thr
            580                 585                 590
```

-continued

```
Ser Ala Gly Glu Leu Gly Phe Ala Gly Ile Leu Val Trp Met Arg Phe
        595                 600                 605

Met Ala Thr Arg Gln Leu Ile Trp Asn Lys Asn Tyr Asn Val Lys Pro
        610                 615                 620

Arg Glu Ile Ser Lys Ala Gln Asp Arg Leu Thr Asp Leu Leu Gln Asn
625                 630                 635                 640

Ala Phe Thr Ser His Pro Gln Tyr Arg Glu Ile Leu Arg Met Ile Met
                645                 650                 655

Ser Thr Val Gly Arg Gly Gly Glu Gly Asp Val Gly Gln Arg Ile Arg
                660                 665                 670

Asp Glu Ile Leu Val Ile Gln Arg Asn Asn Asp Cys Lys Gly Gly Met
        675                 680                 685

Met Gln Glu Trp His Gln Lys Leu His Asn Asn Thr Ser Pro Asp Asp
        690                 695                 700

Val Val Ile Cys Gln Ala Leu Ile Asp Tyr Ile Lys Ser Asp Phe Asp
705                 710                 715                 720

Leu Gly Val Tyr Trp Lys Thr Leu Asn Glu Asn Gly Ile Thr Lys Glu
                725                 730                 735

Arg Leu Leu Ser Tyr Asp Arg Ala Ile His Ser Glu Pro Asn Phe Arg
                740                 745                 750

Gly Asp Gln Lys Gly Gly Leu Leu Arg Asp Leu Gly His Tyr Met Arg
        755                 760                 765

Thr Leu Lys Ala Val His Ser Gly Ala Asp Leu Glu Ser Ala Ile Ala
770                 775                 780

Asn Cys Met Gly Tyr Lys Thr Glu Gly Glu Gly Phe Met Val Gly Val
785                 790                 795                 800

Gln Ile Asn Pro Val Ser Gly Leu Pro Ser Gly Phe Gln Asp Leu Leu
                805                 810                 815

His Phe Val Leu Asp His Val Glu Asp Lys Asn Val Glu Thr Leu Leu
                820                 825                 830

Glu Arg Leu Leu Glu Ala Arg Glu Glu Leu Arg Pro Leu Leu Leu Lys
        835                 840                 845

Pro Asn Asn Arg Leu Lys Asp Leu Leu Phe Leu Asp Ile Ala Leu Asp
        850                 855                 860

Ser Thr Val Arg Thr Ala Val Glu Arg Gly Tyr Glu Glu Leu Asn Asn
865                 870                 875                 880

Ala Asn Pro Glu Lys Ile Met Tyr Phe Ile Ser Leu Val Leu Glu Asn
                885                 890                 895

Leu Ala Leu Ser Val Asp Asp Asn Glu Asp Leu Val Tyr Cys Leu Lys
                900                 905                 910

Gly Trp Asn Gln Ala Leu Ser Met Ser Asn Gly Gly Asp Asn His Trp
        915                 920                 925

Ala Leu Phe Ala Lys Ala Val Leu Asp Arg Thr Arg Leu Ala Leu Ala
        930                 935                 940

Ser Lys Ala Glu Trp Tyr His His Leu Leu Gln Pro Ser Ala Glu Tyr
945                 950                 955                 960

Leu Gly Ser Ile Leu Gly Val Asp Gln Trp Ala Leu Asn Ile Phe Thr
                965                 970                 975

Glu Glu Ile Ile Arg Ala Gly Ser Ala Ser Leu Ser Ser Leu Leu
                980                 985                 990

Asn Arg Leu Asp Pro Val Leu Arg Lys Thr Ala Asn Leu Gly Ser Trp
        995                1000                1005

Gln Ile Ile Ser Pro Val Glu Ala Val Gly Tyr Val Val Val Val Asp
```

-continued

```
                1010                1015                1020
Glu Leu Leu Ser Val Gln Asn Glu Ile Tyr Glu Lys Pro Thr Ile Leu
1025                1030                1035                1040

Val Ala Lys Ser Val Lys Gly Glu Glu Ile Pro Asp Gly Ala Val
            1045                1050                1055

Ala Leu Ile Thr Pro Asp Met Pro Asp Val Leu Ser His Val Ser Val
            1060                1065                1070

Arg Ala Arg Asn Gly Lys Val Cys Phe Ala Thr Cys Phe Asp Pro Asn
        1075                1080                1085

Ile Leu Ala Asp Leu Gln Ala Lys Glu Gly Arg Ile Leu Leu Leu Lys
    1090                1095                1100

Pro Thr Pro Ser Asp Ile Ile Tyr Ser Glu Val Asn Glu Ile Glu Leu
1105                1110                1115                1120

Gln Ser Ser Ser Asn Leu Val Glu Ala Glu Thr Ser Ala Thr Leu Arg
            1125                1130                1135

Leu Val Lys Lys Gln Phe Gly Gly Cys Tyr Ala Ile Ser Ala Asp Glu
            1140                1145                1150

Phe Thr Ser Glu Met Val Gly Ala Lys Ser Arg Asn Ile Ala Tyr Leu
        1155                1160                1165

Lys Gly Lys Val Pro Ser Ser Val Gly Ile Pro Thr Ser Val Ala Leu
    1170                1175                1180

Pro Phe Gly Val Phe Glu Lys Val Leu Ser Asp Asp Ile Asn Gln Gly
1185                1190                1195                1200

Val Ala Lys Glu Leu Gln Ile Leu Met Lys Lys Leu Ser Glu Gly Asp
            1205                1210                1215

Phe Ser Ala Leu Gly Glu Ile Arg Thr Thr Val Leu Asp Leu Ser Ala
            1220                1225                1230

Pro Ala Gln Leu Val Lys Glu Leu Lys Glu Lys Met Gln Gly Ser Gly
        1235                1240                1245

Met Pro Trp Pro Gly Asp Glu Gly Pro Lys Arg Trp Glu Gln Ala Trp
    1250                1255                1260

Met Ala Ile Lys Lys Val Trp Ala Ser Lys Trp Asn Glu Arg Ala Tyr
1265                1270                1275                1280

Phe Ser Thr Arg Lys Val Lys Leu Asp His Asp Tyr Leu Cys Met Ala
            1285                1290                1295

Val Leu Val Gln Glu Ile Ile Asn Ala Asp Tyr Ala Phe Val Ile His
            1300                1305                1310

Thr Thr Asn Pro Ser Ser Gly Asp Asp Ser Glu Ile Tyr Ala Glu Val
        1315                1320                1325

Val Arg Gly Leu Gly Glu Thr Leu Val Gly Ala Tyr Pro Gly Arg Ala
    1330                1335                1340

Leu Ser Phe Ile Cys Lys Lys Lys Asp Leu Asn Ser Pro Gln Val Leu
1345                1350                1355                1360

Gly Tyr Pro Ser Lys Pro Ile Gly Leu Phe Ile Lys Arg Ser Ile Ile
            1365                1370                1375

Phe Arg Ser Asp Ser Asn Gly Glu Asp Leu Glu Gly Tyr Ala Gly Ala
            1380                1385                1390

Gly Leu Tyr Asp Ser Val Pro Met Asp Glu Glu Glu Lys Val Val Ile
        1395                1400                1405

Asp Tyr Ser Ser Asp Pro Leu Ile Thr Asp Gly Asn Phe Arg Gln Thr
    1410                1415                1420

Ile Leu Ser Asn Ile Ala Arg Ala Gly His Ala Ile Glu Glu Leu Tyr
1425                1430                1435                1440
```

Gly Ser Pro Gln Asp Ile Glu Gly Val Val Arg Asp Gly Lys Ile Tyr
                1445               1450                1455

Val Val Gln Thr Arg Pro Gln Met
            1460

<210> SEQ ID NO 3
<211> LENGTH: 1918
<212> TYPE: DNA
<213> ORGANISM: Solanum tuberosum
<220> FEATURE:
<221> NAME/KEY: CDS
<222> LOCATION: (1)..(1554)

<400> SEQUENCE: 3

| | | |
|---|---|---|
| gca gag tgg tac cat cac tta ttg cag cca tct gcc gaa tat cta gga<br>Ala Glu Trp Tyr His His Leu Leu Gln Pro Ser Ala Glu Tyr Leu Gly<br>1               5                   10                  15 | | 48 |
| tca ata ctt ggg gtg gac caa tgg gct ttg aac ata ttt act gaa gaa<br>Ser Ile Leu Gly Val Asp Gln Trp Ala Leu Asn Ile Phe Thr Glu Glu<br>        20                  25                  30 | | 96 |
| att ata cgt gct gga tca gca gct tca tta tcc tct ctt ctt aat aga<br>Ile Ile Arg Ala Gly Ser Ala Ala Ser Leu Ser Ser Leu Leu Asn Arg<br>    35                  40                  45 | | 144 |
| ctc gat ccc gtg ctt cgg aaa act gca aat cta gga agt tgg cag att<br>Leu Asp Pro Val Leu Arg Lys Thr Ala Asn Leu Gly Ser Trp Gln Ile<br>50                  55                  60 | | 192 |
| atc agt cca gtt gaa gcc gtt gga tat gtt gtc gtt gtg gat gag ttg<br>Ile Ser Pro Val Glu Ala Val Gly Tyr Val Val Val Val Asp Glu Leu<br>65                  70                  75                  80 | | 240 |
| ctt tca gtt cag aat gaa atc tac gag aag ccc acg atc tta gta gca<br>Leu Ser Val Gln Asn Glu Ile Tyr Glu Lys Pro Thr Ile Leu Val Ala<br>                85                  90                  95 | | 288 |
| aaa tct gtt aaa gga gag gag gaa att cct gat ggt gct gtt gcc ctg<br>Lys Ser Val Lys Gly Glu Glu Glu Ile Pro Asp Gly Ala Val Ala Leu<br>        100                 105                 110 | | 336 |
| ata aca cca gac atg cca gat gtt ctt tca cat gtt tct gtt cga gct<br>Ile Thr Pro Asp Met Pro Asp Val Leu Ser His Val Ser Val Arg Ala<br>    115                 120                 125 | | 384 |
| aga aat ggg aag gtt tgc ttt gct aca tgc ttt gat ccc aat ata ttg<br>Arg Asn Gly Lys Val Cys Phe Ala Thr Cys Phe Asp Pro Asn Ile Leu<br>130                 135                 140 | | 432 |
| gct gac ctc caa gca aag gaa gga agg att ttg ctc tta aag cct aca<br>Ala Asp Leu Gln Ala Lys Glu Gly Arg Ile Leu Leu Leu Lys Pro Thr<br>145                 150                 155                 160 | | 480 |
| cct tca gac ata atc tat agt gag gtg aat gag att gag ctc caa agt<br>Pro Ser Asp Ile Ile Tyr Ser Glu Val Asn Glu Ile Glu Leu Gln Ser<br>                165                 170                 175 | | 528 |
| tca agt aac ttg gta gaa gct gaa act tca gca aca ctt aga ttg gtg<br>Ser Ser Asn Leu Val Glu Ala Glu Thr Ser Ala Thr Leu Arg Leu Val<br>        180                 185                 190 | | 576 |
| aaa aag caa ttt ggt ggt tgt tac gca ata tca gca gat gaa ttc aca<br>Lys Lys Gln Phe Gly Gly Cys Tyr Ala Ile Ser Ala Asp Glu Phe Thr<br>    195                 200                 205 | | 624 |
| agt gaa atg gtt gga gct aaa tca cgt aat att gca tat ctg aaa gga<br>Ser Glu Met Val Gly Ala Lys Ser Arg Asn Ile Ala Tyr Leu Lys Gly<br>210                 215                 220 | | 672 |
| aaa gtg cct tcc tcg gtg gga att cct acg tca gta gct ctt cca ttt<br>Lys Val Pro Ser Ser Val Gly Ile Pro Thr Ser Val Ala Leu Pro Phe<br>225                 230                 235                 240 | | 720 |
| gga gtc ttt gag aaa gta ctt tca gac gac ata aat cag gga gtg gca | | 768 |

```
Gly Val Phe Glu Lys Val Leu Ser Asp Asp Ile Asn Gln Gly Val Ala
                245                 250                 255 aaa gag ttg caa att ctg aca aaa aaa cta tct gaa gga gac ttt agc      816
Lys Glu Leu Gln Ile Leu Thr Lys Lys Leu Ser Glu Gly Asp Phe Ser
            260                 265                 270 gct ctt ggt gaa att cgc aca acg gtt tta gat ctt tcg aca cca gct      864
Ala Leu Gly Glu Ile Arg Thr Thr Val Leu Asp Leu Ser Thr Pro Ala
        275                 280                 285 caa ttg gtc aaa gag ctg aag gag aag atg cag ggt tct ggc atg cct      912
Gln Leu Val Lys Glu Leu Lys Glu Lys Met Gln Gly Ser Gly Met Pro
    290                 295                 300 tgg cct ggt gat gaa ggt cca aag cgg tgg gaa caa gca tgg atg gcc      960
Trp Pro Gly Asp Glu Gly Pro Lys Arg Trp Glu Gln Ala Trp Met Ala
305                 310                 315                 320 ata aaa aag gtg tgg gct tca aaa tgg aat gag aga gca tac ttc agc     1008
Ile Lys Lys Val Trp Ala Ser Lys Trp Asn Glu Arg Ala Tyr Phe Ser
                325                 330                 335 aca agg aag gtg aaa ctg gat cat gac tat ctg tgc atg gct gtc ctt     1056
Thr Arg Lys Val Lys Leu Asp His Asp Tyr Leu Cys Met Ala Val Leu
            340                 345                 350 gtt caa gaa ata ata aat gct gat tat gca ttt gtc att cac aca acc     1104
Val Gln Glu Ile Ile Asn Ala Asp Tyr Ala Phe Val Ile His Thr Thr
        355                 360                 365 aac cca tct tcc gga gac gac tca gaa ata tat gcc gag gtg gtc agg     1152
Asn Pro Ser Ser Gly Asp Asp Ser Glu Ile Tyr Ala Glu Val Val Arg
    370                 375                 380 ggc ctt ggg gaa aca ctt gtt gga gct tat cca gga cgt gct ttg agt     1200
Gly Leu Gly Glu Thr Leu Val Gly Ala Tyr Pro Gly Arg Ala Leu Ser
385                 390                 395                 400 ttt atc tgc aag aaa aag gat ctc aac tct cct caa gtg tta ggt tac     1248
Phe Ile Cys Lys Lys Lys Asp Leu Asn Ser Pro Gln Val Leu Gly Tyr
                405                 410                 415 cca agc aaa ccg atc ggc ctt ttc ata aaa aga tct atc atc ttc cga     1296
Pro Ser Lys Pro Ile Gly Leu Phe Ile Lys Arg Ser Ile Ile Phe Arg
            420                 425                 430 tct gat tcc aat ggg gaa gat ttg gaa ggt tat gcc ggt gct ggc ctc     1344
Ser Asp Ser Asn Gly Glu Asp Leu Glu Gly Tyr Ala Gly Ala Gly Leu
        435                 440                 445 tac gac agt gta cca atg gat gag gag gaa aaa gtt gta att gat tac     1392
Tyr Asp Ser Val Pro Met Asp Glu Glu Glu Lys Val Val Ile Asp Tyr
    450                 455                 460 tct tcc gac cca ttg ata act gat ggt aac ttc cgc cag aca atc ctg     1440
Ser Ser Asp Pro Leu Ile Thr Asp Gly Asn Phe Arg Gln Thr Ile Leu
465                 470                 475                 480 tcc aac att gct cgt gct gga cat gct atc gag gag cta tat ggc tct     1488
Ser Asn Ile Ala Arg Ala Gly His Ala Ile Glu Glu Leu Tyr Gly Ser
                485                 490                 495 cct caa gac att gag ggt gta gtg agg gat gga aag att tat gtc gtt     1536
Pro Gln Asp Ile Glu Gly Val Val Arg Asp Gly Lys Ile Tyr Val Val
            500                 505                 510 cag aca aga cca cag atg tgattatatt ctcgttgtat gttgttcaga            1584
Gln Thr Arg Pro Gln Met
        515 gaagaccaca gatgtgatca tattctcatt gtatcagatc tgtgaccact tacctgatac   1644 ctcccatgaa gttacctgta tgattatacg tgatccaaag ccatcacatc atgttcacct   1704 tcagctattg gaggagaagt gagaagtagg aattgcaata tgaggaataa taagaaaaac   1764 tttgtaaaag ctaaattagc tgggtatgat ataggggaga atgtgtaaac attgtactat   1824
```

```
atatagtata tacacacgca ttatgtattg cattatgcac tgaataatat cgcagcatca    1884
aagaagaaat cctttgggtg gtttcaaaaa aaaa                                1918

<210> SEQ ID NO 4
<211> LENGTH: 518
<212> TYPE: PRT
<213> ORGANISM: Solanum tuberosum

<400> SEQUENCE: 4

Ala Glu Trp Tyr His His Leu Leu Gln Pro Ser Ala Glu Tyr Leu Gly
  1               5                  10                  15

Ser Ile Leu Gly Val Asp Gln Trp Ala Leu Asn Ile Phe Thr Glu Glu
                 20                  25                  30

Ile Ile Arg Ala Gly Ser Ala Ala Ser Leu Ser Ser Leu Leu Asn Arg
             35                  40                  45

Leu Asp Pro Val Leu Arg Lys Thr Ala Asn Leu Gly Ser Trp Gln Ile
         50                  55                  60

Ile Ser Pro Val Glu Ala Val Gly Tyr Val Val Val Asp Glu Leu
 65                  70                  75                  80

Leu Ser Val Gln Asn Glu Ile Tyr Glu Lys Pro Thr Ile Leu Val Ala
                 85                  90                  95

Lys Ser Val Lys Gly Glu Glu Ile Pro Asp Gly Ala Val Ala Leu
            100                 105                 110

Ile Thr Pro Asp Met Pro Asp Val Leu Ser His Val Ser Val Arg Ala
        115                 120                 125

Arg Asn Gly Lys Val Cys Phe Ala Thr Cys Phe Asp Pro Asn Ile Leu
130                 135                 140

Ala Asp Leu Gln Ala Lys Glu Gly Arg Ile Leu Leu Leu Lys Pro Thr
145                 150                 155                 160

Pro Ser Asp Ile Ile Tyr Ser Glu Val Asn Glu Ile Glu Leu Gln Ser
                165                 170                 175

Ser Ser Asn Leu Val Glu Ala Glu Thr Ser Ala Thr Leu Arg Leu Val
            180                 185                 190

Lys Lys Gln Phe Gly Gly Cys Tyr Ala Ile Ser Ala Asp Glu Phe Thr
        195                 200                 205

Ser Glu Met Val Gly Ala Lys Ser Arg Asn Ile Ala Tyr Leu Lys Gly
    210                 215                 220

Lys Val Pro Ser Ser Val Gly Ile Pro Thr Ser Val Ala Leu Pro Phe
225                 230                 235                 240

Gly Val Phe Glu Lys Val Leu Ser Asp Ile Asn Gln Gly Val Ala
                245                 250                 255

Lys Glu Leu Gln Ile Leu Thr Lys Leu Ser Glu Gly Asp Phe Ser
            260                 265                 270

Ala Leu Gly Glu Ile Arg Thr Thr Val Leu Asp Leu Ser Thr Pro Ala
        275                 280                 285

Gln Leu Val Lys Glu Leu Lys Glu Lys Met Gln Gly Ser Gly Met Pro
    290                 295                 300

Trp Pro Gly Asp Glu Gly Pro Lys Arg Trp Glu Gln Ala Trp Met Ala
305                 310                 315                 320

Ile Lys Lys Val Trp Ala Ser Lys Trp Asn Glu Arg Ala Tyr Phe Ser
                325                 330                 335

Thr Arg Lys Val Lys Leu Asp His Asp Tyr Leu Cys Met Ala Val Leu
            340                 345                 350

Val Gln Glu Ile Ile Asn Ala Asp Tyr Ala Phe Val Ile His Thr Thr
```

```
                    355              360                365
Asn Pro Ser Ser Gly Asp Asp Ser Glu Ile Tyr Ala Glu Val Val Arg
    370                 375                380

Gly Leu Gly Glu Thr Leu Val Gly Ala Tyr Pro Gly Arg Ala Leu Ser
385                 390                 395                400

Phe Ile Cys Lys Lys Lys Asp Leu Asn Ser Pro Gln Val Leu Gly Tyr
                405                 410                415

Pro Ser Lys Pro Ile Gly Leu Phe Ile Lys Arg Ser Ile Ile Phe Arg
                420                 425                 430

Ser Asp Ser Asn Gly Glu Asp Leu Glu Gly Tyr Ala Gly Ala Gly Leu
                435                 440                 445

Tyr Asp Ser Val Pro Met Asp Glu Glu Glu Lys Val Val Ile Asp Tyr
450                 455                 460

Ser Ser Asp Pro Leu Ile Thr Asp Gly Asn Phe Arg Gln Thr Ile Leu
465                 470                 475                480

Ser Asn Ile Ala Arg Ala Gly His Ala Ile Glu Glu Leu Tyr Gly Ser
                485                 490                 495

Pro Gln Asp Ile Glu Gly Val Val Arg Asp Gly Lys Ile Tyr Val Val
                500                 505                 510

Gln Thr Arg Pro Gln Met
            515

<210> SEQ ID NO 5
<211> LENGTH: 2307
<212> TYPE: DNA
<213> ORGANISM: Zea Mays
<220> FEATURE:
<221> NAME/KEY: CDS
<222> LOCATION: (33)..(1943)

<400> SEQUENCE: 5
tagtggatcc ccccgggctg cagggaattc gg cac gag ctt gag ggg cta ttg          53
                                   His Glu Leu Glu Gly Leu Leu
                                     1               5 gaa gct cga gtt gaa ctg cgc cct ttg ctt ctt gat tcg cgt gaa cgc        101
Glu Ala Arg Val Glu Leu Arg Pro Leu Leu Leu Asp Ser Arg Glu Arg
         10                  15                  20 atg aaa gat ctt ata ttt ttg gac att gct ctt gat tct acc ttc agg        149
Met Lys Asp Leu Ile Phe Leu Asp Ile Ala Leu Asp Ser Thr Phe Arg
 25                  30                  35 aca gca att gaa agg tca tat gag gag ctg aat gat gca gcc cca gag        197
Thr Ala Ile Glu Arg Ser Tyr Glu Glu Leu Asn Asp Ala Ala Pro Glu
 40                  45                  50                  55 aaa ata atg tac ttc atc agt ctt gtc ctt gaa aat ctt gcg ctt tca        245
Lys Ile Met Tyr Phe Ile Ser Leu Val Leu Glu Asn Leu Ala Leu Ser
                 60                  65                  70 att gac gac aat gaa gac atc ctg tat tgt tta aag gga tgg aac caa        293
Ile Asp Asp Asn Glu Asp Ile Leu Tyr Cys Leu Lys Gly Trp Asn Gln
             75                  80                  85 gcc ttg gaa atg gct aag caa aaa gac gac caa tgg gcg ctc tat gct        341
Ala Leu Glu Met Ala Lys Gln Lys Asp Asp Gln Trp Ala Leu Tyr Ala
         90                  95                 100 aaa gca ttt ctt gac aga aac aga ctt gcc ctt gcg agc aag gga gaa        389
Lys Ala Phe Leu Asp Arg Asn Arg Leu Ala Leu Ala Ser Lys Gly Glu
    105                 110                 115 caa tac cat aat atg atg cag ccc tct gct gag tat ctt ggc tcg tta        437
Gln Tyr His Asn Met Met Gln Pro Ser Ala Glu Tyr Leu Gly Ser Leu
120                 125                 130                 135
```

```
ctc agc ata gac caa tgg gca gtc aat atc ttc aca gaa gaa att ata      485
Leu Ser Ile Asp Gln Trp Ala Val Asn Ile Phe Thr Glu Glu Ile Ile
            140                 145                 150 cgc ggt gga tca gct gct act ctg tct gct ctt ctg aac cga ttt gat      533
Arg Gly Gly Ser Ala Ala Thr Leu Ser Ala Leu Leu Asn Arg Phe Asp
        155                 160                 165 cct gtt tta agg aat gtt gct cac ctc gga agt tgg cag gtt ata agc      581
Pro Val Leu Arg Asn Val Ala His Leu Gly Ser Trp Gln Val Ile Ser
        170                 175                 180 ccg gtt gaa gta tca ggt tat gtg gtt gtg gtt gat gag tta ctt gct      629
Pro Val Glu Val Ser Gly Tyr Val Val Val Val Asp Glu Leu Leu Ala
    185                 190                 195 gtc cag aac aaa tct tat gat aaa cca acc atc ctt gtg gca aag agt      677
Val Gln Asn Lys Ser Tyr Asp Lys Pro Thr Ile Leu Val Ala Lys Ser
200                 205                 210                 215 gtc aag gga gag gaa gaa ata cca gat gga gta gtt ggt gta att aca      725
Val Lys Gly Glu Glu Glu Ile Pro Asp Gly Val Val Gly Val Ile Thr
                220                 225                 230 cct gat atg cca gat gtt ctg tct cat gtg tca gtc cga gca agg aat      773
Pro Asp Met Pro Asp Val Leu Ser His Val Ser Val Arg Ala Arg Asn
            235                 240                 245 agc aag gta ctg ttt gcg acc tgt ttt gac cac acc act cta tct gaa      821
Ser Lys Val Leu Phe Ala Thr Cys Phe Asp His Thr Thr Leu Ser Glu
        250                 255                 260 ctt gaa gga tat gat cag aaa ctg ttt tcc ttc aag cct act tct gca      869
Leu Glu Gly Tyr Asp Gln Lys Leu Phe Ser Phe Lys Pro Thr Ser Ala
        265                 270                 275 gat ata acc tat agg gag atc aca gag agt gaa ctt cag caa tca agt      917
Asp Ile Thr Tyr Arg Glu Ile Thr Glu Ser Glu Leu Gln Gln Ser Ser
280                 285                 290                 295 tct cca aat gca gaa gtt ggc cat gca gta cca tct att tca ttg gcc      965
Ser Pro Asn Ala Glu Val Gly His Ala Val Pro Ser Ile Ser Leu Ala
                300                 305                 310 aag aag aaa ttt ctt gga aaa tat gca ata tca gcc gaa gaa ttc tct     1013
Lys Lys Lys Phe Leu Gly Lys Tyr Ala Ile Ser Ala Glu Glu Phe Ser
            315                 320                 325 gag gaa atg gtt ggg gcc aag tct cgg aat ata gca tac ctc aaa gga     1061
Glu Glu Met Val Gly Ala Lys Ser Arg Asn Ile Ala Tyr Leu Lys Gly
        330                 335                 340 aaa gta cct tca tgg gtc ggt gtc cca acg tca gtt gcg ata cca ttt     1109
Lys Val Pro Ser Trp Val Gly Val Pro Thr Ser Val Ala Ile Pro Phe
        345                 350                 355 ggc act ttt gag aag gtt ttg tca gat ggg ctt aat aag gaa gta gca     1157
Gly Thr Phe Glu Lys Val Leu Ser Asp Gly Leu Asn Lys Glu Val Ala
360                 365                 370                 375 cag agc ata gag aag ctt aag atc aga ctt gcc caa gaa gat ttt agt     1205
Gln Ser Ile Glu Lys Leu Lys Ile Arg Leu Ala Gln Glu Asp Phe Ser
                380                 385                 390 gct cta ggt gaa ata aga aaa gtc gtc ctt aat ctt act gct cct atg     1253
Ala Leu Gly Glu Ile Arg Lys Val Val Leu Asn Leu Thr Ala Pro Met
            395                 400                 405 caa ttg gtt aat gag ctg aag gag agg atg cta ggc tct gga atg ccc     1301
Gln Leu Val Asn Glu Leu Lys Glu Arg Met Leu Gly Ser Gly Met Pro
        410                 415                 420 tgg cct ggt gat gaa gga gac aag cgt tgg gag caa gca tgg atg gct     1349
Trp Pro Gly Asp Glu Gly Asp Lys Arg Trp Glu Gln Ala Trp Met Ala
        425                 430                 435 att aaa aag gtt tgg gca tca aaa tgg aac gaa aga gca tat ttt agc     1397
Ile Lys Lys Val Trp Ala Ser Lys Trp Asn Glu Arg Ala Tyr Phe Ser
440                 445                 450                 455
```

-continued

```
aca cgc aag gtg aaa ctt gat cat gag tac ctt tcg atg gct gtt ctc      1445
Thr Arg Lys Val Lys Leu Asp His Glu Tyr Leu Ser Met Ala Val Leu
                460                 465                 470 gtg caa gaa gtt gtg aat gca gat tat gct ttt gtc att cat acc aca      1493
Val Gln Glu Val Val Asn Ala Asp Tyr Ala Phe Val Ile His Thr Thr
            475                 480                 485 aac cca tcg tct gga gat tct tct gag ata tat gct gaa gtg gtg aaa      1541
Asn Pro Ser Ser Gly Asp Ser Ser Glu Ile Tyr Ala Glu Val Val Lys
        490                 495                 500 ggg ctt ggc gag acc ctc gtg gga gcc tat cct ggt cgt gct atg agc      1589
Gly Leu Gly Glu Thr Leu Val Gly Ala Tyr Pro Gly Arg Ala Met Ser
    505                 510                 515 ttt gtt tgc aaa aaa gat gac ctt gac tct ccc aag tta ctt ggt tac      1637
Phe Val Cys Lys Lys Asp Asp Leu Asp Ser Pro Lys Leu Leu Gly Tyr
520                 525                 530                 535 cca agc aag cca att ggt ctc ttc ata agg caa tca atc atc ttc cgt      1685
Pro Ser Lys Pro Ile Gly Leu Phe Ile Arg Gln Ser Ile Ile Phe Arg
                540                 545                 550 tcc gac tcc aac ggt gag gac ctg gaa ggt tat gct gga gca gga tta      1733
Ser Asp Ser Asn Gly Glu Asp Leu Glu Gly Tyr Ala Gly Ala Gly Leu
            555                 560                 565 tat gat agt gta ccg atg gat gag gag gat gag gtt gta ctt gat tat      1781
Tyr Asp Ser Val Pro Met Asp Glu Glu Asp Glu Val Val Leu Asp Tyr
        570                 575                 580 aca act gac cct ctt ata gta gac cgt gga ttc cga agc tca atc ctc      1829
Thr Thr Asp Pro Leu Ile Val Asp Arg Gly Phe Arg Ser Ser Ile Leu
    585                 590                 595 tca agc ata gca cgg gct ggc cat gcc atc gag gag cta tat ggt tct      1877
Ser Ser Ile Ala Arg Ala Gly His Ala Ile Glu Glu Leu Tyr Gly Ser
600                 605                 610                 615 cct cag gac gtc gag gga gta gtg aag gat gga aaa atc tat gta gtc      1925
Pro Gln Asp Val Glu Gly Val Val Lys Asp Gly Lys Ile Tyr Val Val
                620                 625                 630 cag aca aga cca cag atg tagtatgtat gcatctatta gacagctcaa             1973
Gln Thr Arg Pro Gln Met
                635 taagcactgt tgtacgcttg tatggttggg acatatgggc gttatggcat gtatagttgt    2033 atgcctagat gtacaacacg tgtactcgta tatatatata taaatgctga aacaagcatt    2093 ggtcctgtac tgtagtttct acatttcatt gtcaccaata attaagtgta ctcctatggc    2153 tgggagtcta tgaaaatgga cgtgttgact tattgggtaa taaataattt atatataaaa    2213 aaaaaaaaaa aaaaaaaaaa aaaaaaaaaa aaaaaaaaaa aaaaaaaaaa ctcgaggggg    2273 ggccggtccc aattcgccta tagtgagtcg tata                                2307

<210> SEQ ID NO 6
<211> LENGTH: 637
<212> TYPE: PRT
<213> ORGANISM: Zea Mays

<400> SEQUENCE: 6

His Glu Leu Glu Gly Leu Leu Glu Ala Arg Val Glu Leu Arg Pro Leu
  1               5                  10                  15

Leu Leu Asp Ser Arg Glu Arg Met Lys Asp Leu Ile Phe Leu Asp Ile
             20                  25                  30

Ala Leu Asp Ser Thr Phe Arg Thr Ala Ile Glu Arg Ser Tyr Glu Glu
         35                  40                  45

Leu Asn Asp Ala Ala Pro Glu Lys Ile Met Tyr Phe Ile Ser Leu Val
```

```
            50                  55                  60
Leu Glu Asn Leu Ala Leu Ser Ile Asp Asp Asn Glu Asp Ile Leu Tyr
 65                  70                  75                  80

Cys Leu Lys Gly Trp Asn Gln Ala Leu Glu Met Ala Lys Gln Lys Asp
                 85                  90                  95

Asp Gln Trp Ala Leu Tyr Ala Lys Ala Phe Leu Asp Arg Asn Arg Leu
            100                 105                 110

Ala Leu Ala Ser Lys Gly Glu Gln Tyr His Asn Met Met Gln Pro Ser
            115                 120                 125

Ala Glu Tyr Leu Gly Ser Leu Leu Ser Ile Asp Gln Trp Ala Val Asn
            130                 135                 140

Ile Phe Thr Glu Glu Ile Ile Arg Gly Gly Ser Ala Ala Thr Leu Ser
145                 150                 155                 160

Ala Leu Leu Asn Arg Phe Asp Pro Val Leu Arg Asn Val Ala His Leu
                165                 170                 175

Gly Ser Trp Gln Val Ile Ser Pro Glu Val Ser Gly Tyr Val Val
                180                 185                 190

Val Val Asp Glu Leu Leu Ala Val Gln Asn Lys Ser Tyr Asp Lys Pro
                195                 200                 205

Thr Ile Leu Val Ala Lys Ser Val Lys Gly Glu Glu Ile Pro Asp
            210                 215                 220

Gly Val Gly Val Ile Thr Pro Asp Met Pro Asp Val Leu Ser His
225                 230                 235                 240

Val Ser Val Arg Ala Arg Asn Ser Lys Val Leu Phe Ala Thr Cys Phe
                245                 250                 255

Asp His Thr Thr Leu Ser Glu Leu Glu Gly Tyr Asp Gln Lys Leu Phe
                260                 265                 270

Ser Phe Lys Pro Thr Ser Ala Asp Ile Thr Tyr Arg Glu Ile Thr Glu
            275                 280                 285

Ser Glu Leu Gln Gln Ser Ser Pro Asn Ala Glu Val Gly His Ala
            290                 295                 300

Val Pro Ser Ile Ser Leu Ala Lys Lys Phe Leu Gly Lys Tyr Ala
305                 310                 315                 320

Ile Ser Ala Glu Glu Phe Ser Glu Met Val Gly Ala Lys Ser Arg
                325                 330                 335

Asn Ile Ala Tyr Leu Lys Gly Lys Val Pro Ser Trp Val Gly Val Pro
            340                 345                 350

Thr Ser Val Ala Ile Pro Phe Gly Thr Phe Glu Lys Val Leu Ser Asp
            355                 360                 365

Gly Leu Asn Lys Glu Val Ala Gln Ser Ile Glu Lys Leu Lys Ile Arg
370                 375                 380

Leu Ala Gln Glu Asp Phe Ser Ala Leu Gly Glu Ile Arg Lys Val Val
385                 390                 395                 400

Leu Asn Leu Thr Ala Pro Met Gln Leu Val Asn Glu Leu Lys Glu Arg
                405                 410                 415

Met Leu Gly Ser Gly Met Pro Trp Pro Gly Asp Glu Gly Asp Lys Arg
                420                 425                 430

Trp Glu Gln Ala Trp Met Ala Ile Lys Lys Val Trp Ala Ser Lys Trp
                435                 440                 445

Asn Glu Arg Ala Tyr Phe Ser Thr Arg Lys Val Lys Leu Asp His Glu
            450                 455                 460

Tyr Leu Ser Met Ala Val Leu Val Gln Glu Val Val Asn Ala Asp Tyr
465                 470                 475                 480
```

```
Ala Phe Val Ile His Thr Thr Asn Pro Ser Ser Gly Asp Ser Ser Glu
                485                 490                 495

Ile Tyr Ala Glu Val Val Lys Gly Leu Gly Glu Thr Leu Val Gly Ala
            500                 505                 510

Tyr Pro Gly Arg Ala Met Ser Phe Val Cys Lys Lys Asp Asp Leu Asp
        515                 520                 525

Ser Pro Lys Leu Leu Gly Tyr Pro Ser Lys Pro Ile Gly Leu Phe Ile
    530                 535                 540

Arg Gln Ser Ile Ile Phe Arg Ser Asp Ser Asn Gly Glu Asp Leu Glu
545                 550                 555                 560

Gly Tyr Ala Gly Ala Gly Leu Tyr Asp Ser Val Pro Met Asp Glu Glu
                565                 570                 575

Asp Glu Val Val Leu Asp Tyr Thr Thr Asp Pro Leu Ile Val Asp Arg
            580                 585                 590

Gly Phe Arg Ser Ser Ile Leu Ser Ser Ile Ala Arg Ala Gly His Ala
        595                 600                 605

Ile Glu Glu Leu Tyr Gly Ser Pro Gln Asp Val Glu Gly Val Val Lys
    610                 615                 620

Asp Gly Lys Ile Tyr Val Val Gln Thr Arg Pro Gln Met
625                 630                 635

<210> SEQ ID NO 7
<211> LENGTH: 4329
<212> TYPE: DNA
<213> ORGANISM: Zea Mays
<220> FEATURE:
<221> NAME/KEY: CDS
<222> LOCATION: (2)..(4009)

<400> SEQUENCE: 7 c cca gat ggc acg aca gtg tac aag aac agg gct ctc agg aca cct ttt      49
  Pro Asp Gly Thr Thr Val Tyr Lys Asn Arg Ala Leu Arg Thr Pro Phe
    1               5                  10                  15 gta aag tca ggt gat aac tcc act cta agg att gag ata gat gat cct      97
Val Lys Ser Gly Asp Asn Ser Thr Leu Arg Ile Glu Ile Asp Asp Pro
             20                  25                  30 ggg gtg cac gcc att gag ttc ctc atc ttt gac gag aca cag aac aaa     145
Gly Val His Ala Ile Glu Phe Leu Ile Phe Asp Glu Thr Gln Asn Lys
         35                  40                  45 tgg ttt aaa aac aat ggc cag aat ttt cag gtt cag ttc cag tcg agc     193
Trp Phe Lys Asn Asn Gly Gln Asn Phe Gln Val Gln Phe Gln Ser Ser
     50                  55                  60 cgc cat cag ggt act ggt gca tct ggt gcc tcc tct tct gct act tct     241
Arg His Gln Gly Thr Gly Ala Ser Gly Ala Ser Ser Ser Ala Thr Ser
 65                  70                  75                  80 acc ttg gtg cca gag gat ctt gtg cag atc caa gct tac ctt cgg tgg     289
Thr Leu Val Pro Glu Asp Leu Val Gln Ile Gln Ala Tyr Leu Arg Trp
                 85                  90                  95 gaa aga agg gga aag cag tca tac aca cca gag caa gaa aag gag gag     337
Glu Arg Arg Gly Lys Gln Ser Tyr Thr Pro Glu Gln Glu Lys Glu Glu
            100                 105                 110 tat gaa gct gca cga gct gag tta ata gag gaa gta aac aga ggt gtt     385
Tyr Glu Ala Ala Arg Ala Glu Leu Ile Glu Glu Val Asn Arg Gly Val
        115                 120                 125 tct tta gag aag ctt cga gct aaa ttg aca aaa gca cct gaa gca ccc     433
Ser Leu Glu Lys Leu Arg Ala Lys Leu Thr Lys Ala Pro Glu Ala Pro
    130                 135                 140 gag tcg gat gaa agt aaa tct tct gca tct cga gtg ccc atc ggt aaa     481
Glu Ser Asp Glu Ser Lys Ser Ser Ala Ser Arg Val Pro Ile Gly Lys
```

-continued

| | | | | | | | | | | | | | | | |
|---|---|---|---|---|---|---|---|---|---|---|---|---|---|---|---|
| Glu | Ser | Asp | Glu | Ser | Lys | Ser | Ser | Ala | Ser | Arg | Val | Pro | Ile | Gly | Lys |
| 145 | | | | 150 | | | | | 155 | | | | | 160 | | ctt cca gag gat ctt gta cag gtg cag gct tat ata agg tgg gag caa    529
Leu Pro Glu Asp Leu Val Gln Val Gln Ala Tyr Ile Arg Trp Glu Gln
            165              170              175 gcg ggc aaa cca aac tat cct cct gag aag caa ctg gta gaa ttt gag    577
Ala Gly Lys Pro Asn Tyr Pro Pro Glu Lys Gln Leu Val Glu Phe Glu
        180              185              190 gaa gca agg aag gaa ctg cag gct gag gtg gac aag gga atc tct att    625
Glu Ala Arg Lys Glu Leu Gln Ala Glu Val Asp Lys Gly Ile Ser Ile
    195              200              205 gat cag ttg agg cag aaa att ttg aaa gga aac att gag agt aaa gtt    673
Asp Gln Leu Arg Gln Lys Ile Leu Lys Gly Asn Ile Glu Ser Lys Val
210              215              220 tcc aag cag ctg aag aac aag aag tac ttc tct gta gaa agg att cag    721
Ser Lys Gln Leu Lys Asn Lys Lys Tyr Phe Ser Val Glu Arg Ile Gln
225              230              235              240 cgc aaa aag aga gat atc aca caa ctt ctc agt aaa cat aag cat aca    769
Arg Lys Lys Arg Asp Ile Thr Gln Leu Leu Ser Lys His Lys His Thr
                245              250              255 gtt atg gaa gat aaa gta gag gtt gta cca aaa caa cca act gtt ctt    817
Val Met Glu Asp Lys Val Glu Val Val Pro Lys Gln Pro Thr Val Leu
            260              265              270 gat ctc ttc acc aag tct tta cat gag aag gat ggc tgt gaa gtt cta    865
Asp Leu Phe Thr Lys Ser Leu His Glu Lys Asp Gly Cys Glu Val Leu
        275              280              285 agc aga aag ctc ttc aag ttc ggc gat aaa gag ata ctg gca att tct    913
Ser Arg Lys Leu Phe Lys Phe Gly Asp Lys Glu Ile Leu Ala Ile Ser
    290              295              300 acc aag gtt caa aat aaa aca gaa gtt cac ttg gca aca aac cat acg    961
Thr Lys Val Gln Asn Lys Thr Glu Val His Leu Ala Thr Asn His Thr
305              310              315              320 gac cca ctt att ctt cac tgg tct ttg gca aaa aat gct gga gaa tgg    1009
Asp Pro Leu Ile Leu His Trp Ser Leu Ala Lys Asn Ala Gly Glu Trp
                325              330              335 aag gca cct tct cca aat ata ttg cca tct ggt tcc aca ttg ctg gac    1057
Lys Ala Pro Ser Pro Asn Ile Leu Pro Ser Gly Ser Thr Leu Leu Asp
            340              345              350 aag gcg tgt gaa act gaa ttt act aaa tct gaa ttg gat ggt ttg cat    1105
Lys Ala Cys Glu Thr Glu Phe Thr Lys Ser Glu Leu Asp Gly Leu His
        355              360              365 tac cag gtt gtt gag ata gag ctt gat gac gga gga tac aaa gga atg    1153
Tyr Gln Val Val Glu Ile Glu Leu Asp Asp Gly Gly Tyr Lys Gly Met
    370              375              380 cca ttt gtt ctt cgg tct ggt gaa aca tgg ata aaa aat aat ggt tct    1201
Pro Phe Val Leu Arg Ser Gly Glu Thr Trp Ile Lys Asn Asn Gly Ser
385              390              395              400 gat ttt ttc cta gat ttc agc acc cat gat gtc aga aat att aag gca    1249
Asp Phe Phe Leu Asp Phe Ser Thr His Asp Val Arg Asn Ile Lys Ala
                405              410              415 att tta aag gac aat ggc gat gct ggt aaa ggt act tct aag gcg ttg    1297
Ile Leu Lys Asp Asn Gly Asp Ala Gly Lys Gly Thr Ser Lys Ala Leu
            420              425              430 ctg gag aga ata gca gat ctg gag gaa gat gcc cag cga tct ctt atg    1345
Leu Glu Arg Ile Ala Asp Leu Glu Glu Asp Ala Gln Arg Ser Leu Met
        435              440              445 cac aga ttc aat att gca gca gat cta gct gac caa gcc aga gat gct    1393
His Arg Phe Asn Ile Ala Ala Asp Leu Ala Asp Gln Ala Arg Asp Ala
    450              455              460

```
gga ctt ttg ggt att gtt ggg ctt ttt gtt tgg att aga ttc atg gct    1441
Gly Leu Leu Gly Ile Val Gly Leu Phe Val Trp Ile Arg Phe Met Ala
465             470                 475                 480 acc agg caa cta aca tgg aat aag aac tat aat gtg aag cca cgt gag    1489
Thr Arg Gln Leu Thr Trp Asn Lys Asn Tyr Asn Val Lys Pro Arg Glu
                485                 490                 495 ata agc aaa gca cag gat agg ttt aca gat gat ctt gag aat atg tac    1537
Ile Ser Lys Ala Gln Asp Arg Phe Thr Asp Asp Leu Glu Asn Met Tyr
            500                 505                 510 aaa act tat cca cag tac aga gag ata tta aga atg ata atg gct gct    1585
Lys Thr Tyr Pro Gln Tyr Arg Glu Ile Leu Arg Met Ile Met Ala Ala
        515                 520                 525 gtt ggt cgc gga ggt gaa ggt gat gtt ggt caa cgc att cgt gat gag    1633
Val Gly Arg Gly Gly Glu Gly Asp Val Gly Gln Arg Ile Arg Asp Glu
    530                 535                 540 ata tta gta ata cag aga aat aat gac tgc aaa ggt gga atg atg gaa    1681
Ile Leu Val Ile Gln Arg Asn Asn Asp Cys Lys Gly Gly Met Met Glu
545             550                 555                 560 gaa tgg cac cag aaa ttg cac aac aat aca agc cca gat gat gta gtg    1729
Glu Trp His Gln Lys Leu His Asn Asn Thr Ser Pro Asp Asp Val Val
                565                 570                 575 ata tgc cag gcc tta att gat tat atc aag agt gac ttt gat ata agc    1777
Ile Cys Gln Ala Leu Ile Asp Tyr Ile Lys Ser Asp Phe Asp Ile Ser
            580                 585                 590 gtt tac tgg gac acc ttg aac aaa aat ggc ata acc aaa gag cgt ctc    1825
Val Tyr Trp Asp Thr Leu Asn Lys Asn Gly Ile Thr Lys Glu Arg Leu
        595                 600                 605 ttg agc tat gat cgt gct att cat tca gaa cca aat ttc aga agt gaa    1873
Leu Ser Tyr Asp Arg Ala Ile His Ser Glu Pro Asn Phe Arg Ser Glu
    610                 615                 620 cag aag gcg ggt tta ctc cgt gac ctg gga aat tac atg aga agc cta    1921
Gln Lys Ala Gly Leu Leu Arg Asp Leu Gly Asn Tyr Met Arg Ser Leu
625             630                 635                 640 aag gct gtg cat tct ggt gct gat ctt gaa tct gct ata gca agt tgt    1969
Lys Ala Val His Ser Gly Ala Asp Leu Glu Ser Ala Ile Ala Ser Cys
                645                 650                 655 atg gga tac aaa tca gag ggt gaa ggt ttc atg gtt ggt gtt cag atc    2017
Met Gly Tyr Lys Ser Glu Gly Glu Gly Phe Met Val Gly Val Gln Ile
            660                 665                 670 aat cca gtg aag ggt tta cca tct gga ttt ccg gag ttg ctt gaa ttt    2065
Asn Pro Val Lys Gly Leu Pro Ser Gly Phe Pro Glu Leu Leu Glu Phe
        675                 680                 685 gtg ctt gaa cat gtt gag gat aaa tca gcg gaa cca ctt cct gag ggg    2113
Val Leu Glu His Val Glu Asp Lys Ser Ala Glu Pro Leu Pro Glu Gly
    690                 695                 700 cta ttg gaa gct cga gtt gaa ctg cgc cct ttg ctt ctt gat tcg cgt    2161
Leu Leu Glu Ala Arg Val Glu Leu Arg Pro Leu Leu Leu Asp Ser Arg
705             710                 715                 720 gaa cgc atg aaa gat ctt ata ttt ttg gac att gct ctt gat tct acc    2209
Glu Arg Met Lys Asp Leu Ile Phe Leu Asp Ile Ala Leu Asp Ser Thr
                725                 730                 735 ttc agg aca gca att gaa agg tca tat gag gag ctg aat gat gca gcc    2257
Phe Arg Thr Ala Ile Glu Arg Ser Tyr Glu Glu Leu Asn Asp Ala Ala
            740                 745                 750 cca gag aaa ata atg tac ttc atc agt ctt gtc ctt gaa aat ctt gcg    2305
Pro Glu Lys Ile Met Tyr Phe Ile Ser Leu Val Leu Glu Asn Leu Ala
        755                 760                 765 ctt tca att gac gac aat gaa gac atc ctg tat tgt tta aag gga tgg    2353
Leu Ser Ile Asp Asp Asn Glu Asp Ile Leu Tyr Cys Leu Lys Gly Trp
    770                 775                 780
```

```
                                              -continued aac caa gcc ttg gaa atg gct aag caa aaa gac gac caa tgg gcg ctc      2401
Asn Gln Ala Leu Glu Met Ala Lys Gln Lys Asp Asp Gln Trp Ala Leu
785                 790                 795                 800 tat gct aaa gca ttt ctt gac aga aac aga ctt gcc ctt gcg agc aag      2449
Tyr Ala Lys Ala Phe Leu Asp Arg Asn Arg Leu Ala Leu Ala Ser Lys
                805                 810                 815 gga gaa caa tac cat aat atg atg cag ccc tct gct gag tat ctt ggc      2497
Gly Glu Gln Tyr His Asn Met Met Gln Pro Ser Ala Glu Tyr Leu Gly
            820                 825                 830 tcg tta ctc agc ata gac caa tgg gca gtc aat atc ttc aca gaa gaa      2545
Ser Leu Leu Ser Ile Asp Gln Trp Ala Val Asn Ile Phe Thr Glu Glu
        835                 840                 845 att ata cgc ggt gga tca gct gct act ctg tct gct ctt ctg aac cga      2593
Ile Ile Arg Gly Gly Ser Ala Ala Thr Leu Ser Ala Leu Leu Asn Arg
    850                 855                 860 ttt gat cct gtt tta agg aat gtt gct cac ctc gga agt tgg cag gtt      2641
Phe Asp Pro Val Leu Arg Asn Val Ala His Leu Gly Ser Trp Gln Val
865                 870                 875                 880 ata agc ccg gtt gaa gta tca ggt tat gtg gtt gtg gtt gat gag tta      2689
Ile Ser Pro Val Glu Val Ser Gly Tyr Val Val Val Val Asp Glu Leu
                885                 890                 895 ctt gct gtc cag aac aaa tct tat gat aaa cca acc atc ctt gtg gca      2737
Leu Ala Val Gln Asn Lys Ser Tyr Asp Lys Pro Thr Ile Leu Val Ala
            900                 905                 910 aag agt gtc aag gga gag gaa gaa ata cca gat gga gta gtt ggt gta      2785
Lys Ser Val Lys Gly Glu Glu Glu Ile Pro Asp Gly Val Val Gly Val
        915                 920                 925 att aca cct gat atg cca gat gtt ctg tct cat gtg tca gtc cga gca      2833
Ile Thr Pro Asp Met Pro Asp Val Leu Ser His Val Ser Val Arg Ala
    930                 935                 940 agg aat agc aag gta ctg ttt gcg acc tgt ttt gac cac acc act cta      2881
Arg Asn Ser Lys Val Leu Phe Ala Thr Cys Phe Asp His Thr Thr Leu
945                 950                 955                 960 tct gaa ctt gaa gga tat gat cag aaa ctg ttt tcc ttc aag cct act      2929
Ser Glu Leu Glu Gly Tyr Asp Gln Lys Leu Phe Ser Phe Lys Pro Thr
                965                 970                 975 tct gca gat ata acc tat agg gag atc aca gag agt gaa ctt cag caa      2977
Ser Ala Asp Ile Thr Tyr Arg Glu Ile Thr Glu Ser Glu Leu Gln Gln
            980                 985                 990 tca agt tct cca aat gca gaa gtt ggc cat gca gta cca tct att tca      3025
Ser Ser Ser Pro Asn Ala Glu Val Gly His Ala Val Pro Ser Ile Ser
        995                 1000                1005 ttg gcc aag aag aaa ttt ctt gga aaa tat gca ata tca gcc gaa gaa      3073
Leu Ala Lys Lys Lys Phe Leu Gly Lys Tyr Ala Ile Ser Ala Glu Glu
    1010                1015                1020 ttc tct gag gaa atg gtt ggg gcc aag tct cgg aat ata gca tac ctc      3121
Phe Ser Glu Glu Met Val Gly Ala Lys Ser Arg Asn Ile Ala Tyr Leu
1025                1030                1035                1040 aaa gga aaa gta cct tca tgg gtc ggt gtc cca acg tca gtt gcg ata      3169
Lys Gly Lys Val Pro Ser Trp Val Gly Val Pro Thr Ser Val Ala Ile
                1045                1050                1055 cca ttt ggc act ttt gag aag gtt ttg tca gat ggg ctt aat aag gaa      3217
Pro Phe Gly Thr Phe Glu Lys Val Leu Ser Asp Gly Leu Asn Lys Glu
            1060                1065                1070 gta gca cag agc ata gag aag ctt aag atc aga ctt gcc caa gaa gat      3265
Val Ala Gln Ser Ile Glu Lys Leu Lys Ile Arg Leu Ala Gln Glu Asp
        1075                1080                1085 ttt agt gct cta ggt gaa ata aga aaa gtc gtc ctt aat ctt act gct      3313
Phe Ser Ala Leu Gly Glu Ile Arg Lys Val Val Leu Asn Leu Thr Ala
```

```
                                                                     1090              1095              1100
cct atg caa ttg gtt aat gag ctg aag gag agg atg cta ggc tct gga        3361
Pro Met Gln Leu Val Asn Glu Leu Lys Glu Arg Met Leu Gly Ser Gly
1105              1110              1115              1120 atg ccc tgg cct ggt gat gaa gga gac aag cgt tgg gag caa gca tgg        3409
Met Pro Trp Pro Gly Asp Glu Gly Asp Lys Arg Trp Glu Gln Ala Trp
        1125              1130              1135 atg gct att aaa aag gtt tgg gca tca aaa tgg aac gaa aga gca tat        3457
Met Ala Ile Lys Lys Val Trp Ala Ser Lys Trp Asn Glu Arg Ala Tyr
    1140              1145              1150 ttt agc aca cgc aag gtg aaa ctt gat cat gag tac ctt tcg atg gct        3505
Phe Ser Thr Arg Lys Val Lys Leu Asp His Glu Tyr Leu Ser Met Ala
            1155              1160              1165 gtt ctc gtg caa gaa gtt gtg aat gca gat tat gct ttt gtc att cat        3553
Val Leu Val Gln Glu Val Val Asn Ala Asp Tyr Ala Phe Val Ile His
    1170              1175              1180 acc aca aac cca tcg tct gga gat tct tct gag ata tat gct gaa gtg        3601
Thr Thr Asn Pro Ser Ser Gly Asp Ser Ser Glu Ile Tyr Ala Glu Val
1185              1190              1195              1200 gtg aaa ggg ctt ggc gag acc ctc gtg gga gcc tat cct ggt cgt gct        3649
Val Lys Gly Leu Gly Glu Thr Leu Val Gly Ala Tyr Pro Gly Arg Ala
        1205              1210              1215 atg agc ttt gtt tgc aaa aaa gat gac ctt gac tct ccc aag tta ctt        3697
Met Ser Phe Val Cys Lys Lys Asp Asp Leu Asp Ser Pro Lys Leu Leu
    1220              1225              1230 ggt tac cca agc aag cca att ggt ctc ttc ata agg caa tca atc atc        3745
Gly Tyr Pro Ser Lys Pro Ile Gly Leu Phe Ile Arg Gln Ser Ile Ile
            1235              1240              1245 ttc cgt tcc gac tcc aac ggt gag gac ctg gaa ggt tat gct gga gca        3793
Phe Arg Ser Asp Ser Asn Gly Glu Asp Leu Glu Gly Tyr Ala Gly Ala
    1250              1255              1260 gga tta tat gat agt gta ccg atg gat gag gag gat gag gtt gta ctt        3841
Gly Leu Tyr Asp Ser Val Pro Met Asp Glu Glu Asp Glu Val Val Leu
1265              1270              1275              1280 gat tat aca act gac cct ctt ata gta gac cgt gga ttc cga agc tca        3889
Asp Tyr Thr Thr Asp Pro Leu Ile Val Asp Arg Gly Phe Arg Ser Ser
        1285              1290              1295 atc ctc tca agc ata gca cgg gct ggc cat gcc atc gag gag cta tat        3937
Ile Leu Ser Ser Ile Ala Arg Ala Gly His Ala Ile Glu Glu Leu Tyr
    1300              1305              1310 ggt tct cct cag gac gtc gag gga gta gtg aag gat gga aaa atc tat        3985
Gly Ser Pro Gln Asp Val Glu Gly Val Val Lys Asp Gly Lys Ile Tyr
            1315              1320              1325 gta gtc cag aca aga cca cag atg tagtatgtat gcatctatta gacagctcaa      4039
Val Val Gln Thr Arg Pro Gln Met
    1330              1335 taagcactgt tgtacgcttg tatggttggg acatatgggc gttatggcat gtatagttgt    4099
atgcctagat gtacaacacg tgtactcgta tatatatata taaatgctga aacaagcatt    4159
ggtcctgtac tgtagtttct acatttcatt gtcaccaata attaagtgta ctcctatggc    4219
tgggagtcta tgaaaatgga cgtgttgact tattgggtaa taaataattt atatataaaa    4279
aaaaaaaaaa aaaaaaaaaa aaaaaaaaaa aaaaaaaaaa aaaaaaaaa                4329

<210> SEQ ID NO 8
<211> LENGTH: 1336
<212> TYPE: PRT
<213> ORGANISM: Zea Mays

<400> SEQUENCE: 8
```

-continued

```
Pro Asp Gly Thr Thr Val Tyr Lys Asn Arg Ala Leu Arg Thr Pro Phe
 1               5                  10                  15

Val Lys Ser Gly Asp Asn Ser Thr Leu Arg Ile Glu Ile Asp Asp Pro
                20                  25                  30

Gly Val His Ala Ile Glu Phe Leu Ile Phe Asp Glu Thr Gln Asn Lys
            35                  40                  45

Trp Phe Lys Asn Asn Gly Gln Asn Phe Gln Val Gln Phe Gln Ser Ser
        50                  55                  60

Arg His Gln Gly Thr Gly Ala Ser Gly Ala Ser Ser Ser Ala Thr Ser
 65                  70                  75                  80

Thr Leu Val Pro Glu Asp Leu Val Gln Ile Gln Ala Tyr Leu Arg Trp
                85                  90                  95

Glu Arg Arg Gly Lys Gln Ser Tyr Thr Pro Glu Gln Glu Lys Glu Glu
                100                 105                 110

Tyr Glu Ala Ala Arg Ala Glu Leu Ile Glu Glu Val Asn Arg Gly Val
            115                 120                 125

Ser Leu Glu Lys Leu Arg Ala Lys Leu Thr Lys Ala Pro Glu Ala Pro
130                 135                 140

Glu Ser Asp Glu Ser Lys Ser Ser Ala Ser Arg Val Pro Ile Gly Lys
145                 150                 155                 160

Leu Pro Glu Asp Leu Val Gln Val Gln Ala Tyr Ile Arg Trp Glu Gln
                165                 170                 175

Ala Gly Lys Pro Asn Tyr Pro Pro Glu Lys Gln Leu Val Glu Phe Glu
            180                 185                 190

Glu Ala Arg Lys Glu Leu Gln Ala Glu Val Asp Lys Gly Ile Ser Ile
            195                 200                 205

Asp Gln Leu Arg Gln Lys Ile Leu Lys Gly Asn Ile Glu Ser Lys Val
            210                 215                 220

Ser Lys Gln Leu Lys Asn Lys Lys Tyr Phe Ser Val Glu Arg Ile Gln
225                 230                 235                 240

Arg Lys Lys Arg Asp Ile Thr Gln Leu Leu Ser Lys His Lys His Thr
                245                 250                 255

Val Met Glu Asp Lys Val Glu Val Val Pro Lys Gln Pro Thr Val Leu
                260                 265                 270

Asp Leu Phe Thr Lys Ser Leu His Glu Lys Asp Gly Cys Glu Val Leu
            275                 280                 285

Ser Arg Lys Leu Phe Lys Phe Gly Asp Lys Glu Ile Leu Ala Ile Ser
            290                 295                 300

Thr Lys Val Gln Asn Lys Thr Glu Val His Leu Ala Thr Asn His Thr
305                 310                 315                 320

Asp Pro Leu Ile Leu His Trp Ser Leu Ala Lys Asn Ala Gly Glu Trp
                325                 330                 335

Lys Ala Pro Ser Pro Asn Ile Leu Pro Ser Gly Ser Thr Leu Leu Asp
            340                 345                 350

Lys Ala Cys Glu Thr Glu Phe Thr Lys Ser Glu Leu Asp Gly Leu His
            355                 360                 365

Tyr Gln Val Val Glu Ile Glu Leu Asp Asp Gly Gly Tyr Lys Gly Met
            370                 375                 380

Pro Phe Val Leu Arg Ser Gly Glu Thr Trp Ile Lys Asn Asn Gly Ser
385                 390                 395                 400

Asp Phe Phe Leu Asp Phe Ser Thr His Asp Val Arg Asn Ile Lys Ala
                405                 410                 415
```

-continued

```
Ile Leu Lys Asp Asn Gly Asp Ala Gly Lys Gly Thr Ser Lys Ala Leu
            420                 425                 430
Leu Glu Arg Ile Ala Asp Leu Glu Glu Asp Ala Gln Arg Ser Leu Met
        435                 440                 445
His Arg Phe Asn Ile Ala Ala Asp Leu Ala Asp Gln Ala Arg Asp Ala
    450                 455                 460
Gly Leu Gly Ile Val Gly Leu Phe Val Trp Ile Arg Phe Met Ala
465                 470                 475                 480
Thr Arg Gln Leu Thr Trp Asn Lys Asn Tyr Asn Val Lys Pro Arg Glu
            485                 490                 495
Ile Ser Lys Ala Gln Asp Arg Phe Thr Asp Asp Leu Glu Asn Met Tyr
            500                 505                 510
Lys Thr Tyr Pro Gln Tyr Arg Glu Ile Leu Arg Met Ile Met Ala Ala
        515                 520                 525
Val Gly Arg Gly Gly Glu Gly Asp Val Gly Gln Arg Ile Arg Asp Glu
    530                 535                 540
Ile Leu Val Ile Gln Arg Asn Asn Asp Cys Lys Gly Gly Met Met Glu
545                 550                 555                 560
Glu Trp His Gln Lys Leu His Asn Asn Thr Ser Pro Asp Asp Val Val
            565                 570                 575
Ile Cys Gln Ala Leu Ile Asp Tyr Ile Lys Ser Asp Phe Asp Ile Ser
            580                 585                 590
Val Tyr Trp Asp Thr Leu Asn Lys Asn Gly Ile Thr Lys Glu Arg Leu
        595                 600                 605
Leu Ser Tyr Asp Arg Ala Ile His Ser Glu Pro Asn Phe Arg Ser Glu
    610                 615                 620
Gln Lys Ala Gly Leu Leu Arg Asp Leu Gly Asn Tyr Met Arg Ser Leu
625                 630                 635                 640
Lys Ala Val His Ser Gly Ala Asp Leu Glu Ser Ala Ile Ala Ser Cys
            645                 650                 655
Met Gly Tyr Lys Ser Glu Gly Glu Gly Phe Met Val Gly Val Gln Ile
            660                 665                 670
Asn Pro Val Lys Gly Leu Pro Ser Gly Phe Pro Glu Leu Leu Glu Phe
        675                 680                 685
Val Leu Glu His Val Glu Asp Lys Ser Ala Glu Pro Leu Pro Glu Gly
    690                 695                 700
Leu Leu Glu Ala Arg Val Glu Leu Arg Pro Leu Leu Asp Ser Arg
705                 710                 715                 720
Glu Arg Met Lys Asp Leu Ile Phe Leu Asp Ile Ala Leu Asp Ser Thr
            725                 730                 735
Phe Arg Thr Ala Ile Glu Arg Ser Tyr Glu Glu Leu Asn Asp Ala Ala
            740                 745                 750
Pro Glu Lys Ile Met Tyr Phe Ile Ser Leu Val Leu Glu Asn Leu Ala
        755                 760                 765
Leu Ser Ile Asp Asp Asn Glu Asp Ile Leu Tyr Cys Leu Lys Gly Trp
    770                 775                 780
Asn Gln Ala Leu Glu Met Ala Lys Gln Lys Asp Gln Trp Ala Leu
785                 790                 795                 800
Tyr Ala Lys Ala Phe Leu Asp Arg Asn Arg Leu Ala Leu Ala Ser Lys
            805                 810                 815
Gly Glu Gln Tyr His Asn Met Met Gln Pro Ser Ala Glu Tyr Leu Gly
            820                 825                 830
Ser Leu Leu Ser Ile Asp Gln Trp Ala Val Asn Ile Phe Thr Glu Glu
```

-continued

Ile Ile Arg Gly Gly Ser Ala Ala Thr Leu Ser Ala Leu Leu Asn Arg
835             840             845
                850             855             860

Phe Asp Pro Val Leu Arg Asn Val Ala His Leu Gly Ser Trp Gln Val
865             870             875             880

Ile Ser Pro Val Glu Ser Gly Tyr Val Val Val Asp Glu Leu
                885             890             895

Leu Ala Val Gln Asn Lys Ser Tyr Asp Lys Pro Thr Ile Leu Val Ala
                900             905             910

Lys Ser Val Lys Gly Glu Glu Glu Ile Pro Asp Gly Val Gly Val
                915             920             925

Ile Thr Pro Asp Met Pro Asp Val Leu Ser His Val Ser Val Arg Ala
930             935             940

Arg Asn Ser Lys Val Leu Phe Ala Thr Cys Phe Asp His Thr Thr Leu
945             950             955             960

Ser Glu Leu Glu Gly Tyr Asp Gln Lys Leu Phe Ser Phe Lys Pro Thr
                965             970             975

Ser Ala Asp Ile Thr Tyr Arg Glu Ile Thr Glu Ser Glu Leu Gln Gln
                980             985             990

Ser Ser Ser Pro Asn Ala Glu Val Gly His Ala Val Pro Ser Ile Ser
                995             1000            1005

Leu Ala Lys Lys Lys Phe Leu Gly Lys Tyr Ala Ile Ser Ala Glu Glu
1010            1015            1020

Phe Ser Glu Glu Met Val Gly Ala Lys Ser Arg Asn Ile Ala Tyr Leu
1025            1030            1035            1040

Lys Gly Lys Val Pro Ser Trp Val Gly Val Pro Thr Ser Val Ala Ile
                1045            1050            1055

Pro Phe Gly Thr Phe Glu Lys Val Leu Ser Asp Gly Leu Asn Lys Glu
                1060            1065            1070

Val Ala Gln Ser Ile Glu Lys Leu Lys Ile Arg Leu Ala Gln Glu Asp
                1075            1080            1085

Phe Ser Ala Leu Gly Glu Ile Arg Lys Val Val Leu Asn Leu Thr Ala
                1090            1095            1100

Pro Met Gln Leu Val Asn Glu Leu Lys Glu Arg Met Leu Gly Ser Gly
1105            1110            1115            1120

Met Pro Trp Pro Gly Asp Gly Asp Lys Arg Trp Glu Gln Ala Trp
                1125            1130            1135

Met Ala Ile Lys Lys Val Trp Ala Ser Lys Trp Asn Glu Arg Ala Tyr
                1140            1145            1150

Phe Ser Thr Arg Lys Val Lys Leu Asp His Glu Tyr Leu Ser Met Ala
                1155            1160            1165

Val Leu Val Gln Glu Val Val Asn Ala Asp Tyr Ala Phe Val Ile His
1170            1175            1180

Thr Thr Asn Pro Ser Ser Gly Asp Ser Ser Glu Ile Tyr Ala Glu Val
1185            1190            1195            1200

Val Lys Gly Leu Gly Glu Thr Leu Val Gly Ala Tyr Pro Gly Arg Ala
                1205            1210            1215

Met Ser Phe Val Cys Lys Lys Asp Asp Leu Asp Ser Pro Lys Leu Leu
                1220            1225            1230

Gly Tyr Pro Ser Lys Pro Ile Gly Leu Phe Ile Arg Gln Ser Ile Ile
                1235            1240            1245

Phe Arg Ser Asp Ser Asn Gly Glu Asp Leu Glu Gly Tyr Ala Gly Ala
1250            1255            1260

```
Gly Leu Tyr Asp Ser Val Pro Met Asp Glu Glu Asp Glu Val Val Leu
1265                1270                1275                1280

Asp Tyr Thr Thr Asp Pro Leu Ile Val Asp Arg Gly Phe Arg Ser Ser
            1285                1290                1295

Ile Leu Ser Ser Ile Ala Arg Ala Gly His Ala Ile Glu Glu Leu Tyr
        1300                1305                1310

Gly Ser Pro Gln Asp Val Glu Gly Val Val Lys Asp Gly Lys Ile Tyr
        1315                1320                1325

Val Val Gln Thr Arg Pro Gln Met
    1330                1335

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 9
gcaaagtttt caaggacaag actgatgaag                                    30

<210> SEQ ID NO 10
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 10
ccagatggca cgacagtgta caagaaca                                      28

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: Primer
<221> NAME/KEY: modified_base
<222> LOCATION: (15)
<223> OTHER INFORMATION: i
<221> NAME/KEY: modified_base
<222> LOCATION: (18)
<223> OTHER INFORMATION: i

<400> SEQUENCE: 11
aatgactgca aaggnggnat gatgga                                        26
```

NUCLEIC ACID MOLECULES FROM MAIZE AND THEIR USE FOR THE PRODUCTION OF MODIFIED STARCH

This application is a continuation of international application PCT/EP97/07123, filed on Dec. 18, 1997, which designated the United States.

The present invention relates to nucleic acid molecules encoding a starch granule-bound protein from maize as well as to methods and recombinant DNA molecules for the production of transgenic plant cells and plants synthesizing modified starch. The invention also relates to the transgenic plant cells and plants resulting from these methods and to the starch obtainable from the transgenic plant cells and plants.

The polysaccharide starch, which constitutes one of the most important storage substances in plants, is not only used in the area of foodstuffs but also plays a significant role as a regenerative material in the manufacturing of industrial products. In order to enable the use of this raw material in as many areas as possible, it is necessary to obtain a large variety of substances as well as to adapt these substances to the varying demands of the processing industry.

Although starch consists of a chemically homogeneous basic component, namely glucose, it does not constitute a homogeneous raw material. It is rather a complex mixture of various types of molecules which differ from each other in their degree of polymerization and in the degree of branching of the glucose chains. One differentiates particularly between amylose-starch, a basically non-branched polymer made up of α-1,4-glycosidically branched glucose molecules, and amylopectin-starch which in turn is a mixture of more or less heavily branched glucose chains. The branching results from the occurrence of α-1,6-glycosidic interlinkings.

The molecular structure of starch which is mainly determined by its degree of branching, the amylose/amylopectin ration, the average chain-length and the occurrence of phosphate groups is significant for important functional properties of starch or, respectively, its watery solutions. Important functional properties are for example solubility of the starch, tendency to retrogradation, capability of film formation, viscosity, pastification properties, i.e. binding and gluing properties, as well as cold resistance. The starch granule size may also be significant for the various uses. The production of starch with a high amylose content is particularly significant. Furthermore, modified starch contained in plant cells may, under certain conditions, favorably alter the behavior of the plant cell. For example, it would be possible to decrease the starch degradation during the storage of the starch-containing organs such as seeds and tubers prior to their further processing by, for example, starch extraction. Moreover, there is some interest in producing modified starches which would render plant cells and plant organs containing this starch more suitable for further processing, such as for the production of popcorn or corn flakes from maize or of French fries, crisps or potato powder from potatoes. There is a particular interest in improving the starches in such a way, that they show a reduced "cold sweetening", i.e. a decreased release of reduced sugars (especially glucose) during long-term storage at low temperatures.

Starch which can be isolated from plants is often adapted to certain industrial purposes by means of chemical modifications which are usually time-consuming and expensive. Therefore it is desirable to find possibilities to produce plants synthesizing a starch the properties of which already meet the demands of the processing industry.

Conventional methods for producing such plants are classical breeding methods and the production of mutants. Thus, for example, a mutant was produced from maize synthesizing starch with an altered viscosity (U.S. Pat. No. 5,331,108) and a maize variety (waxy maize) was established by means of breeding the starch of which consists of almost 100% amylopectin (Akasuka and Nelson, J. Biol. Chem. 241 (1966), 2280–2285). Furthermore, mutants of maize and pea have been described which synthesize starches with a high amylose content (70% in maize or up to 50% in pea). These mutants have so far not been characterized on the molecular level and therefore do not allow for the production of corresponding mutants in other starch-storing plants.

Alternatively, plants synthesizing starch with altered properties may be produced by means of recombinant DNA techniques. In various cases, for example, the recombinant modification of potato plants aiming at altering the starch synthesized in these plants has been described (e.g. WO 92/11376; WO 92/14827). However, in order to make use of recombinant DNA techniques, DNA sequences are required the gene products of which influence starch synthesis, starch modification or starch degradation.

Therefore, the problem underlying the present invention is to provide nucleic acid molecules and methods which allow for the alteration of plants in such a way, that they synthesize a starch which differs from starch naturally synthesized in plants with respect to its physical and/or chemical properties and is therefore more suitable for general and/or particular uses.

This problem is solved by the provision of the embodiments described in the claims.

Therefore, the present invention relates to nucleic acid molecules encoding a protein comprising the amino acid sequence indicated in Seq ID No. 6 or in Seq ID No. 8. Such proteins are present in the plastids of plant cells, bound to starch granules as well as in free, i.e. soluble form.

The present invention further relates to nucleic acid molecules comprising a sequence with the nucleotide sequence indicated in Seq ID No. 5 or in Seq ID No. 7, particularly the coding region indicated in Seq ID No. 5 or in Seq ID No. 7.

Nucleic acid molecules encoding a protein from maize, which in the plastids of the cells is partly granule-bound, and hybridizing to the above-mentioned nucleic acid molecules of the invention or their complementary strand are also the subject matter of the present invention. In this context the term "hybridization" signifies hybridization under conventional hybridizing conditions, preferably under stringent conditions as described for example in Sambrook et al., Molecular Cloning, A Laboratory Manual, 2$^{nd}$ Edition (1989) Cold Spring Harbor Laboratory Press, Cold Spring Harbor, N.Y.).

More preferably hybridization occurs under the following conditions:

| | |
|---|---|
| Hybridization buffer: | 2 × SSC; 10 × Denhard's solution (Fikoll 400 + PEG + BSA; ratio 1:1:1); 0.1% SDS; 5 mM EDTA; 50 mM Na$_2$HPO$_4$; 250 µg/ml herring sperm DNA; 50 µg/ml tRNA; or 0.25 M sodiumphosphate buffer pH 7.2 1 mM EDTA 7% SDS |

-continued

| | |
|---|---|
| Hybridization temperature | T = 65 + 68° C. |
| Washing buffer: | 0.2 × SSC; 0.1% SDS |
| Washing temperature | T = 40 to 68° C. |

Nucleic acid molecules hybridizing to the molecules according to the invention may be isolated e.g. from genomic or from cDNA libraries produced from maize cells or tissue.

The identification and isolation of such nucleic acid molecules may take place by using the molecules according to the invention or parts of these molecules or, as the case may be, the reverse complementary strands of these molecules, e.g. by hybridization according to standard methods (see e.g. Sambrook et al., 1989, Molecular Cloning, A Laboratory Manual, 2nd Edition, Cold Spring Harbor Laboratory Press, Cold Spring Harbor, N.Y.).

As a probe for hybridization e.g. nucleic acid molecules may be used which exactly or basically contain the nucleotide sequence indicated under Seq ID No. 5 or under Seq ID No. 7 or parts thereof. The DNA fragments used as hybridization probe may also be synthetic DNA fragments which were produced by means of the conventional DNA synthesizing methods and the sequence of which is basically identical with that of a nucleic acid molecule of the invention. After identifying and isolating genes hybridizing to the nucleic acid sequences according to the invention, the sequence has to be determined and the properties of the proteins encoded by this sequence have to be analyzed.

Such hybridizing nucleic acid molecules also encompass fragments, derivatives and allelic variants of the above-mentioned nucleic acid molecules, which encode the above-mentioned protein. In this context fragments are described as parts of the nucleic acid molecules which are long enough in order to encode the above-described protein. The term derivative means that the sequences of these molecules differ from the sequences of the above-mentioned nucleic acid molecules at one or more positions and exhibit a high degree of homology to the sequences of these molecules. Homology means a sequence identity of at least 40%, in particular an identity of at least 60%, preferably of more than 80% and still more preferably a sequence identity of more than 90% and particularly preferred of more than 95%. The deviations occurring when comparing with the above-described nucleic acid molecules might have been caused by addition, deletion, substitution, insertion or recombination:

Moreover, homology means that functional and/or structural equivalence exists between the respective nucleic acid molecules or the proteins they encode. The nucleic acid molecules, which are homologous to the above-described nucleic acid molecules and represent derivatives of these molecules, are generally variations of these nucleic acid molecules, that constitute modifications which exert the same biological function. These variations may be naturally occurring variations or mutations, whereby these mutations may have occurred naturally or they may have been introduced deliberately. Moreover the variations may be synthetically produced sequences.

The allelic variants may be naturally occurring as well as synthetically produced variants or variants produced by recombinant DNA techniques.

The proteins encoded by the various variants of the nucleic acid molecules according to the invention exhibit certain common characteristics. Enzyme activity, molecular weight, immunologic reactivity, conformation etc. may belong to these characteristics as well as physical properties such as the mobility in gel electrophoresis, chromatographic characteristics, sedimentation coefficients, solubility, spectroscopic properties, stability, pH-optimum, temperature-optimum etc.

Furthermore, the present invention relates to nucleic acid molecules the sequences of which, compared to the sequences of the above-mentioned molecules, are degenerated due to the genetic code and which encode a protein which is present in the plastids of plant cells partly in granule-bound and partly in free form, i.e. in a soluble form.

The nucleic acid molecules of the invention can, for example, be isolated from natural sources, produced by methods of genetic engineering, e.g. by PCR, or produced by means of synthesis methods known to the skilled person.

The nucleic acid molecules of the invention may be DNA molecules, such as cDNA or genomic DNA, as well as RNA molecules.

Furthermore, the invention relates to vectors, especially plasmids, cosmids, viruses, bacteriophages and other vectors common in genetic engineering, which contain the above-mentioned nucleic acid molecules of the invention.

In a preferred embodiment the nucleic acid molecules contained in the vectors are linked to regulatory elements that ensure the transcription and synthesis of a translatable RNA in prokaryotic and eukaryotic cells.

In a further embodiment the invention relates to host cells, in particular prokaryotic or eukaryotic cells, which have been transformed and/or recombinantly manipulated by an above-mentioned nucleic acid molecule of the invention or by a vector of the invention, as well as cells which are derived from such cells and which contain a nucleic acid molecule of the invention or a vector of the invention. This is preferably a bacterial cell or a plant cell.

It was now found that the protein encoded by the nucleic acid molecules of the invention influences the starch synthesis or modification and that changes in the amount of the protein in plant cells lead to changes in the starch metabolism of the plant, especially to the synthesis of starch with modified physical and chemical properties.

By providing the nucleic acid molecules of the invention it is possible to produce plants by means of recombinant DNA techniques synthesizing a modified starch which differs from the starch synthesized in wildtype plants with respect to its structure and its physical and chemical properties. For this purpose, the nucleic acid molecules of the invention are linked to regulatory elements, which ensure the transcription and translation in plant cells, and they are introduced into the plant cells.

Therefore, the present invention also relates to transgenic plant cells containing a nucleic acid molecule of the invention wherein the same is linked to regulatory elements which ensure the transcription in plant cells. The regulatory elements are preferably heterologous with respect to the nucleic acid molecule.

Such plant cells of the invention differ from naturally occurring plants among other things in that at least one copy of the nucleic acid molecule of the invention is integrated in their genome, possibly in addition to the naturally occurring copies. Furthermore, this/these additional copy/copies is/are integrated at a location in the genome at which they do not occur naturally. This may be proved, for example, by means of a Southern Blot analysis. Furthermore, such transgenic plant cells can preferably be distinguished from corresponding naturally occurring plant cells by at least one of the following features: If the nucleic acid molecule according to the invention, which was introduced into the plant cells, is heterologous to the plant cells, the transgenic cells can be distinguished from non transformed cells due to the presence of transcripts from the introduced molecule according to the invention. Such transcripts can be detected, e.g., by Northern Blot analysis. Preferably the transgenic cells furthermore contain the protein encoded by the nucleic acid molecule according to the invention. The presence of the protein can be detected, e.g., by immunological methods such as Western Blot analysis.

If the nucleic acid molecule according to the invention which was introduced into the cells is homologous with respect to the cells, the transgenic cells can be distinguished from non-transformed cells, for example, due to the additional expression of the nucleic acid molecule according to the invention. In particular, the transgenic cells contain preferably more transcripts of the nucleic acid molecules according to the invention. This can be detected, e.g., by Northern Blot analysis. "More" preferably means at least 10% more, more preferably at least 20% more, and even more preferably at least 50% more. Accordingly, the transgenic cells contain preferably more protein according to the invention in comparison to non-transformed cells. This can be detected, e.g., by Western Blot analysis. Preferably, the cells contain at least 10% more protein according to the invention, more preferably at least 20% and even more preferably at least 50% more.

By means of methods known to the skilled person the transgenic plant cells can be regenerated to whole plants. The plants obtainable by regenerating the transgenic plant cells of the invention are also the subject-matter of the present invention.

A further subject-matter of the invention are plants which contain the above-described transgenic plant cells. The transgenic plants may in principle be plants of any desired species, i.e. they may be monocotyledonous as well as dicotyledonous plants. These are preferably useful plants, in particular starch-synthesizing or starch-storing plants such as cereals (rye, barley, oats, wheat, millet, sago etc.), rice, maize, peas, wrinkled peas, cassava, potato, tomato, oil seed rape, soy bean, hemp, flax, sunflower, cow-pea and arrow-root.

The present invention also relates to a process for the production of a modified starch comprising the step of extracting from the above-described plants according to the invention and/or from starch storing parts of such plants the starch. Preferably, such a process furthermore comprises the steps of cultivating plants according to the invention and harvesting the cultivated plants and/or starch storing parts of these plants before the extraction of the starch.

Methods for extracting starch from plants or from starch storing parts of plants are well known to the person skilled in the art. Methods to extract starch from maize seeds are described, for example, in Eckhoff et al. (Cereal Chem. 73 (1996), 54–57). Extraction of maize starch on an industrial scale is normally achieved by "wet-milling". Furthermore, methods for the extraction of starch from various starch storing plants are described, for example, in Starch: Chemistry and Technology (eds.: Whistler, BeMiller and Paschall (1994) 2nd Edition, Academic Press Inc. London LTD; ISBN 0-12-746270-8; see e.g. Chapter XII, page 417–468: Corn and *Sorghum* Starches: Production; by Watson, S. A.; Chapter XIII, page 469–479: Tapioca, Arrowroot and Sago Starches: Production; by Corbishley and Miller; Chapter XIV, page 479–490: Potato Starch: Production and Uses; by Mitch; Chapter XV, page 491–506: Wheat starch: Production, Modification and Uses; by Knight and Olson; and Chapter XVI, page 507–528: Rice starch: Production and Uses; by Rohwer and Klem). Means usually used in methods for the extraction of starches from plant materials are separators, decanters, hydroclones and different kinds of machines for drying the starch, e.g., spray drier or jet drier.

The present invention also relates to the starch obtainable from the transgenic plant cells and plants of the invention or by the above described process. Due to the expression or the additional expression of a nucleic acid molecule of the invention, the transgenic plant cells and plants of the invention synthesize a starch which is modified when compared to starch from wildtype-plants, i.e. non-transformed plants. In particular, such a starch has preferably a higher phosphate content than starch synthesized by corresponding non-transformed cells or plants. A higher phosphate content preferably means that the starch contains at least 10% more phosphate, more preferably at least 30%, even more preferably at least 50% and particularly preferred at least 100% more phosphate than starch from corresponding non-transformed cells or plants. Starches with a high content of phosphate are, for example, of particular interest for the paper industry, e.g., for the preparation of the surface of paper. Normally, the paper industry uses chemically modified starch, for example, hydroxyethylated or phosphorylated starch, for the surface sizing or coating. The production of highly phosphorylated starch in plants would thus avoid the necessity to chemically modify starch in order to adapt it to the requirements of the paper industry.

A further subject-matter of the present invention is a method for the production of a protein which is present in plant cells in granule-bound form as well as in soluble from, in which host cells of the invention are cultivated under conditions that allow for the expression of the protein and in which the protein is then isolated from the cultivated cells and/or the culture medium.

Furthermore, the invention relates to proteins encoded by the nucleic acid molecules of the invention as well as to proteins obtainable by the above-described method. These are preferably proteins from maize encoded by nuclear genes and which are localized in the plastids. In the plastids these enzymes are present in granule-bound as well as in free form.

A further subject-matter of the invention are antibodies which specifically recognize a protein of the invention. These may be monoclonal as well as polyclonal antibodies. Methods for the production of such antibodies are known to the skilled person.

Furthermore, the present invention relates to nucleic acid molecules specifically hybridizing with a nucleic acid molecule of the invention and exhibiting a length of at least 15 nucleotides. In this context specifically hybridizing signifies that under conventional hybridization conditions, preferably under stringent conditions, cross-hybridization with sequences encoding other proteins do not significantly occur. Such nucleic acid molecules preferably have a length of at least 20, more preferably a length of at least 50 and most preferably a length of at least 100 nucleotides. Such molecules can be used, for example, as PCR primers, as hybridization probes or as DNA molecules which encode antisense RNA.

Furthermore, it was found that it is possible to influence the properties of the starch synthesized in plant cells by reducing the amount of proteins encoded by the nucleic acid molecules according to the invention in the cells. This reduction may be effected, for example, by means of antisense expression of the nucleic acid molecules of the invention, expression of suitable ribozymes or cosuppression.

Therefore, DNA molecules encoding an antisense RNA which is complementary to transcripts of a DNA molecule of the invention are also the subject-matter of the present invention, as well as these antisense molecules. Thereby, complementary does not signify that the encoded RNA has to be 100% complementary. A low degree of complementarity is sufficient, as long as it is high enough in order to inhibit the expression of a protein of the invention upon expression in plant cells. The transcribed RNA is preferably at least 90% and most preferably at least 95% complementary to the transcript of the nucleic acid molecule of the invention. In order to cause an antisense-effect during the transcription in plant cells such DNA molecules have a length of at least 15 bp, preferably a length of more than 100 bp and most preferably a length of more than 500 bp, however, usually less than 5000 bp, preferably shorter than 2500 bp.

The invention further relates to DNA molecules which, during expression in plant cells, lead to the synthesis of an RNA which in the plant cells due to a cosupression-effect reduces the expression of the nucleic acid molecules of the invention encoding the described protein. The invention also relates to RNA molecules encoded thereby. The principle of the cosupression as well as the production of corresponding DNA sequences is precisely described, for example, in WO 90/12084. Such DNA molecules preferably encode a RNA having a high degree of homology to transcripts of the nucleic acid molecules of the invention. It is, however, not absolutely necessary that the coding RNA is translatable into a protein.

In a further embodiment the present invention relates to DNA molecules encoding an RNA molecule with ribozyme activity which specifically cleaves transcripts of a DNA molecule of the invention as well as these encoded RNA molecules.

Ribozymes are catalytically active RNA molecules capable of cleaving RNA molecules and specific target sequences. By means of recombinant DNA techniques it is possible to alter the specificity of ribozymes. There are various classes of ribozymes. For practical applications aiming at the specific cleavage of the transcript of a certain gene, use is preferably made of representatives of two different groups of ribozymes. The first group is made up of ribozymes which belong to the group I intron ribozyme type. The second group consists of ribozymes which as a characteristic structural feature exhibit the so-called "hammerhead" motif. The specific recognition of the target RNA molecule may be modified by altering the sequences flanking this motif. By base pairing with sequences in the target molecule these sequences determine the position at which the catalytic reaction and therefore the cleavage of the target molecule takes place. Since the sequence requirements for an efficient cleavage are low, it is in principle possible to develop specific ribozymes for practically each desired RNA molecule.

In order to produce DNA molecules encoding a ribozyme which specifically cleaves transcripts of a DNA molecule of the invention, for example a DNA sequence encoding a catalytic domain of a ribozyme is bilaterally linked with DNA sequences which are homologous to sequences of the target enzyme. Sequences encoding the catalytic domain may for example be the catalytic domains of the satellite DNA of the SCMo virus (Davies et al., Virology 177 (1990), 216–224) or that of the satellite DNA of the TobR virus (Steinecke et al., EMBO J. 11 (1992), 1525–1530; Haseloff and Gerlach, Nature 334 (1988), 585–591). The DNA sequences flanking the catalytic domain are preferably derived from the above-described DNA molecules of the invention.

In a further embodiment the present invention relates to vectors containing the above-described DNA molecules, in particular those in which the described DNA molecules are linked with regulatory elements ensuring the transcription in plant cells.

Furthermore, the present invention relates to host cells containing the described DNA molecules or vectors. The host cell may be a prokaryotic cell, such as a bacterial cell, or a eukaryotic cell. The eukaryotic host cells are preferably plant cells.

Furthermore, the invention relates to transgenic plant cells containing an above-described DNA molecule encoding an antisense-RNA, a ribozyme or an RNA which leads to a cosuppression effect, whereby the DNA molecule is linked to DNA elements ensuring the transcription in plant cells. These transgenic plant cells may be regenerated to whole plants according to well-known techniques. Thus, the invention also relates to plants which may be obtained through regeneration from the described transgenic plant cells, as well as to plants containing the described transgenic plant cells. The transgenic plants themselves may be plants of any desired plant species, preferably useful plants, particularly starch-storing ones, as indicated above, and most preferably maize plant cells.

Furthermore, the invention relates to the antisense RNA molecules encoded by the described DNA molecules, as well as to RNA molecules with ribozyme activity and RNA molecules which lead to a cosuppression effect which are obtainable, for example, by means of transcription.

A further subject-matter of the invention is a method for the production of transgenic plant cells, which in comparison to non-transformed cells synthesize a modified starch. In this method the amount of proteins encoded by the DNA molecules of the invention, which are present in the cells in endogenic form, is reduced in the plant cells.

In a preferred embodiment this reduction is effected by means of an antisense effect. For this purpose the DNA molecules of the invention or parts thereof are linked in antisense orientation with a promoter ensuring the transcription in plant cells and possibly with a termination signal ensuring the termination of the transcription as well as the polyadenylation of the transcript. In order to ensure an efficient antisense effect in the plant cells the synthesized antisense RNA should exhibit a minimum length of 15 nucleotides, preferably of at least 100 nucleotides and most preferably of at least 500 nucleotides. Furthermore, the DNA sequence encoding the antisense RNA should be homologous with respect to the plant species to be transformed. However, DNA sequences exhibiting a high degree of homology to DNA sequences which are present in the cells in endogenic form may also be used, preferably with an homology of more than 90% and most preferably with an homology of more than 95%.

In a further embodiment the reduction of the amount of proteins encoded by the DNA molecules of the invention is effected by a ribozyme effect. The basic effect of ribozymes as well as the construction of DNA molecules encoding such RNA molecules have already been described above. In order to express an RNA with ribozyme activity in transgenic cells the above described DNA molecules encoding a ribozyme are linked with DNA elements which ensure the transcription in plant cells, particularly with a promoter and a termination signal. The ribozymes synthesized in the plant cells lead to the cleavage of transcripts of DNA molecules of the invention which are present in the plant cells in endogenic form.

A further possibility in order to reduce the amount of proteins encoded by the nucleic acid molecules of the invention is cosupression. Therefore, the plant cells obtainable by the method of the invention are a further subject matter. These plant cells are characterized in that their amount of proteins encoded by the DNA molecules of the invention is reduced and that in comparison to wildtype cells they synthesize a modified starch.

Preferably, the transgenic cells show a reduction in the amount of transcripts encoding a protein according to the present invention of at least 30%, more preferably of at least 50%, even more preferably of at least 70% and most preferably of at least 90% in comparison to corresponding non-transformed cells. The amount of transcripts can be determined, for example, by Northern Blot analysis. Furthermore, the cells preferably show a corresponding reduction of the amount of the protein according to the invention. This can be determined, for example, by immunological methods such as Western Blot analysis.

In a particularly preferred embodiment of the present invention not only the synthesis of a protein of the invention is reduced in the transformed plant cells, but moreover also the synthesis of at least one further enzyme involved in starch synthesis and/or modification. In this context, for example, starch granule-bound starch synthases or branching enzymes are preferred.

Furthermore, the invention relates to plants obtainable by regeneration of the described plant cells as well as to plants containing the described cells of the invention.

The present invention also relates to a process for the production of a modified starch comprising the step of extracting from the above-described plants according to the invention and/or from starch storing parts of such plants the starch. Preferably, such a process furthermore comprises the steps of cultivating plants according to the invention; and harvesting the cultivated plants and/or starch storing parts of these plants before the extraction of the starch.

The present invention also relates to the starch obtainable from the described transgenic plant cells and plants or obtainable by the above described process. Due to the expression of the described DNA molecules encoding antisense RNA, a ribozyme or a cosupression RNA in the transgenic plant cells the amount of proteins encoded by the DNA molecules of the invention which are present in the cells in endogenic form, is reduced. Surprisingly, this reduction leads to a drastic change of the physical and chemical properties of the starch synthesized in the plant cells. When compared to starch from non-transformed cells or plants the modified starch preferably exhibits altered pastification properties, i.e. an altered viscosity of the watery solutions of the starch and/or an altered, in particular a reduced phosphate content.

The expression of the nucleic acid molecules of the invention may in principle take place in any kind of plant species. Monocotyledonous and dicotyledonous plants are preferred, in particular useful plants and preferably starch-storing plants such as cereals (rye, barley, oats, wheat, millet, sago etc.), rice, maize, peas, wrinkled peas, cassava, potato, tomato, oilseed rape, soy bean, hemp, flax, sunflower, cow-pea and arrowroot.

Within the framework of the present invention the term "regulatory DNA elements ensuring the transcription in plant cells" are DNA regions which allow for the initiation or the termination of transcription in plant cells. DNA regions ensuring the initiation of transcription are in particular promoters.

For the expression of the various above-described DNA molecules of the invention in plants any promoter functioning in plant cells may be used. The promoter may be homologous or heterologous with respect to the used plant species. Use may, for example, be made of the 35S promoter of the cauliflower mosaic virus (Odell et al., Nature 313 (1985), 810–812) which ensures a constitutive expression in all plant tissues and also of the promoter construct described in WO/9401571. However, use may also be made of promoters which lead to an expression of subsequent sequences only at a point of time determined by exogenous factors (such as in WO/9307279) or in a particular tissue of the plant (see e.g. Stockhaus et al., EMBO J. 8 (1989), 2245–2251). Promoters which are active in the starch-storing parts of the plant to be transformed are preferably used. In the case of maize these parts are the maize seeds, in the case of potatoes the tubers. In order to transform potatoes the tuber-specific B33-promoter (Rocha-Sosa et al., EMBO J. 8 (1989), 23–29) may be used particularly, but not exclusively. Apart from promoters, DNA regions initiating transcription may also contain DNA sequences ensuring a further increase of transcription, such as the so-called enhancer-elements. Furthermore, the term "regulatory DNA elements" may also comprise termination signals which serve to correctly end the transcription and to add a poly-A-tail to the transcript which is believed to stabilize the transcripts. Such elements are described in the literature and can be exchanged as desired. Examples for such termination sequences are the 3'-nontranslatable regions comprising the polyadenylation signal of the nopaline synthase gene (NOS gene) or the octopine synthase gene (Gielen et al., EMBO J. 8 (1989), 23–29) from *agrobacteria*, or the 3'-nontranslatable regions of the genes of the storage proteins from soy bean as well as the genes of the small subunit of ribulose-1,5-biphosphate-carboxylase (ssRUBISCO).

The introduction of the DNA molecules of the invention into plant cells is preferably carried out using plasmids. Plasmids ensuring a stable integration of the DNA into the plant genome are preferred.

In order to prepare the introduction of foreign genes in higher plants a large number of cloning vectors are at disposal, containing a replication signal for *E. coli* and a marker gene for the selection of transformed bacterial cells. Examples for such vectors are pBR322, pUC series, M13 mp series, pACYC184 etc. The desired sequence may be integrated into the vector at a suitable restriction site. The obtained plasmid is used for the transformation of *E. coli* cells. Transformed *E. coli* cells are cultivated in a suitable medium and subsequently harvested and lysed. The plasmid is recovered by means of standard methods. As an analyzing method for the characterization of the obtained plasmid DNA use is generally made of restriction analysis and sequence analysis. After each manipulation the plasmid DNA may be cleaved and the obtained DNA fragments may be linked to other DNA sequences.

In order to introduce DNA into plant host cells a wide range of techniques are at disposal. These techniques comprise the transformation of plant cells with T-DNA by using *Agrobacterium tumefaciens* or *Agrobacterium rhizogenes* as transformation medium, the fusion of protoplasts, the injection and the electroporation of DNA, the introduction of DNA by means of the biolistic method as well as further possibilities.

In the case of injection and electroporation of DNA into plant cells, there are no special demands made to the plasmids used. Simple plasmids such as pUC derivatives may be used. However, in case that whole plants are to be regenerated from cells transformed in such a way, a selectable marker gene should be present.

Depending on the method of introducting desired genes into the plant cell, further DNA sequences may be necessary. If the Ti- or Ri-plasmid is used e.g. for the transformation of the plant cell, at least the right border, more frequently, however, the right and left border of the Ti- and Ri-plasmid T-DNA has to be connected to the foreign gene to be introduced as a flanking region.

If *Agrobacteria* are used for transformation, the DNA which is to be introduced must be cloned into special plasmids, namely either into an intermediate vector or into a binary vector. Due to sequences homologous to the sequences within the T-DNA, the intermediate vectors may be integrated into the Ti- or Ri-plasmid of the *Agrobacterium* due to homologous recombination. This also contains the vir-region necessary for the transfer of the T-DNA. Intermediate vectors cannot replicate in *Agrobacteria*. By means of a helper plasmid the intermediate vector may be transferred to *Agrobacterium tumefaciens* (conjugation). Binary vectors may replicate in *E. coli* as well as in *Agrobacteria*. They contain a selectable marker gene as well as a linker or polylinker which is framed by the right and the left T-DNA border region. They may be transformed directly into the *Agrobacteria* (Holsters et al. Mol. Gen. Genet. 163 (1978), 181–187). The plasmids used for the transformation of the *Agrobacteria* further comprise a selectable marker gene, such as the NPT II gene which allows for selecting transformed bacteria. The *Agrobacterium* acting as host cell should contain a plasmid carrying a vir-region. The vir-region is necessary for the transfer of the T-DNA into the plant cell. Additional T-DNA may be present. The *Agrobacterium* transformed in such a way is used for the transformation of plant cells.

The use of T-DNA for the transformation of plant cells was investigated intensely and described sufficiently in EP 120 516; Hoekema, In: The Binary Plant Vector System Offsetdrukkerij Kanters B. V., Alblasserdam (1985), Chapter V; Fraley et al., Crit. Rev. Plant. Sci., 4, 1–46 and An et al. EMBO J. 4 (1985), 277–287. Some binary vectors may already be obtained commercially, such as pBIN19 (Clontech Laboratories, Inc., USA).

For transferring the DNA into the plant cells, plant explants may suitably be co-cultivated with *Agrobacterium tumefaciens* or *Agrobacterium rhizogenes*. From the infected plant material (e.g. pieces of leaves, stem segments, roots, but also protoplasts or suspension-cultivated plant cells) whole plants may then be regenerated in a suitable medium which may contain antibiotics or biozides for the selection of transformed cells. The plants obtained in such a way may then be examined as to whether the introduced DNA is present or not. Other possibilities in order to introduce foreign DNA by using the biolistic method or by transforming protoplasts are known to the skilled person (cf. e.g. Willmitzer, L., 1993 Transgenic plants. In: Biotechnology, A Multi-Volume Comprehensive Treatise (H. J. Rehm, G. Reed, A. Pühler, P. Stadler, editors), Vol. 2, 627–659, VCH Weinheim-New York-Basel-Cambridge).

Whereas the transformation of dicotyledonous plants by Ti-plasmid-vector systems by means of *Agrobacterium tumefaciens* is a well-established method, more recent studies indicate that the transformation with vectors based on *Agrobacterium* can also be used in the case of monocotyledonous plants (Chan et al., Plant Mol. Biol. 22 (1993), 491–506; Hiei et al., Plant J. 6 (1994), 271–282).

Alternative systems for the transformation of monocotyledonous plants are the transformation by means of the biolistic approach, protoplast transformation, electroporation of partially permeablized cells, the introduction of DNA by means of glass fibers.

There are various references in the relevant literature dealing specifically with the transformation of maize (cf. e.g. WO95/06128, EP 0 513 849; EP 0 465 875). In EP 292 435 a method is described by means of which fertile plants may be obtained starting from mucousless, friable granulous maize callus. In this context it was furthermore observed by Shillito et al. (Bio/Technology 7 (1989), 581) that for regenerating fertile plants it is necessary to start from callus-suspension cultures from which a culture of dividing protoplasts can be produced which is capable to regenerate to plants. After an in vitro cultivation period of 7 to 8 months Shillito et al. obtain plants with viable descendants which, however, exhibited abnormalities in morphology and reproductivity.

Prioli and Söndahl (Bio/Technology 7 (1989), 589) have described how to regenerate and to obtain fertile plants from maize protoplasts of the Cateto maize inbreed Cat 100–1. The authors assume that the regeneration of protoplast to fertile plants depends on a number of various factors such as the genotype, the physiological state of the donor-cell and the cultivation conditions. Once the introduced DNA has been integrated in the genome of the plant cell, it usually continues to be stable there and also remains within the descendants of the originally transformed cell. It usually contains a selectable marker which confers resistance against biozides or against an antibiotic such as kanamycin, G 418, bleomycin, hygromycin or phosphinotricine etc. to the transformed plant cells. The individually selected marker should therefore allow for a selection of transformed cells against cells lacking the introduced DNA.

The transformed cells grow in the usual way within the plant (see also McCormick et al., Plant Cell Reports 5 (1986), 81–84). The resulting plants can be cultivated in the usual way and cross-bred with plants having the same transformed genetic heritage or another genetic heritage. The resulting hybrid individuals have the corresponding phenotypic properties.

Two or more generations should be grown in order to ensure whether the phenotypic feature is kept stably and whether it is transferred. Furthermore, seeds should be harvested in order to ensure that the corresponding phenotype or other properties will remain.

Due to its properties the starch obtained from the plant cells or from the plants of the invention or obtainable by the processes of the invention is not only suitable for the specific purposes already mentioned herein, but also for various industrial uses.

Basically, starch can be subdivided into two major fields. One field comprises the hydrolysis products of starch and the so-called native starches. The hydrolysis products essentially comprise glucose and glucans components obtained by enzymatic or chemical processes. They can be used for further processes, such as fermentation and chemical modifications. In this context, it might be of importance that the hydrolysis process can be carried out simply and inexpensively. Currently, it is carried out substantially enzymatically using amyloglucosidase. It is thinkable that costs might be reduced by using lower amounts of enzymes for hydrolysis due to changes in the starch structure, e.g. increasing the surface of the grain, improved digestibility due to less branching or a steric structure, which limits the accessibility for the used enzymes.

The use of the so-called native starch which is used because of its polymer structure can be subdivided into two further areas:

(a) Use in Foodstuffs

Starch is a classic additive for various foodstuffs, in which it essentially serves the purpose of binding aqueous additives and/or causes an increased viscosity or an increased gel formation. Important characteristic properties are flowing and sorption behavior, swelling and pastification temperature, viscosity and thickening performance, solubility of the starch, transparency and paste structure, heat, shear and acid resistance, tendency to retrogradation, capability of film formation, resistance to freezing/thawing, digestibility as well as the capability of complex formation with e.g. inorganic or organic ions.

(b) Use in Non-Foodstuffs

The other major field of application is the use of starch as an adjuvant in various production processes or as an additive in technical products. The major fields of application for the use of starch as an adjuvant are, first of all, the paper and cardboard industry. In this field, the starch is mainly used for retention (holding back solids), for sizing filler and fine particles, as solidifying substance and for dehydration. In addition, the advantageous properties of starch with regard to stiffness, hardness, sound, grip, gloss, smoothness, tear strength as well as the surfaces are utilized.

Within the paper production process, a differentiation can be made between four fields of application, namely surface, coating, mass and spraying.

The requirements on starch with regard to surface treatment are essentially a high degree of brightness, corresponding viscosity, high viscosity stability, good film formation as well as low formation of dust. When used in coating the solid content, a corresponding viscosity, a high capability to bind as well as a high pigment affinity play an important role. As an additive to the mass rapid, uniform, loss-free dispersion, high mechanical stability and complete retention in the paper pulp are of importance. When using the starch in spraying, corresponding content of solids, high viscosity as well as high capability to bind are also significant.

A major field of application is, for instance, in the adhesive industry, where the fields of application are subdivided into four areas: the use as pure starch glue, the use in starch glues prepared with special chemicals, the use of starch as an additive to synthetic resins and polymer dispersions as well as the use of starches as extenders for synthetic adhesives. 90% of all starch-based adhesives are used in the production of corrugated board, paper sacks and bags, composite materials for paper and aluminum, boxes and wetting glue for envelopes, stamps, etc.

Another possible use as adjuvant and additive is in the production of textiles and textile care products. Within the textile industry, a differentiation can be made between the following four fields of application: the use of starch as a sizing agent, i.e. as an adjuvant for smoothing and strengthening the burring behavior for the protection against tensile forces active in weaving as well as for the increase of wear resistance during weaving, as an agent for textile improvement mainly after quality-deteriorating pretreatments, such as bleaching, dying, etc., as thickener in the production of dye pastes for the prevention of dye diffusion and as an additive for warping agents for sewing yarns.

Furthermore, starch may be used as an additive in building materials. One example is the production of gypsum plaster boards, in which the starch mixed in the thin plaster pastifies with the water, diffuses at the surface of the gypsum board and thus binds the cardboard to the board. Other fields of application are admixing it to plaster and mineral fibers. In ready-mixed concrete, starch may be used for the deceleration of the sizing process.

Furthermore, the starch is advantageous for the production of means for ground stabilization used for the temporary protection of ground particles against water in artificial earth shifting. According to state-of-the-art knowledge, combination products consisting of starch and polymer emulsions can be considered to have the same erosion- and encrustation-reducing effect as the products used so far; however, they are considerably less expensive.

Another field of application is the use of starch in plant protectives for the modification of the specific properties of these preparations. For instance, starches are used for improving the wetting of plant protectives and fertilizers, for the dosed release of the active ingredients, for the conversion of liquid, volatile and/or odorous active ingredients into microcristalline, stable, deformable substances, for mixing incompatible compositions and for the prolongation of the duration of the effect due to a reduced disintegration.

Starch may also be used in the fields of drugs, medicine and in the cosmetics industry. In the pharmaceutical industry, the starch may be used as a binder for tablets or for the dilution of the binder in capsules. Furthermore, starch is suitable as disintegrant for tablets since, upon swallowing, it absorbs fluid and after a short time it swells so much that the active ingredient is released. For qualitative reasons, medicinal flowance and dusting powders are further fields of application. In the field of cosmetics, the starch may for example be used as a carrier of powder additives, such as scents and salicylic acid. A relatively extensive field of application for the starch is toothpaste.

The use of starch as an additive in coal and briquettes is also thinkable. By adding starch, coal can be quantitatively agglomerated and/or briquetted in high quality, thus preventing premature disintegration of the briquettes. Barbecue coal contains between 4 and 6% added starch, calorated coal between 0.1 and 0.5%. Furthermore, the starch is suitable as a binding agent since adding it to coal and briquette can considerably reduce the emission of toxic substances.

Furthermore, the starch may be used as a flocculant in the processing of ore and coal slurry.

Another field of application is the use as an additive to process materials in casting. For various casting processes cores produced from sands mixed with binding agents are needed. Nowadays, the most commonly used binding agent is bentonite mixed with modified starches, mostly swelling starches.

The purpose of adding starch is increased flow resistance as well as improved binding strength. Moreover, swelling starches may fulfill more prerequisites for the production process, such as dispersability in cold water, rehydratisability, good mixability in sand and high capability of binding water.

In the rubber industry starch may be used for improving the technical and optical quality. Reasons for this are improved surface gloss, grip and appearance. For this purpose, the starch is dispersed on the sticky rubberized surfaces of rubber substances before the cold vulcanization. It may also be used for improving the printability of rubber.

Another field of application for the modified starch is the production of leather substitutes.

In the plastics market the following fields of application are emerging: the integration of products derived from starch into the processing process (starch is only a filler, there is no direct bond between synthetic polymer and starch) or, alternatively, the integration of products derived from starch into the production of polymers (starch and polymer form a stable bond).

The use of the starch as a pure filler cannot compete with other substances such as talcum. This situation is different when the specific starch properties become effective and the property profile of the end products is thus clearly changed. One example is the use of starch products in the processing of thermoplastic materials, such as polyethylene. Thereby, starch and the synthetic polymer are combined in a ratio of 1:1 by means of coexpression to form a 'master batch', from which various products are produced by means of common techniques using granulated polyethylene. The integration of starch in polyethylene films may cause an increased substance permeability in hollow bodies, improved water vapor permeability, improved antistatic behavior, improved antiblock behavior as well as improved printability with aqueous dyes. Another possibility is the use of the starch in polyurethane foams. Due to the adaptation of starch derivatives as well as due to the optimization of processing techniques, it is possible to specifically control the reaction between synthetic polymers and the starch's hydroxy groups. The results are polyurethane films having the following property profiles due to the use of starch: a reduced coefficient of thermal expansion, decreased shrinking behavior, improved pressure/tension behavior, increased water vapor permeability without a change in water acceptance, reduced flammability and cracking density, no drop off of combustible parts, no halides and reduced aging. Disadvantages that presently still exist are reduced pressure and impact strength.

Product development of film is not the only option. Also solid plastics products, such as pots, plates and bowls can be produced by means of a starch content of more than 50%. Furthermore, the starch/polymer mixtures offer the advantage that they are much easier biodegradable.

Furthermore, due to their extreme capability to bind water, starch graft polymers have gained utmost importance. These are products having a backbone of starch and a side lattice of a synthetic monomer grafted on according to the principle of radical chain mechanism. The starch graft polymers available nowadays are characterized by an improved binding and retaining capability of up to 1000 g water per g starch at a high viscosity. These super absorbers are used mainly in the hygiene field, e.g. in products such as diapers and sheets, as well as in the agricultural sector, e.g. in seed pellets.

What is decisive for the use of the new starch modified by recombinant DNA techniques are, on the one hand, structure, water content, protein content, lipid content, fiber content, ashes/phosphate content, amylose/amylopectin ratio, distribution of the relative molar mass, degree of branching, granule size and shape as well as crystallization, and on the other hand, the properties resulting in the following features: flow and sorption behavior, pastification temperature, viscosity, thickening performance, solubility, paste structure, transparency, heat, shear and acid resistance, tendency to retrogradation, capability of gel formation, resistance to freezing/thawing, capability of complex formation, iodine binding, film formation, adhesive strength, enzyme stability, digestibility and reactivity. The most remarkable feature is viscosity.

Moreover, the modified starch obtained from the plant cells of the invention may be subjected to further chemical modification, which will result in further improvement of the quality for certain of the above-described fields of application. These chemical modifications are principally known to the person skilled in the art. These are particularly modifications by means of acid treatment oxidation and esterification (formation of phosphate, nitrate, sulphate, xanthate, acetate and citrate starches. Further organic acids may also be used for esterification.)

formation of starch ethers (starch alkyl ether, O-allyl ether, hydroxylalkyl ether, O-carboxylmethyl ether, N-containing starch ethers, S-containing starch ethers)

formation of branched starches formation of starch graft polymers.

The invention also relates to propagation material of the plants of the invention, such as seeds, fruits, cuttings, tubers or root stocks, wherein this propagation material contains plant cells of the invention.

Deposits

The plasmids produced and/or used within the framework of the present invention have been deposited at the internationally acknowledged deposit "Deutsche Sammlung von Mikroorganismen (DSM)" in Braunschweig, Federal Republic of Germany, according to the requirements of the Budapest treaty for international acknowledgment of microorganism deposits for patenting (deposit number; deposition date):

| plasmid pBinAR Hyg | (DSM 9505) | (Oct. 20, 1994) |
| plasmid p33-anti-BE | (DSM 6146) | (Aug. 20, 1990) |
| plasmid pRL2 | (DSM 10225) | (Sep. 4, 1995) |

Plasmid structure:

A=fragment A: CaMV 35S promoter, nt 6909–7437 (Franck et al., Cell 21 (1980), 285–294)

B=fragment B: Asp718 fragment from pRL1 with a length of approximately 1949 bp

Orientation relative to the promoter: anti-sense

The arrow indicates the direction of the open reading frame.

C=fragment C: nt 11748–11939 of the T-DNA of Ti-plasmid pTiACH5 T-DNA (Gielen et al., EMBO J. 3 (1984), 835–846)

Figure 2:
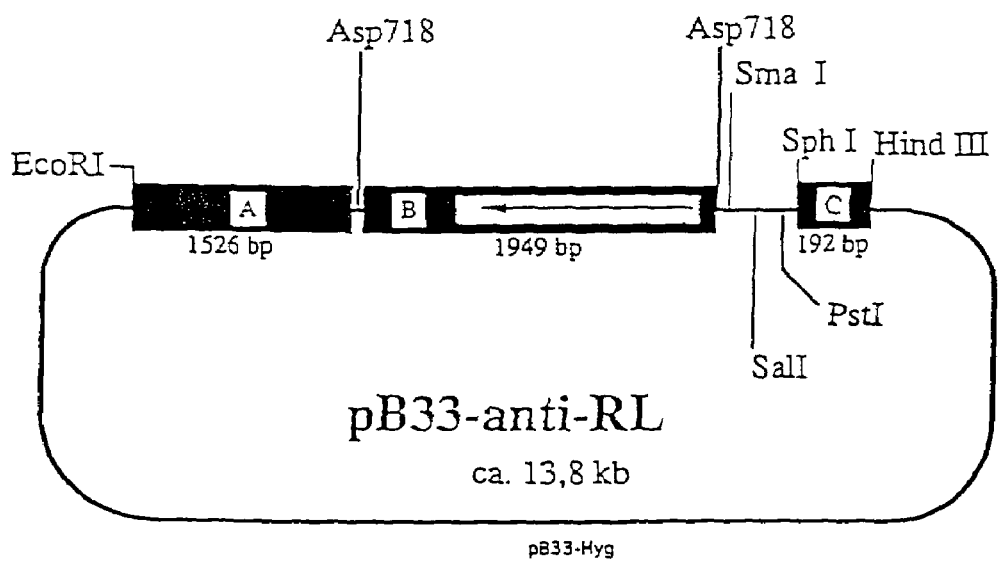

FIG. 2 shows the plasmid pB33-anti-RL

Plasmid structure:

A=fragment A: B33 promoter of the patatin gene B33 from *Solanum tuberosum* (Rocha-Sosa et al., EMBO J. 8 (1989), 23–29)

B=fragment B: Asp718 fragment from pRL1 with a length of approximately 1949 bp
Orientation relative to the promoter: anti-sense
The arrow indicates the direction of the open reading frame.
C=fragment C: nt 11748–11939 of the T-DNA of Ti-plasmid pTiACH5 T-DNA (Gielen et al., EMBO J. 3 (1984), 835–846)

Figure 3:
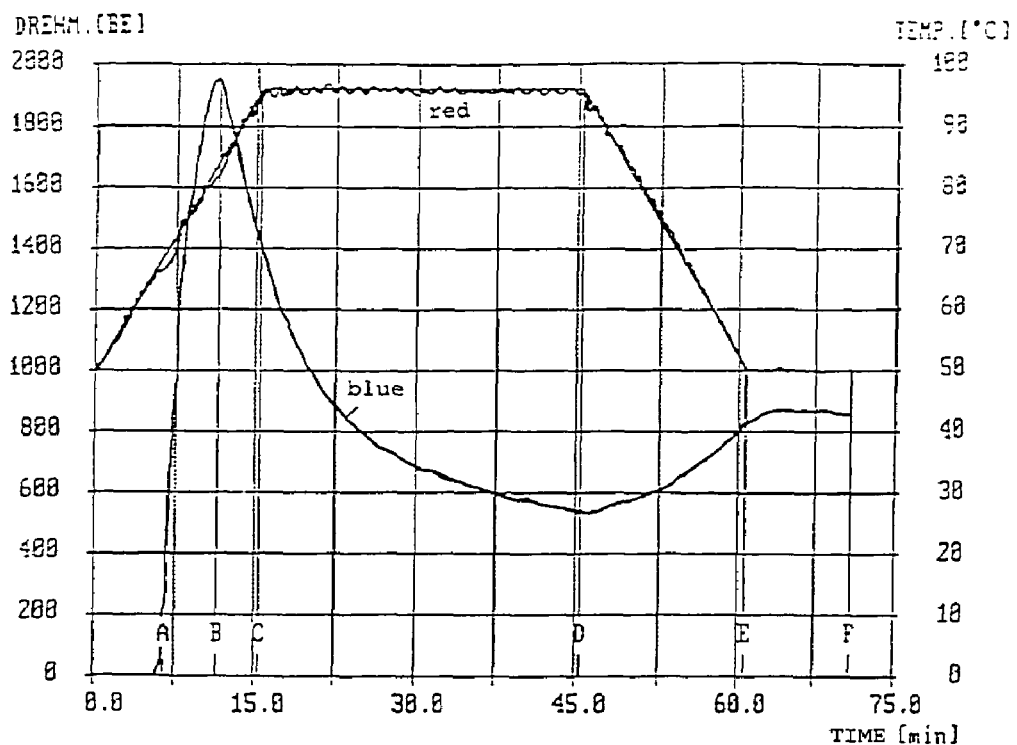

FIG. 3 shows a Brabender curve of a watery starch solution, recorded with a Viskograph-E-type Brabender viscograph, which was isolated from non-transformed potato plants of the variety Désirée (see also Example 8).

| Thereby signifying: | |
| --- | --- |
| Drehm. | torque |
| [BE] | Brabender unit |
| Temp. | temperature |
| A | start of pastification |
| B | maximum degree of viscosity |
| C | start of the 96° C.-period |
| D | start of cooling-off period |
| E | end of cooling-off period |
| F | end of the end-50° C. period |

The blue line indicates the viscosity; the red line stands for temperature.

Figure 4:
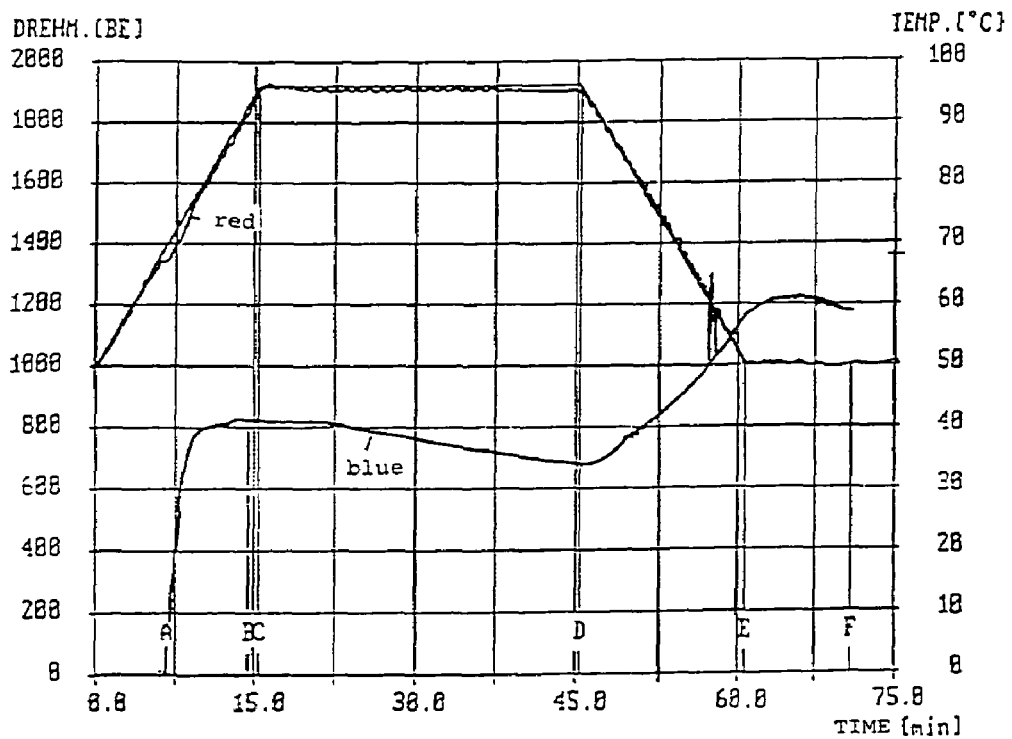

FIG. 4 shows a Brabender curve of a watery starch solution, recorded with a Viskograph-E-type Brabender viscograph, which was isolated from potato plants transformed with the plasmid p35S-anti-RL (see also Example 8). For the meaning of the abbreviations see FIG. 3.

Figure 5:
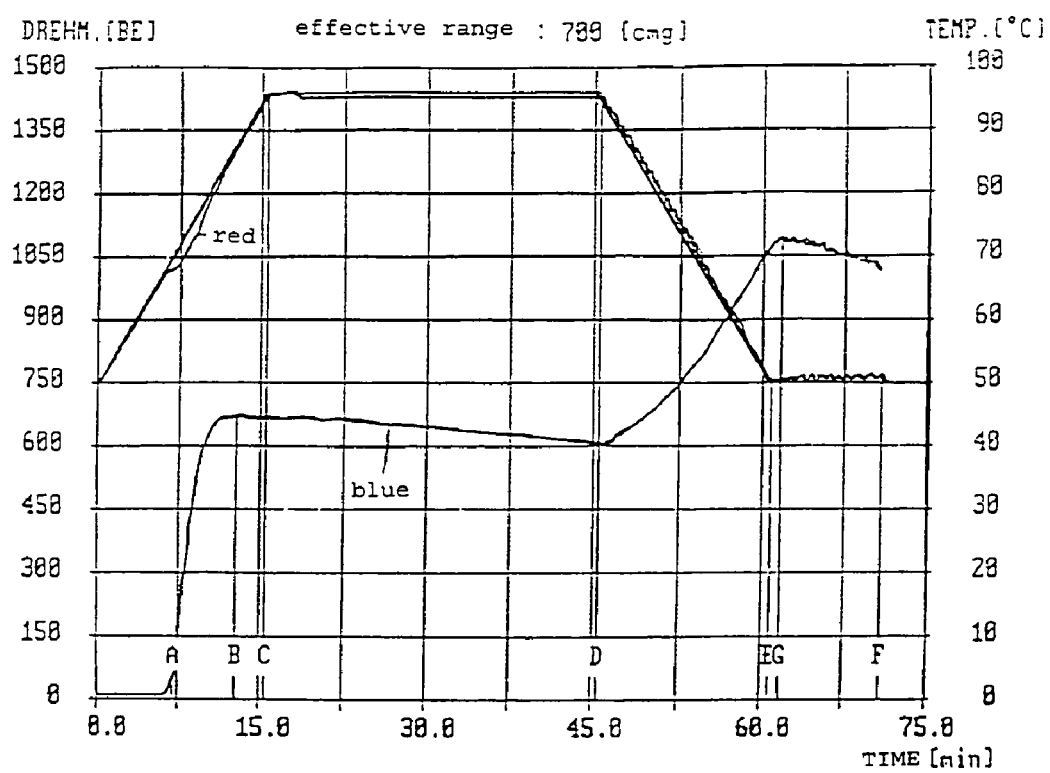

FIG. 5 shows a Brabender curve of a watery solution of starch from potatoes transformed with the plasmid pB33-anti-RL (see also Example 8), recorded with a Viskograph-E-type Brabender viscograph. For the meaning of the abbreviations see FIG. 3.

Figure 6:
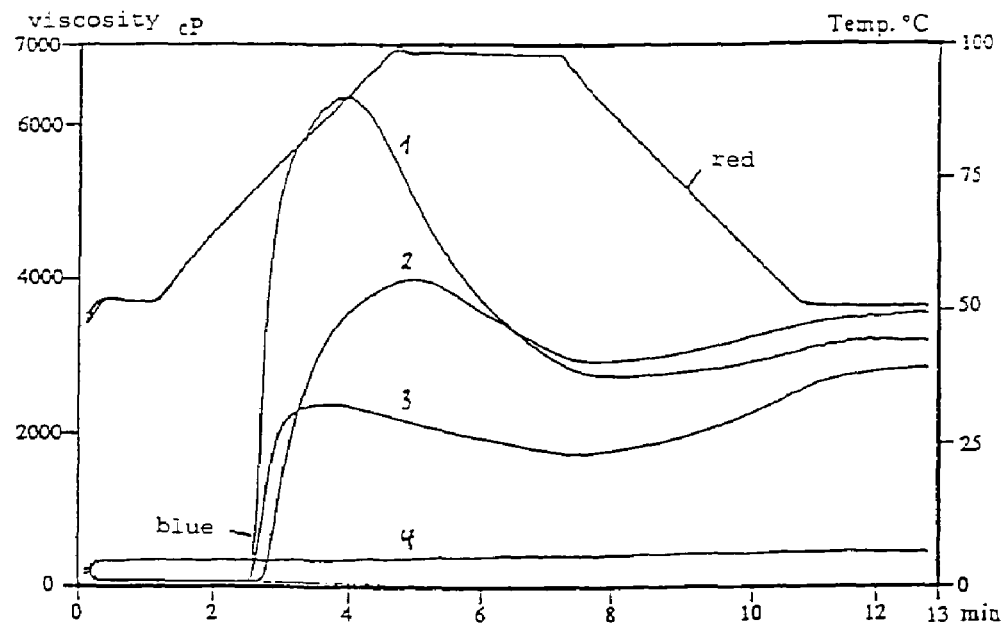

FIG. 6 shows curves of watery solutions of starch isolated from potato plants (see also Example 12), which were recorded with a Rapid Visco Analyser. The red line stands for the temperature; the blue lines 1, 2, 3 and 4 show the viscosities of the following starch solutions:
Line 1: starch isolated from wildtype plants,
Line 2: starch isolated from plants in which only the branching enzyme was inhibited (cf. Example 1 of patent application WO92/14827),
Line 3: starch isolated from plants in which merely the concentration of the proteins of the invention had been reduced (cf. Example 6).
Line 4: starch isolated from plants which had been transformed with the plasmid p35S-anti-RL in combination with the p35SH-anti-BE plasmid (cf. Example 12).

Figure 7:
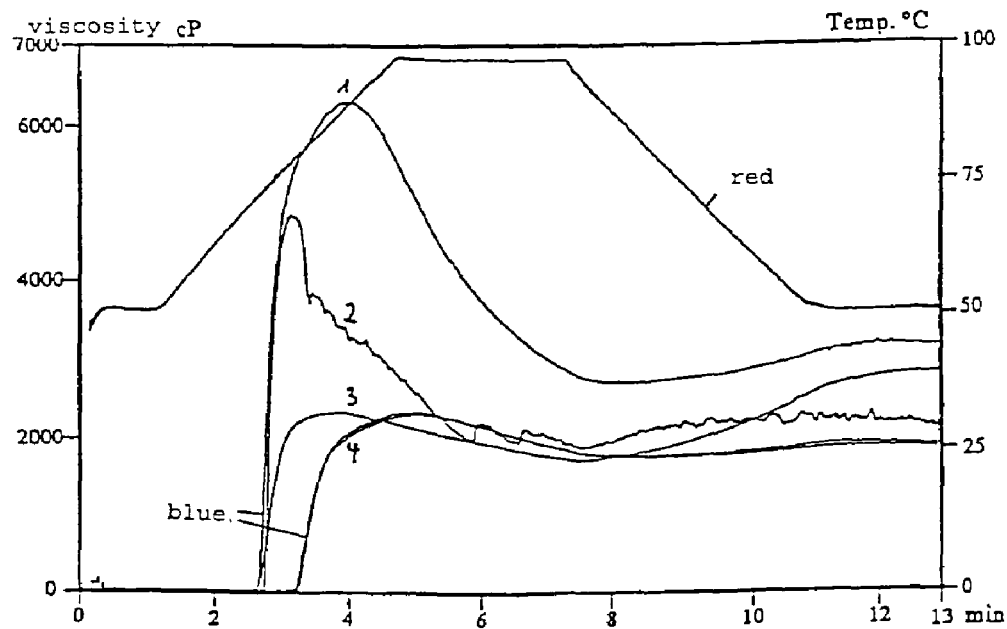

FIG. 7 shows curves of watery solutions of starch isolated from potato plants (see also Example 13), which were recorded with a Rapid Visco Analyser. The red line stands for the temperature; the blue lines 1, 2, 3 and 4 show the viscosities of the following starch solutions:
Line 1: starch isolated from wildtype plants,
Line 2: starch isolated from plants which had solely been transformed with the plasmid pB33-anti-GBSSI (so-called waxy-potato),
Line 3: starch isolated from plants which had been solely transformed with the plasmid p35S-anti-RL (cf. Example 6).
Line 4: starch isolated from plants which had been transformed with the plasmid pB33-anti-RL in combination with the plasmid pB33-anti-GBSSI (cf. Example 13).

Figure 8:
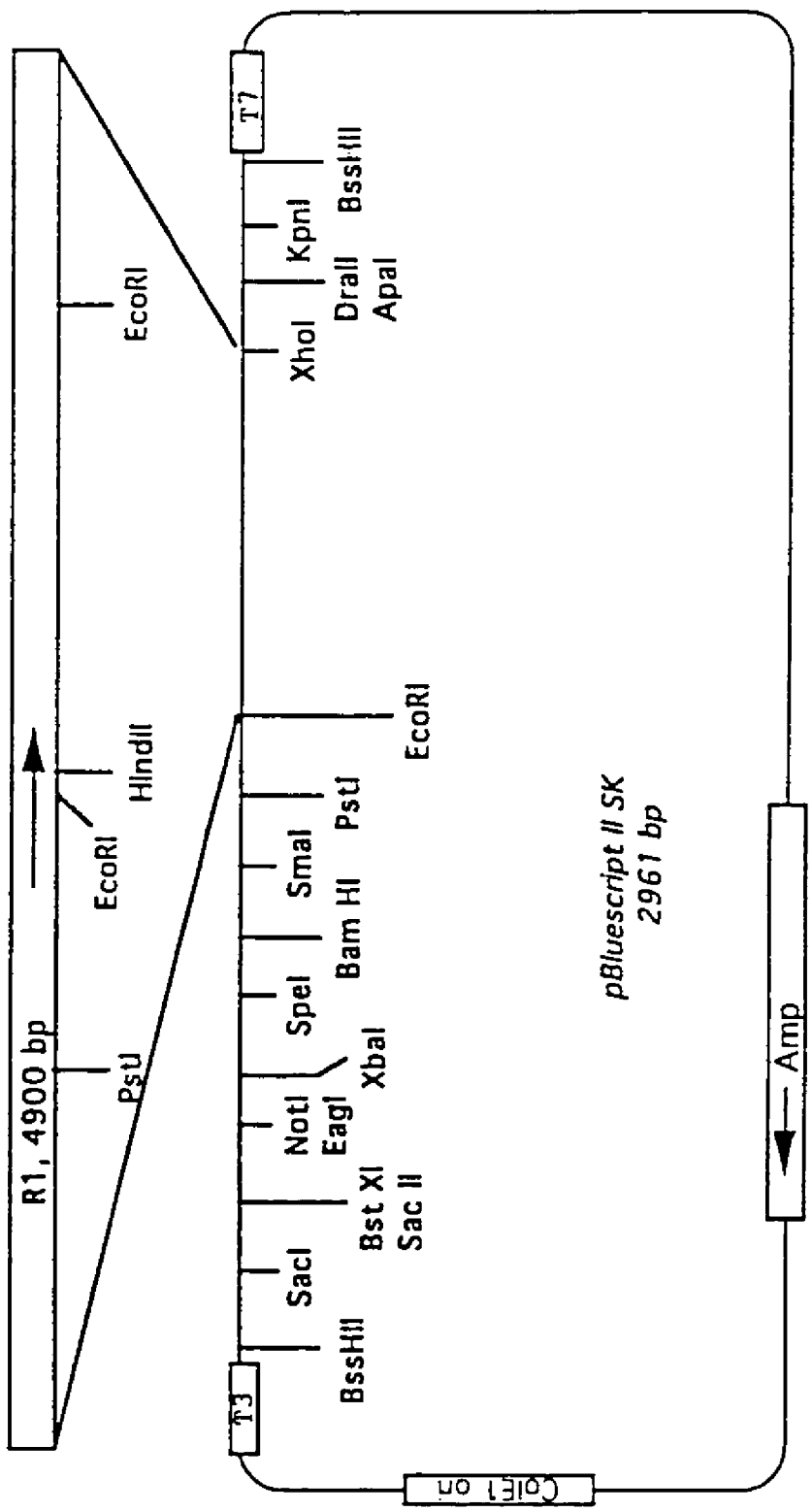

FIG. 8 shows the pRL2 plasmid which comprises a full-length cDNA from potato encoding an R1 enzyme.

The Examples illustrate the invention.

Used Media and Solutions

Elution buffer:
    25 mM Tris pH 8,3
    250 mM glycine
Dialysis buffer:
    50 mM Tris-HCl pH 7,0
    50 mM NaCl
    2 mM EDTA
    14,7 mM β-mercaptoethanol
    0,5 mM PMSF
Protein buffer:
    50 mM sodium phosphate buffer pH 7,2
    10 mM EDTA
    0,5 mM PMSF
    14,7 mM β-mercaptoethanol
Lugol solution:
    12 g KI
    6 g $I_2$
        ad 1,8 l with $ddH_2O$
20×SSC:
    175.3 g NaCl
    99.2 g sodium citrate
        ad 1000 ml with $ddH_2O$
        ph 7,0 with 10 N NaOH
10×MEN:
    200 mM MOPS
    50 mM sodium acetate
    10 mM EDTA
    pH 7,0
NSEB buffer:
    0,25 M sodium phosphate buffer pH 7,2
    7% SDS
    1 mM EDTA
    1% BSA (w/v)
YT
    8 g Bacto-Yeast extract
    5 g Bacto-Tryptone
    5 g NaCl
        ad 1000 ml with $ddH_2O$
Protoplast Isolation Medium (100 ml)
Cellulase Onozuka R S (Meiji Seika, Japan) 800 mg
Pectolyase Y 23 40 mg
$KNO_3$ 200 mg
$KH_2PO_4$ 136 mg
$K_2HPO_4$ 47 mg
$CaCl_2$ $2H_2O$ 147 mg
$MgSO_4$ $7H_2O$ 250 mg
Bovine serum albumine (BSA) 20 mg
Glucose 4000 mg
Fructose 4000 mg
Sucrose 1000 mg
pH 5,8
Osmolarity 660 mosm.
Protoplast washing solution 1: like protoplast isolating solution, but without cellulase, pectolyase and BSA
Transformation Buffers:
a) Glucose 0,5 M
    MES 0,1%
    $MgCl_2$ $6H_2O$ 25 mM
    pH 5,8
    adjust to 600 mosm.

b) PEG 6000-solution
   Glucose 0,5 M
   MgCl$_2$ 6H$_2$O 100 mM
   Hepes 20 mM
   pH 6,5

PEG 6000 is added to the buffer described in b) immediately prior to the use of the solution (40% w/v PEG). The solution is filtered with a 0,45 μm sterile filter.

W5 Solution
   CaCl$_2$ 125 mM
   NaCl 150 mM
   KCl 5 mM
   Glucose 50 mM
   Protoplast Culture Medium (Indicated in mg/l)
   KNO$_3$ 3000
   (NH$_4$)$_2$SO$_4$ 500
   MgSO$_4$ 7H$_2$O 350
   KH$_2$PO$_4$ 400
   CaCl$_2$ 2H$_2$O 300
   Fe-EDTA and trace elements as in the Murashige-Skoog medium (Physiol. Plant, 15 (1962), 473).
   m-inosite 100
   Thiamine HCl 1,0
   Nicotine acid amide 0,5
   Pyridoxine HCl 0,5
   Glycine 2,0
   Glucuronic acid 750
   Galacturonic acid 750
   Galactose 500
   Maltose 500
   Glucose 36.000
   Fructose 36.000
   Sucrose 30.000
   Asparagine 500
   Glutamine 100
   Proline 300
   Caseinhydrolysate 500
   2,4 dichlorophenoxy acetic acid (2,4-D) 0,5
   pH 5,8
   Osmolarity 600 mosm.
   Buffer A
     2× SSC
     10× Denhardts solution
     0,1 % SDS
     5 mM EDTA
     50 mM disodium phosphate
     250 μg/ml herring sperm DNA In the example the following standard methods were used:

1. Cloning
   For cloning in *E. coli* the vector pBluescriptSK was used.
   For plant transformation the gene constructs were cloned into the binary vector pBinAR (Höfgen and Willmitzer, Plant Sci. 66 (1990), 221–230) and B33-Hyg.

2. Bacterial strains
   For the Bluescript vector and for the pBinAR and B33-Hyg constructs use was made of the *E. coli* strain DH5α (Bethesda Research Laboratories, Gaithersburgh, USA).
   The transformation of plasmid in potato plants was carried out by means of the *Agrobacterium tumefaciens* strain C58C1 pGV2260 (Deblaere et al., Nucl. Acids Res. 13 (1985), 4777:4788).

3. Transformation of *Agrobacterium tumefaciens*
   The DNA transfer was carried out by means of direct transformation according to the method of Höfgen & Willmitzer (Nucleic Acids Res. 16 (1988), 9877). The plasmid DNA of transformed *Agrobacteria* was isolated according to the method of Birnboim & Doly (Nucleic Acids Res. 7 (1979), 1513–1523) and electrophoretically analyzed after suitable restriction cleavage.

4. Transformation of Potatoes
   Ten small leaves of a sterile potato culture (*Solanum tuberosum* L. cv. Désirée) injured by a scalpel were treated with 10 ml MS medium (Murashige & Skoog, Physiol. Plant. 15 (1962), 473–497) with 2% sucrose. The medium contained 50 μl of a *Agrobacterium tumefaciens* overnight-culture grown under selection. After slightly shaking it for 3–5 minutes, another incubation took place in darkness for two days. The leaves were subsequently put on MS medium with 1,6% glucose, 5 mg/l naphtyle acetic acid, 0,2 mg/l benzylaminopurine, 250 mg/l claforan, 50 mg/l kanamycin or 1 mg/l hygromycin B, and 0,80% Bacto Agar for callus induction. After a one-week incubation at 25° C. and 3000 lux the leaves were put on MS-medium with 1,6% glucose, 1,4 mg/l zeatine ribose, 20 mg/l naphtyle acetic acid, 20 mg/l giberellic acid, 250 mg/l claforan, 50 mg/l kanamycin or 3 mg/l hygromycin B and 0,80% Bacto Agar for shoot induction.

5. Transformation of Maize
   (a) Production of Protoplasts of the Cell Line DSM 6009
   Protoplast Isolation
   2–4 days, preferably 3 days after the last change of medium in a protoplast suspension culture the liquid medium is pumped off and the remaining cells are washed in 50 ml protoplast washing solution 1 and sucked dry once more. 10 ml protoplast isolation medium are added to 2 g of harvested cell mass. The resuspended cells and cell aggregates are incubated at 27±2° C. for 4 to 6 hours in the darkness, while shaking it slightly (at 30 to 40 rpm).
   Protoplast Purification
   As soon as the release of at least 1 million protoplasts/ml has taken place (microscopic inspection), the suspension is sifted through a stainless steel or nylon sieve with a mesh size of 200 or 45 μm. The combination of a 100 μm and a 60 μm sieve allows for separating the cell aggregates just as well. The protoplast-containing filtrate is examined microscopically. It usually contains 98–99% protoplasts. The rest are undigested single cells. Protoplast preparations with such a degree of purity are used for transformation experiments without additional gradient centrifugation. The protoplasts are sedimented by means of centrifugation (100 UpM in the swing-out rotor (100×g, 3 minutes)). The supernatant is abandoned and the protoplasts are resuspended in washing solution 1. The centrifugation is repeated and the protoplasts are subsequently resuspended in the transformation buffer.
   (b) Protoplast Transformation
   The protoplasts resuspended in the transformation buffer are filled in 10 ml portions into 50 ml polyallomer tubes at a titer of 0.5–1×10$^6$ protoplasts/ml. The DNA used for transformation is dissolved in Tris-EDTA (TE) buffer solution. 20 μg plasmid DNA is added to each ml protoplast suspension. A plasmid which provides for resistance to phosphinotricine is used as vector (cf. e.g. EP 0 513 849). After the addition of DNA the protoplast suspension is carefully shaken in order to homogenously distribute the DNA in the solution. Immediately afterwards 5 ml PEG solution is added in drops.

By carefully shaking the tubes the PEG solution is distributed homogenously. Afterwards further 5 ml of PEG solution are added and the homogenous mixing is repeated. The protoplasts remain in the PEG solution for 20 minutes at ±2° C. Afterwards the protoplasts are sedimented by centrifuging for 3 minutes (100 g; 1000 Upm). The supernatant is abandoned. The protoplasts are washed in 20 ml W5 solution by careful shaking and are again subjected to centrifugation. Then they are resuspended in 20 ml protoplast culture medium, centrifuged anew and again resuspended in culture medium. The titer is adjusted to $6-8 \times 10^5$ protoplasts and the protoplasts are cultivated in 3 ml portions in Petri dishes (Ø 60 mm, height 15 mm). The Petri dishes are sealed with parafilm and stored in darkness at 25±2° C.

(c) Protoplast Culture

During the first 2–3 weeks after the protoplast isolation and transformation the protoplasts are cultivated without adding fresh medium. As soon as the cells regenerated from the protoplasts have developed into cell aggregates with more than 20 to 50 cells, 1 ml of fresh protoplast culture medium, containing sucrose as an osmotic (90 g/l), is added.

(d) Selection of Transformed Maize Cells and Plant Regeneration

3–10 days after adding fresh medium the cell aggregates developed from the protoplasts may be plated on Agar media with 100 mg/l L-phosphinothricine. N6-medium with the vitamins of the protoplast culture medium, 90 g/l sucrose and 1.0 mg/l 2.4D is as suitable as an analogous medium such as a medium with the macro- and micro-nutritive salts of the MS medium (Murashige and Skoog (1962), see above).

The calli developed from stably transformed protoplasts may grow further on the selective medium. After 3 to 5 weeks, preferably 4 weeks the transgenic calli may be transferred to fresh selection medium which also contains 100 mg/l L-phosphinothricine which, however, does no longer contain auxine. Within 3 to 5 weeks approximately 50% of the transgenic maize calli which had integrated the L-phosphinothricine-acetyl-transferase gene into their genome, start to differentiate into plants on this medium in the presence of L-phosphinothricine.

(e) Growing of Transgenic Regenerative Plants

The embryogenical transformed maize tissue is cultivated on hormone-free N6-medium (Chu C. C. et al., Sci. Sin. 16 (1975), 659) in the presence of $5 \times 10^{-4}$ M L-phosphinothricine. On this medium maize embryos, which express the phosphinothricine-acetyl-transferase gene (PAT gene) in a sufficiently strong manner, develop into plants. Non-transformed embryos or such with only a very weak PAT activity die down. As soon as the leaves of the in-vitro plants have reached a length of 4 to 6 mm, they may be transferred into soil. After washing off the Agar residues at the roots the plants are planted into a mixture of clay, sand, vermiculite and potting soil with the ratio 3:1:1:1 and adapted to the soil culture at 90–100% of relative atmospheric humidity during the first 3 days after planting. The growing is carried out in a climate chamber with a 14 hour light period of approximately 25000 lux at the height of the plant at a day/night temperature of 23±1/17 ±1° C. The adapted plants are cultivated at an 65±5% atmospheric humidity.

6. Radioactive Marking of DNA Fragments

The radioactive marking of DNA fragments was carried out by means of a DNA-Random Primer Labeling Kits by Boehringer (Germany) according to the manufacturer's instructions.

7. Northern Blot Analysis

RNA was isolated from leave tissue according to standard protocols. 50 μg of the RNA was separated on an agarose gel (1.5% agarose, 1×MEN buffer, 16.6% formaldehyde). After the gel run the gel was briefly washed in water. The RNA was transferred to a Hybond N type nylon membrane (Amersham, UK) with 20×SSC by means of capillary blot. The membrane was subsequently baked in vacuum for two hours at 80° C.

The membrane was prehybridized in NSEB buffer for two hours at 68° C. and subsequently hybridized overnight in NSEB buffer in the presence of the radioactively marked probe at 68° C.

8. Plant Maintenance

Potato plants were kept in the greenhouse under the following conditions:

light period 16 hours at 25000 lux and 22° C.

dark period 8 hours at 15° C.

atmospheric humidity 60%

9. Determination of the Amylose/Amylopectin Ratio in Starch Obtained from Potato Plants Starch was isolated from potato plants according to standard methods and the amylose/amylopectin ratio was determined according to the method described by Hovenkamp-Hermelink et al. (Potato Research 31 (1988) 241–246).

10. Determination of Glucose, Fructose and Sucrose

In order to determine the glucose, fructose and/or sucrose content, small pieces of potato tubers (with a diameter of approx. 10 mm) are frozen in liquid nitrogen and subsequently extracted for 30 min at 80° C. in 0.5 ml 10 mM HEPES, pH 7.5; 80% (vol./vol.) ethanol. The supernatant containing the soluble components is withdrawn and the volume is determined. The supernatant is used for determining the amount of soluble sugars. The quantitative determination of soluble glucose, fructose and sucrose is carried out in a reaction mixture with the following composition:

100.0 mM imidazole/HCl, pH 6.9

1.5 mM $MgCl_2$ 0.5 mM $NADP^+$ 1.3 mM ATP

10–50 μl sample 1.0 U glucose-6-phosphate dehydrogenase from yeast

The reaction mixture is incubated at room temperature for 5 minutes. The subsequent determination of sugars is carried out by means of standard photometric methods by measuring the absorption at 340 nm after successive adding of 1.0 unit of hexokinase from yeast (for determining glucose)

1.0 unit of phosphoglucoisomerase from yeast (for determining fructose)

and 1.0 unit of invertase from yeast
(for determining sucrose).

EXAMPLE 1

The Isolation of Starch Granule-Bound Proteins from Potato Starch

The isolation of starch granule-bound proteins from potato starch is carried out by means of electroelution in an elution appliance which was constructed analogous to the "Model 442 Electro Eluter" (BIORAD Laboratories Inc., USA) but had a considerably greater volume (approx. 200 ml). 25 g dried starch were dissolved in elution buffer (final volume 80 ml). The starch was derived from potatoes which produce an almost amylose-free starch due to the antisense-expression of a DNA sequence encoding the starch granule-bound starch synthases I (GBSS I) from potato. The suspension was heated to 70–80° C. in a water bath. Subsequently 72.07 g urea was added (end concentration 8 M) and the volume was filled up to 180 ml with elution buffer. The starch dissolved during permanent stirring and acquired a paste-like consistency. The proteins were electroeluted from the solution overnight by means of the elution appliance (100 V; 50–60 mA). The eluted proteins were carefully removed from the appliance. Suspended particles were removed in a brief centrifugation. The supernatant was dialyzed at 4° C. 2 to 3 times for one hour against dialysis buffer. Subsequently, the volume of the protein solution was determined. The proteins were precipitated by adding ammonium sulfate (final concentration 90%), which was done during permanent stirring at 0° C. The precipitated proteins were pelleted by centrifugation and resuspended in protein buffer.

EXAMPLE 2

Identification and Isolation of cDNA Sequences Encoding Starch Granule-Bound Proteins The proteins isolated according to Example 1 were used for the production of polyclonal antibodies from rabbit, which specifically recognize starch granule-bound proteins.

By means of such antibodies a cDNA expression library was subsequently screened for sequences encoding starch granule-bound proteins, using standard methods.

The expression library was produced as follows:

Poly (A$^+$)-mRNA was isolated from potato tubers of the "Berolina" variety. Starting from the poly (A$^+$)-mRNA, cDNA was produced according to the Gubler and Hoffmann method (Gene 25 (1983), 263–269), using an Xho I-Oligo d(t)18 primer. This cDNA was cut with Xho I after EcoR I-linker addition and ligated in an oriented manner in a lambda ZAP II vector (Stratagene) cut with EcoR I and Xho I. Approximately 500,000 plaques of a cDNA library constructed in such a way were screened for sequences which were recognized by polyclonal antibodies directed against starch granule-bound proteins.

In order to analyze the phage plaques these were transferred to nitrocellulose filters which had previously been incubated in a 10 mM IPTG solution for 30 to 60 minutes and had subsequently been dried on filter paper. The transfer took place at 37° C. for 3 hours. Subsequently, the filters are incubated at room temperature for 30 minutes in block reagent and washed for 5–10 minutes in TBST buffer. The filters were shaken with the polyclonal antibodies directed against starch granule-bound proteins in a suitable dilution for one hour at room temperature or for 16 hours at 4° C. The identification of plaques expressing a protein which was recognized by the polyclonal antibodies was carried out by means of the "Blotting detection kit for rabbit antibodies RPN 23" (Amersham UK) according to the manufacturer's instructions.

Phage clones of the cDNA library expressing a protein which was recognized by the polyclonal antibodies were further purified by using standard methods.

By means of the in-vivo excision method, E. coli clones were obtained from positive phage clones containing a double-stranded pBluescript plasmid with the corresponding cDNA insertion. After checking the size and the restriction pattern of the insertions a suitable clone, pRL1, was further analyzed.

EXAMPLE 3

Sequence Analysis of the cDNA Insertion of the Plasmid pRL1

From an E. coli clone obtained according to Example 2 the plasmid pRL1 was isolated and a part of the sequence of its cDNA insertion was determined by standard procedures using the didesoxynucleotide method (Sanger et al., Proc. Natl. Acad. Sci. USA 74 (1977), 5463–5467). The insertion has a length of about 2450 bp. A part of the nucleotide sequence as well as the amino acid sequence derived therefrom is indicated under Seq ID No. 3 and under Seq ID No. 4.

A sequence analysis and a sequence comparison with known DNA sequences showed that the sequence indicated under Seq ID No. 3 is new and exhibits no significant homology to DNA sequences known so far. Moreover, the sequence analysis showed that the cDNA insertion is only a partial cDNA in which a part of the coding region at the 5'-end is missing.

EXAMPLE 4

Identification and Isolation of a Complete cDNA Encoding a Starch Granule-Bound Protein from *Solanum tuberosum*

In order to isolate a complete cDNA corresponding to the partial cDNA insertion of the plasmid pRL1, a further cDNA library was produced. This was a guard-cell-specific cDNA library from *Solanum tuberosum* which was constructed as follows:

At first epidermis fragments from leaves of "Desirée" variety potato plants were produced essentially according to the Hedrich et al. method (Plant Physiol. 89 (1989), 148), by harvesting approximately 60 leaves of six-weeks-old potato plants kept in the greenhouse. The center nerve was removed from the leaves. The leaves were subsequently crushed in a big "Waring blender" (with a volume of 1 liter) four times in cooled, distilled $H_2O$ on the highest level for 15 seconds each. The suspension was filtered through a nylon sieve with a mesh size of 220 μm (Nybolt, Zurich, Switzerland) and washed in cold distilled water several times. The suspension itself was filtered through a 220 μm nylon sieve and intensely washed with cold distilled water. The residues (epidermis fragments) were crushed in a smaller "Waring blender" (with a volume of 250 ml) four times in distilled water and ice on a lower level for 15 seconds each. The suspension was filtered through a 220 µm nylon sieve and washed intensely with cold distilled water. The epidermis fragments (residues) were microscopically examined for contamination by mesophyl cells. If contamination occurred the crushing step was repeated in a small "Waring blender". The disruption of the guard cells of the epidermis fragments was carried out by means of pulverizing in liquid nitrogen in a cooled mortar for approximately two hours. In order to examine the disruption of the guard cells, probes were regularly taken and microscopically examined. After two hours, or if a sufficiently high amount of guard cells had been disrupted, the obtained powder was filled into a reaction tube (with a volume of 50 ml) and resuspended in one volume GTC buffer (Chirgwin et al., Biochem. 18 (1979), 5294–5299). The suspension was centrifuged and the supernatant was filtered through Miracloth (Calbiochem, La Jolla, Calif.). The filtrate was subjected to ultracentrifugation for 16 hours, as described in Glisin et al. (Biochemistry 13 (1974), 2633–2637) and Mornex et al. (J. Clin. Inves. 77 (1986), 1952–1961). After the centrifugation the RNA precipitate was dissolved in 250 µl GTC buffer. The RNA was precipitated by adding 0.05 volumes of 1 M acetic acid and 0.7 volumes of ethanol. The RNA was precipitated by centrifugation and the precipitate was washed with 3 M sodium acetate (pH 4.8) and 70% ethanol. The RNA was briefly dried and dissolved in DEPC treated water.

Poly $A^+$-RNA was isolated from the isolated RNA according to standard methods. Starting from the poly($A^+$)-mRNA, cDNA was produced according to the Gubler and Hoffmann method (Gene 25 (1983), 263–269) by means of a Xho I-oligo $d(t)_{18}$ primer. This cDNA was cut with Xho I after EcoR I-linker addition and ligated in an oriented manner in a lambda ZAP II vector (Stratagene GmbH, Heidelberg, Germany) cut with EcoR I and Xho I. The packaging in phage heads was carried out using the Gigapack II Gold kit (Stratagene GmbH, Heidelberg, Germany) according to the manufacturer's instructions.

From such a cDNA library phage clones hybridizing with the cDNA insertion of the pRL1 plasmid were isolated and purified according to standard methods. By means of the in vivo excision method *E. coli* clones were obtained from positive phage clones containing a double-stranded pBluescript plasmid with the corresponding cDNA insertion. After checking the size and the restriction pattern of the insertions, suitable clones were subjected to restriction mapping and sequence analysis. From a suitable clone the plasmid pRL2 (DSM 10225) was isolated which contains a complete cDNA which encodes a starch granule-bound protein from potato.

EXAMPLE 5

Sequence Analysis of the cDNA Insertion of the pRL2 Plasmid

The nucleotide sequence of the cDNA insertion of the pRL2 plasmid was determined as described in Example 3. The insertion has a length of 4856 bp. The nucleotide sequence as well as the amino acid sequence derived therefrom is indicated in Seq ID No. 1 and/or Seq ID No. 2. In the following, the corresponding gene will be called RL-gene. The protein encoded by the coding region will be called R1 enzyme.

EXAMPLE 6

The Construction of the Plasmid p35S-anti-RL and the Introduction of the Plasmid into the Genome of Potato Plants By means of the restriction endonuclease Asp718 a DNA fragment with an approximate length of 1800 bp was isolated from the pRL1 plasmid. This corresponds to the DNA sequence indicated under Seq ID No. 3 and contains a part of the open reading frame. The fragment was ligated into the binary vector pBinAR cut with Asp718 (Höfgen and Willmitzer, Plant Sci. 66 (1990), 221–230). This is a derivative of the binary vector pBin19 (Bevan, Nucl. Acids Res. 12 (1984), 8711–8721). pBinAR was constructed as follows:

A fragment with a length of 529 bp comprising the nucleotides 6909–7437 of the 35S promoter of the cauliflower-mosaic virus (Franck et al., Cell 21 (1980), 285–294) was isolated from the plasmid pDH51 (Pietrzak et al., Nucl. Acids Res. 14, 5857–5868) as an EcoR I/Kpn I fragment and ligated between the EcoR I and the Kpn I sites of the pBin19 polylinker. This led to the plasmid pBin19-A.

Figure 1:
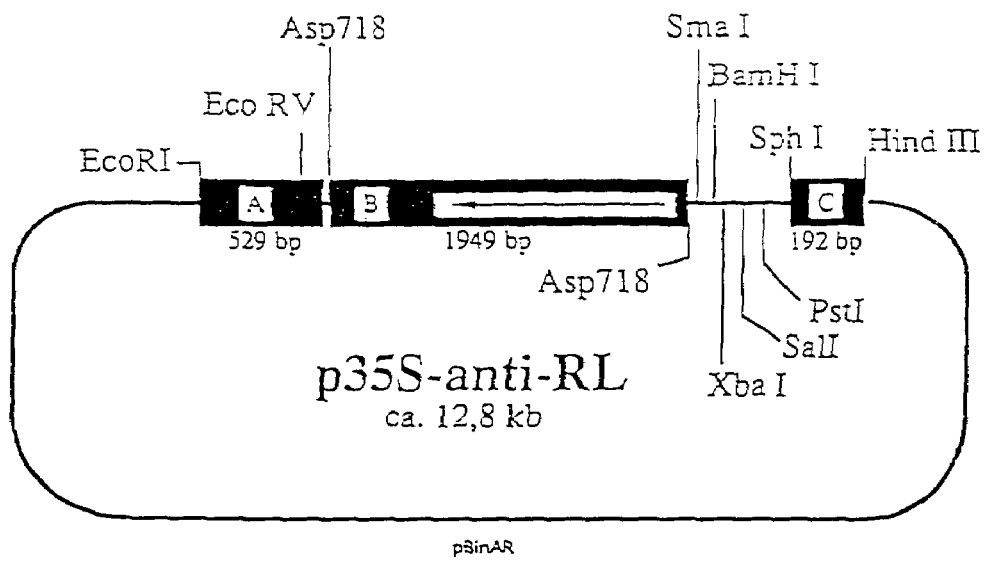
FIG. 1 shows the plasmid p35S-anti-RL.

By means of the restriction endonucleases Pvu II and Hind III a fragment with a length of 192 bp was isolated from the plasmid pAGV40 (Herrera-Estrella et al., Nature 303, 209–213) comprising the polyadenylation signal of gene 3 of the T-DNA of the Ti-plasmid pTiACH5 (Gielen et al., EMBO J. 3, 835–846) (nucleotides 11749–11939). After the addition of Sph I-linkers to the Pvu I site the fragment was ligated between the Sph I and Hind III sites of pBin19-A. This led to plasmid pBinAR. By means of restriction and sequence analysis recombinant vectors were identified in which the DNA fragment is inserted in the vector in such a way that a part of the coding region of the cDNA insertion from pRL1 is linked with the 35S promoter in antisense orientation. The resulting plasmid p35S-anti-RL is shown in FIG. 1.

By inserting the cDNA fragment an expression cassette is produced which consists of the fragments A, B and C:

Fragment A (529 bp) contains the 35S promoter of the cauliflower-mosaic virus (CaMV). The fragment comprises the nucleotides 6909 to 7437 of the CaMV (Franck et al., Cell 21 (1980), 285–294).

Apart from flanking regions, fragment B contains a part of the protein encoding cDNA insertion from plasmid pRL1. This was isolated as an Asp718 fragment of pRL1 as described above and fused to the 35S promoter in antisense orientation.

Fragment C (192 bp) contains the polyadenylation signal of gene 3 of the T-DNA of the Ti-plasmid pTiACH5 (Gielen et al., EMBO J. 3 (1984), 835–846).

The plasmid p35S-anti-RL has a size of approximately 12.8 kb.

The plasmid was transferred into potato plants by means of *Agrobacteria*-mediated transformation, as described above. From the transformed cells whole plants were regenerated. The transformed plants were cultivated under greenhouse conditions. By analyzing total RNA in a Northern Blot analysis concerning the disappearance of the transcripts complementary to the cDNA, the success of the genetic modification of the plants was assessed. For this purpose, total RNA was isolated from leaves of transformed plants according to standard methods and subsequently separated electrophoretically on an agarose gel. Then it was transferred onto a nylon membrane and hybridized with a radioactively labelled probe having the sequence indicated under Seq ID No. 1 or a part thereof. In about 5–10% of the transformed plants the band indicating the specific transcript under Seq ID No. 1 was missing in the Northern Blot Analysis. The plants were used for analyzing the starch quality.

EXAMPLE 7

The Construction of the Plasmid pB33-anti-RL and the Introduction of the Plasmid into the Genome of Potato Plants By means of the restriction endonuclease Asp718, a DNA fragment with an approximate length of 1800 bp, which comprises a part of the open reading frame of the cDNA insertion was isolated from the plasmid pRL1 and was ligated into the vector B33-Hyg which was cut with Asp718. This vector was constructed as follows:

The 35S promoter was removed from the pBinAR Hyg vector (DSM 9505) by means of the restriction endonucleases EcoR I and Asp718. A fragment with a length of about 1526 bp comprising the B33 promoter was isolated from the plasmid p33-anti-BE (DSM 6146) by means of EcoR I and Asp718 and inserted into the pBinAR Hyg vector (DSM 9505) cut with EcoR I and Asp718.

By inserting the cDNA fragment into the Asp718 site of the B33-Hyg plasmid, an expression cassette is produced which consists of the fragments A, B and C as follows (FIG. 4):

Fragment A contains the B33 promoter from *Solanum tuberosum* (EP 3775 092; Rocha-Sosa et al., EMBO J. 8 (1989), 23–29).

Apart from flanking regions, fragment B contains a part of the protein encoding region of the cDNA insertion from the pRL1 plasmid. This was isolated as an Asp718 fragment from pRL1 as described above and fused to the 35S promoter in antisense orientation.

Fragment C (192 bp) contains the polyadenylation signal of gene 3 of the T-DNA of the Ti-plasmid pTiACH5 (Gielen et al., EMBO J. 3 (1984), 835–846).

The plasmid pB33-anti-RL has a size of approximately 12.8 kb.

The plasmid was transferred into potato plants by means of *Agrobacteria*-mediated transformation, as described above. From the transformed cells whole plants were regenerated. The transformed plants were cultivated under greenhouse conditions. By analyzing total RNA in a Northern Blot analysis concerning the disappearance of the transcripts complementary to the cDNA the success of the genetic modification of the plants was assessed. For this purpose, total RNA was isolated from leaves of transformed plants according to standard methods and subsequently separated electrophoretically on an agarose gel. Then it was transferred onto a nylon membrane and hybridized with a radioactively labelled probe showing the sequence indicated under Seq ID No. 1 or a part thereof. In about 5–10% of the transformed plants the band indicating the transcript hybridizing with the cDNA of the invention was missing in the Northern Blot Analysis. From these plants starch was isolated from tubers and analyzed as described in Example 8.

EXAMPLE 8

Analysis of the Transformed Potato Plants

The potato plants transformed according to Example 6 and Example 7 were examined with regard to the properties of the synthesized starch. Analyses were carried out with various lines of the potato plants which had been transformed with the plasmid p35S-anti-RL or the plasmid pB33-anti-RL and which in Northern Blot analysis had not exhibited the band indicating transcripts hybridizing to the DNA sequences of the invention.

a) Determination of the Viscosity of Watery Solutions of the Starch

In order to determine the viscosity of the watery solutions of the starch synthesized in transformed potato plants, starch was isolated from tubers of plants which had been transformed with the plasmid p35S-anti-RL or the plasmid pB33-anti-RL using standard methods. 30 g of starch were each taken up in 450 ml $H_2O$ and used for analysis in an E viscograph (Brabender OHG Duisburg (Germany)). The appliance was used according to the manufacturer's instructions. In order to determine the viscosity of the watery solution of the starch, the starch suspension was first heated from 50° C. to 96° C. at a speed of 3° C. per minute. The temperature was subsequently kept at 96° C. for 30 min. The solution was then cooled from 96° C. to 50° C. at a speed of 3° C. per minute. During the whole process the viscosity was determined. Representative results of such measurements are set forth in the form of graphs in FIGS. 3, 4 and 5, in which the viscosity is shown depending on time. FIG. 3 shows a typical Brabender graph for starch isolated from wildtype-plants of the potatoe variety Désirée. FIGS. 4 and 5 show a typical Brabender graph for starch isolated from potato plants which had been transformed with the plasmid p35S-anti-RL or pB33-anti-RL. From these graphs characteristic values may be deduced.

The characteristic values for wildtype-plants are as follows:

TABLE 1

| Value | Time [min:sec] | Torque [BE] | Temperature [° C.] |
|---|---|---|---|
| A | 6:30 | 60.5 ± 17.7 | 69.9 ± 0.57 |
| B | 11:30 | 1838.0 ± 161.2 | 86.0 ± 2.1 |
| C | 15:15 | 1412.0 ± 18.4 | 96.0 |
| D | 45:15 | 526.0 ± 17.0 | 96.0 |
| E | 60:30 | 812.0 ± 8.5 | 50.0 |
| F | 70:45 | 853.0 ± 5.7 | 50.0 |

The values represent the average values obtained from two different measurements.

In Table 1 and the following Tables 2 and 3 the abbreviations signify the following:

| | |
|---|---|
| A: | start of pastification |
| B: | maximum viscosity |
| C: | start of 96° C.-period |
| D: | start of cooling-off time |
| E: | end of cooling-off time |
| F: | end of the end-50° C. period |

For plants which had been transformed with the plasmid p35S-anti-RL (line P2), the characteristic values are the following:

TABLE 2

| Value | Time [min:sec] | Torque [BE] | Temperature [° C.] |
|---|---|---|---|
| A | 6:00 | 50.0 | 69.0 |
| B | 14:00 | 820.0 | 93.0 |
| C | 15:15 | 815.0 | 96.0 |
| D | 45:15 | 680.0 | 96.0 |
| E | 60:30 | 1150.0 | 50.0 |
| F | 70:45 | 1200.0 | 50.0 |

For plants which had been transformed with the plasmid pB33-anti-RL (line P3), the characteristic values are the following:

TABLE 3

| Value | Time [min:sec] | Torque [BE] | Temperature [° C.] |
|---|---|---|---|
| A | 7:0 | 31.0 | 71.0 |
| B | 12:45 | 671.0 | 88.3 |
| C | 15:15 | 662.0 | 96.0 |
| D | 45:15 | 607.0 | 96.0 |
| E | 60:30 | 1063.0 | 50.0 |
| F | 70:45 | 1021.0 | 50.0 |

FIGS. 3, 4 and 5 explicitly show that the starch obtained from transformed plants differs from starch from wild-type plants particularly in that the viscosity increases only very slightly during heating. Thus, during heating the maximum viscosity of the modified starch from transformed plants is more than 50% lower than in the case of wildtype starch.

During cooling, on the other hand, the viscosity of the starch isolated from transformed plants increases more than in the case of wildtype-plants.

B) Determination of the Phosphate Content of the Starch

The phosphate content of the starch was determined by measuring the amount of phosphate bound to the C-6-position of the glucose residues. For this purpose, starch was first degraded by acid hydrolysis and the glucose-6-phosphate content was subsequently determined by means of an enzyme test, as described in the following.

100 mg starch were incubated in 500 µl 0.7 N HCl for 4 hours at 100° C. After acid hydrolysis 10 µl of the reaction were added to 600 µl imidazole buffer (100 mM imidazole, 5 mM $MgCl_2$, pH 6.9, 0.4 mM $NAD^+$). The amount of glucose-6-phosphate in the reaction mixture was determined by conversion with the enzyme glucose-6-phosphate-dehydrogenase. For this purpose, 1 U glucose-6-phosphate-dehydrogenase (from *Leuconostoc mesenteroides* (Boehringer Mannheim)) was added to the reaction mixture and the amount of produced NADH was determined by measuring the absorption at 340 nm.

The glucose-6-phosphate content of 1 mg starch is indicated in the following table for non-transformed potato plants of the variety Désirée as well as for two lines (P1 (35S-anti-RL); P2 (35S-anti-RL)) of transgenic potato plants which had been transformed with the plasmid p35S-anti-RL.

TABLE 4

| Plants | nmol glucose-6-phosphate/mg starch | % |
|---|---|---|
| Wildtype | 12.89 ± 1.34 | 100 |
| P1 (35S-anti-RL) | 2.25 ± 0.41 | 17.4 |
| P2 (35S-anti-RL) | 1.25 ± 0 | 9.7 |

The following table shows the glucose-6-phosphate content per milligram starch in potato plants which were transformed with the plasmid pB33-anti-RL, compared to starch from non-transformed plants (*S. tuberosum* c.v. Désirée).

TABLE 5

| Plants | nmol glucose-6-phosphate/mg starch | % |
|---|---|---|
| Wildtype | 9.80 ± 0.68 | 100 |
| 7 | 4.50 ± 0.73 | 45.9 |
| 37 | 2.64 ± 0.99 | 26.9 |
| 45 | 1.14 ± 0.44 | 11.6 |
| 31 | 1.25 ± 0.49 | 12.8 |

The plants 7, 37, 45 and 31 represent independent transformants which had been transformed with the plasmid pB33-anti-RL. Plant 37 represents line P3 for which a Brabender graph is plotted in FIG. 5.

The values show that the phosphate content of the modified starch from transgenic potato plants is at least 50% lower when compared to starch from wildtype plants.

C) Determination of Glucose, Fructose and Sucrose Content of Tubers after Storage at 4° C.

Tubers of plants from various transgenic lines which had been transformed with the antisense-construct p35S-anti-RL as well as tubers of wildtype plants were stored at 4° C. or, respectively, at 20° C. in darkness, for two months. Subsequently, the amounts of glucose, fructose and sucrose were determined. For two transgenic lines the representative values obtained were the following:

TABLE 6

| | Glucose | | Fructose | | Sucrose | |
|---|---|---|---|---|---|---|
| | 20° C. | 4° C. | 20° C. | 4° C. | 20° C. | 4° C. |
| Wildtype cv Désirée | 0.84 | 55.4 | 0.62 | 52.8 | 8.5 | 13.1 |
| Transgenic line 15 | 1.12 | 6.7 | 0.75 | 7.8 | 7.5 | 10.1 |
| Transgenic line 11 | 1.00 | 6.4 | 0.75 | 7.5 | 6.9 | 6.9 |

The values in the table are indicated in µmol hexose or sucrose/g fresh weight.

From the values of Table 6 it becomes obvious that the accumulation of reducing sugars in the tubers is considerably lower in transgenic plants stored at 4° C. than in wildtype plants.

Altogether the modified starch isolated from transgenic potato plants resembles starch from maize-wildtype plants. However, in comparison it has the advantage that its taste is neutral and that it is therefore more suitable for various uses in the foodstuffs area.

EXAMPLE 9

Expression of the cDNA Insertion of the pRL2 Plasmid in *E. coli*

(a) Transformation of Bacterial Cells

In order to express the cDNA insertion of the plasmid pRL2 the cells of the *E. coli* strain DH5α are first transformed with the pACAC plasmid. This plasmid contains a DNA fragment encoding the ADP-glucose-pyrophosphorylase (AGPase) from *E. coli*, under the control of the lac Z promoter. The fragment had been isolated from the vector pEcA-15 as a DraI/HaeII fragment with a size of about 1.7 kb (see B. Müller-Röber (1992), dissertation, FU Berlin) and after filling in its sticky ends it had been cloned into a pACAC184 vector linearized with HindIII. The expression of AGPase is to cause an increase of the glycogen synthesis in transformed *E. coli* cells. The cells transformed in such a way will in the following be named *E. coli*-K1-cells.

In order to determine the enzyme activity of the protein encoded by the cDNA of plasmid pRL2, *E. coli*-K1-cells were transformed with the pRL2 plasmid. The transformed *E. coli* cells which contain the pACAC plasmid as well as the pRL2 plasmid will in the following be named *E. coli*-K2-cells. The transfer of the plasmid DNA into the bacterial cells was carried out according to the Hanahan method (J. Mol. Biol. 166 (1983), 557–580). The transformed *E. coli* cells were plated onto agar culture dishes with the following composition:

YT medium containing
1,5% Bacto agar
50 mM sodium phosphate buffer, pH 7.2
1% glucose
10 μg/ml chloramphenicol in the case of *E. coli*-K1-cells
or
10 μg/ml chloramphenicol and
10 μg/ml ampicillin in the case of *E. coli*-K2-cells.

*Escherichia coli* cells of the DH5α strain which had been transformed with the plasmid pRL2+pACAC (*E. coli*-K2-cells) and also—for control—solely with the pACAC plasmid (*E. coli*-K1-cells), were raised on agar plates. The formed glycogen of the various cultures was examined with respect to the degree of phosphorylization (at the C-6 position of the glucose molecule), as described in the following.

(b) Isolation of Bacterial Glycogen

In order to isolate bacterial glycogen, the bacteria colony which had grown after transformation was floated from each 6 agar plates (Ø135 mm) with 5 ml YT medium for each plate. The bacterial suspension was centrifuged at 4500×g for 5 minutes. The bacterial precipitate was resuspended in 10 ml YT medium. Disruption of the bacteria was carried out by adding 2 volumes of disruption medium (0.2 N NaOH; 1% SDS) and by incubation at room temperature for 5 minutes. By adding 3 volumes of EtOH abs., incubating at 4° C. for 30 minutes and subsequent centrifuging at 8000 gx for 15 minutes, the glycogen was sedimented. Then the precipitate was washed with 100 ml of 70% EtOH and again sedimented by means of a centrifugation step (10 minutes at 8000×g). The washing procedure was repeated four times.

(c) Determination of the Total Glycogen Content

The isolated and sedimented glycogen was first degraded into single glucose molecules by means of acidic hydrolysis (dissolving of the precipitate in 2 ml 0.7 N HCl; incubation for 4 hours at 100° C.). The glucose content of the solution was determined by means of coupled enzymatic reaction of a starch test with a photometer (Kontron) at a wave length of 340 nm according to the manufacturer's (Boehringer Mannheim) instructions.

The reaction buffer contains:
100 mM MOPS, pH 7.5
10 mM $MgCl_2$
2 mM EDTA
0.25 mM NADP
1 mM ATP
1 U/ml glucose-6-phosphate-dehydrogenase
2 U/ml hexokinase Die measurement was carried out at 25° C. with 10 μl glucose solution.

(d) Determination of the Glucose-6-Phosphate Content

In order to determine the content of glucose molecules phosphorylated at the C-6 position, equal amounts of glucose of the various bacterial cultures were used. By adding the same volumes of 0.7 N KOH to the glycogens degraded into its glucose molecules by acidic hydrolysis (as above), the solution was neutralized.

The reaction buffer contains:
100 mM MOPS, pH 7.5
10 mM $MgCl_2$
2 mM EDTA
0.25 mM NADP
2 U/ml glucose-6-phosphate-dehydrogenase The measurement was carried out at 25° C. with 100 to 150 μl glucose solution.

(e) Identification of an Enzyme Activity Phosphorylating Bacterial Glycogen

The results of the determination of the phosphate content of the glycogen synthesized in the bacterial cells show that the glycogen of *E. coli* cells, which had been transformed with the pACAC+pRL2 plasmids, exhibits a 290 ±25% increased phosphorylation at the C-6 position of the glucose when comparing with the control reaction (*E. coli* cells transformed with the pACYC) (see the following table).

*E. coli* cells glucose-6-phosphase: glucose in glycogen
*E. coli*-K1 1:(4600±1150)
*E. coli*-K2 1:(1570±390)

The degrees of phosphorylation indicated herein are the average value of at least 6 measurements starting from 6 independent transformations and glycogen isolations.

EXAMPLE 10

Integration of the Plasmid p35S-anti-RL in Combination with the Plasmid p35SH-anti-BE into the Genome of Potato Plants The plasmid p35S-anti-RL was constructed as described in Example 6. The plasmid p35SH-anti-BE was constructed as described in the application WO95/07355, Example 3. Both plasmids were sequentially transferred into potato plants by means of the *Agrobacterium* mediated transformation as described above. For this purpose, the plasmid p35SH-anti-BE was first transformed in potato plants.

Whole plants were regenerated and selected for a reduced expression of the branching enzyme gene. Subsequently, the plasmid p35S-anti-RL was transformed into the transgenic plants already showing a reduced expression of the branching enzyme. From the transformed cells transgenic plants were again regenerated and the transformed plants were cultivated under greenhouse conditions. By analyzing total RNA in an RNA Blot analysis with respect to the disappearance of the transcripts complementary to the branching enzyme cDNA or the RL cDNA, the success of the genetic modification of the plants with respect to a highly reduced expression of the branching enzyme gene as well as with respect to a highly reduced expression of the RL gene was assessed. For this purpose, total RNA was isolated from leaves of transformed plants according to the described methods and subsequently separated by means of gel electrophoresis, transferred onto a membrane, hybridized with a radioactively labelled probe showing the sequence indicated under Seq ID No. 1 or a part thereof and then hybridized with a radioactively labelled probe showing the sequence of the branching enzyme cDNA (cf. WO92/14827, Example 1) or a part thereof. In about 5–10% of the transformed plants the band indicating the specific transcript of the sequence indicated under Seq ID No. 1 as well as the band indicating the specific transcript of the branching enzyme cDNA (cf. WO92/14827) was missing in the RNA Blot Analysis. These plants, which were designated R4 plants were used for analyzing the quality of the starch contained in tubers.

EXAMPLE 11

Integration of the Plasmid pB33-anti-RL in Combination with the Plasmid pB33-anti-GBSSI into the Genome of Potato Plants The plasmid pB33-anti-RL was constructed as described in Example 7. The plasmid pB33-anti-GBSSI was constructed as follows:

The DraI/DraI fragment of the promoter region of the patatin class I gene B33 from *Solanum tuberosum* comprising the nucleotides −1512 to +14 (Rocha-Sosa et al., EMBO J 8 (1989), 23–29) was ligated into the SmaI site of the pUC19 plasmid. From the resulting plasmid the promoter fragment was ligated into the polylinker region of the pBin19 plasmid (Bevan, Nucleic Acids Research 12 (1984), 8711–8721) as an EcoRI/HindIII fragment. Subsequently, the 3' EcoRI fragment 1181 to 2511 of the GBSSI gene of *Solanum tuberosum* (Hegersberg, dissertation (1988), University of Cologne) was ligated into the EcoRI site of the resulting plasmid.

Both plasmids were transferred sequentially into potato plants by means of *Agrobacterium* mediated transformation as described in Example 10. From the transformed cells plants were regenerated and the transformed plants were cultivated under greenhouse conditions. By analyzing the complete RNA in a RNA Blot analysis with regard to the disappearance of the transcripts complementary to the two cDNAs, the success of the genetic modification of the plants was assessed. For this purpose, total RNA was isolated from tubers of transformed plants according to standard methods and subsequently separated on agarose gel by means of gel electrophoresis, transferred onto a membrane and hybridized with a radioactively labelled probe showing the sequence indicated under Seq ID No. 1 or a part thereof. Afterwards, the same membrane was hybridized with a radioactively labelled probe having the sequence of the GBSSI gene or a part of this sequence (Hegersberg, dissertation (1988) University of Cologne). In about 5–10% of the transformed plants the band indicating the transcripts hybridizing to the cDNA of the invention or the GBSSI cDNA were missing in the RNA Blot Analysis. From the tubers of these plants, which were designated R3 plants, starch was isolated and analyzed.

EXAMPLE 12

Starch Analysis of R4 Plants

The potato plants transformed according to Example 10 were examined with respect to the properties of the synthesized starch. The analyses were carried out with various lines of the potato plants which had been transformed with the plasmids p35S-anti-RL and p35SH-anti-BE and which did no longer—or only in extremely reduced form—show the bands indicating transcripts hybridizing to the DNA sequences of the invention or to the sequences of the branching cDNA in RNA Blot analysis.

A) Determination of the Viscosity of Watery Solutions of the Starch

In order to determine the viscosity of the watery solutions of the starch synthesized in transformed potato plants, starch was isolated from tubers of plants which had been transformed with the plasmid p35S-anti-RL and the plasmid p35SH-anti-BE. 2 g of starch were each dissolved in 25 ml $H_2O$ and used for analysis with a Rapid Visco Analyser (Newport Scientific Pty Ltd, Investment Support Group, Warriewood NSW 2102, Australia). The equipment was used according to the instructions of the manufacturer. In order to determine the viscosity of the watery solution of the starch, the starch suspension was first heated from 50° C. to 95° C. with a speed of 12° C. per minute. The temperature was then kept at 95° C. for 2.5 minutes. Afterwards, the solution was cooled from 95° C. to 50° C. with a speed of 12° C. per minute. During the whole process the viscosity was measured. Representative results of such measurements are set forth in the form of graphs in which the viscosity is shown depending on time. FIG. 6 shows a typical RVA graph for starch isolated from the wildtype-plants of potato of the variety Désirée. Lines 2 and 3 show a typical RVA graph for starch isolated from the tubers of plants which had been transformed with the plasmid p35SH-anti-BE and with the plasmid p35S-anti-RL, respectively. Line 4 shows a typical RVA graph for starch isolated from tubers of plants which had been transformed with plasmid p35SH-anti-BE in combination with plasmid p35S-anti-RL. Line 4 is characterized in that there is no temperature-dependent increase of viscosity.

B) Determination of the Amylose/Amylopectin Ratio

Starch which was isolated from the tubers of transformed potato plants was examined with respect to the ratio of amylose to amylopectin. The plant line R4-1 (shown in line 4 of FIG. 6) exhibited an amylose content of more than 70%. For the plant line R4-3 an amylose value of 27% was measured, whereas the amylose content in wildtype starch of the Désirée variety rates between 19 and 22%.

EXAMPLE 13

Starch Analysis of R3 Plants

The potato plants transformed according to Example 11 were examined with respect to the properties of the synthesized starch. The analyses were carried out with various lines of the potato plants which had been transformed with the plasmids pB33-anti-RL and pB33-anti-GBSSI and which did no longer—or only in extremely reduced form—show the bands indicating transcripts hybridizing to the DNA sequences of the invention or to the sequences of the GBSSI cDNA in RNA Blot analysis.

A) Determination of the Viscosity of Watery Solutions of the Starch

In order to determine the viscosity of the watery solution of the starch synthesized in transformed potato plants, starch was isolated from tubers of plants which had been transformed with the plasmid pB33-anti-RL in combination with the plasmid pB33-anti-GBSSI. The viscosity was determined by means of a Rapid Visco Analyser according to the method described in Example 12, part a. The results are indicated in FIG. 7. In line 1, FIG. 7 shows a typical RVA graph for starch isolated from the wildtype-plants of the Désirée potato variety. Lines 2 and 3 show typical RVA graphs for starches isolated from potato plants which had been transformed with the plasmid pB33-anti-GBSSI and with the plasmid p35S-anti-RL, respectively. Line 4 shows a typical RVA graph for starch isolated from potato plants which had been transformed with the plasmid pB33-anti-GBSSI in combination with the plasmid pB33-anti-RL. This graph is characterized in that the maximum viscosity and the increase of viscosity at 50° C. are missing. Furthermore, this starch is characterized in that the glue obtained after RVA treatment exhibits almost no retrogradation after incubating at room temperature for several days.

B) Determination of the Amylose/Amylopectin Ratio

Starch which was isolated from the tubers of transformed potato plants was examined with respect to the ratio of amylose to amylopectin. The plant line R3-5 (shown in line 4 of FIG. 7) exhibited an amylose content of less than 4%. For the plant line R3-6 an amylose content of less than 3% was measured. The amylose content in wildtype starch of the Désirée variety rates between 19 and 22%.

C) Determination of the Phosphate Content of Starch

The phosphate content of the starch was determined by measuring the amount of phosphate bound to the C-6-position of the glucose residues. For this purpose, starch was first degraded by acid hydrolysis and the glucose-6-phosphate content was subsequently determined by means of an enzyme test, as described in the following.

100 mg starch were incubated in 500 µl 0.7 N HCl for 4 hours at 100° C. After acid hydrolysis 10 µl of the reaction mixture were added to 600 µl imidazole buffer (100 mM imidazole, 5 mM $MgCl_2$, pH 6.9, 0.4 mM $NAD^+$). The amount of glucose-6-phosphate in the preparation is determined by conversion with the enzyme glucose-6-phosphate-dehydrogenase. For this purpose, 1 U glucose-6-phosphate-dehydrogenase (from *Leuconostoc mesenteroides* (Boehringer Mannheim)) was added to the reaction mixture and the amount of produced NADH was determined by measuring the absorption at 340 nm.

The glucose-6-phosphate content of 1 mg starch is indicated in the following table for non-transformed potato plants of the variety Désirée as well as for the R3-5 and the R3-6 line of transgenic potato plants which had been transformed with the plasmid pB33-anti-RL in combination with the plasmid pB33-anti-GBSSI. As a comparison, the value of the starch from the so-called waxy potato (US2-10) which had been transformed with the plasmid pB33-anti-GBSSI, is also indicated.

TABLE 7

| Plants | nmol glucose-6-phosphate/mg starch | % |
|---|---|---|
| Wildtype | 9.80 ± 0.68 | 100 |
| R3-5 | 1.32 ± 0.10 | 13 |
| R3-6 | 1.37 ± 0.15 | 14 |
| US2-10 | 10.82 ± 0.42 | 110 |

EXAMPLE 14

Isolation of a cDNA Sequence Encoding an R1 Enzyme from *Zea mays*

Bacteria of the XL1-Blue strain were infected with lambda phages, the phage heads of which contained a cDNA library of endosperm tissue from *Zea mays* (Stratagene, Heidelberg). The infected *E. coli* cells were plated on a medium in Petri dishes with a density of about 25000 plaques per approx. 75 $cm^2$. After about 9 hours of incubation nitro cellulose filters were laid on the lysed bacteria and were removed after one minute. The filter was first incubated in 0.5 M NaOH, 1.5 M NaCl for two minutes, then in 0.5 M Tris HCl pH 7.0 for two minutes and subsequently washed in 2×SSC for two minutes. After drying and fixing by UV crosslinking the filters were incubated in buffer A for 3 hours before a radioactively labelled DNA probe (random priming) was added. A fragment of the pRL2 plasmid DNA insertion (see Examples 4 and 5) with a size of approximately 2.7 was used as a probe. This fragment was cut with the restriction enzymes XhoI and HindIII and represented the 3' end of the cDNA insertion in pRL2 (see FIG. 8).

After hybridizing for 12 hours at 48° C. the filters were washed for 1×10 minutes in 2×SSC/1% SDS at room temperature and then 2×20 minutes in 1×SSC/0.5% SDS at 35° C. and subsequently autoradiographed.

Phage clones comprising a cDNA insertion were singled out in three screening cycles. Thereby, when screening about 1,500,000 phage plaques approximately 6 plaques were identified.

These positive phage clones were used for the in vivo excision of a pBluescript plasmid according to standard methods. The DNA sequences of the corresponding insertions were determined according to the method of Sanger et al. (Proc. Natl. Acad. Sci. USA 74 (1977), 5463–5467). Thus, a number of clones could be identified containing insertions encoding an R1 enzyme from maize. The cDNA insertion of a suitable clone, R1M, was completely determined. The nucleic acid sequence is indicated in Seq ID No. 5. The amino acid sequence derived therefrom is indicated in Seq ID No. 6.

A suitable cDNA insertion of the R1M clone was isolated from the pBluescript derivative by NotI and XhoI by means of standard methods (Sambrook et al., Molecular Cloning: A Laboratory Manual, $2^{nd}$ edition, Cold Spring Harbour Laboratory Press, (1989), NY, USA). The sticky ends were filled in and the fragment was inserted into the pUBIbar vector at the HpaI site. This plasmid may be used for transforming plant cells, particularly maize, according to the methods described above. Since the sequence depicted in Seq ID No. 5 represents only a partial cDNA sequence, further techniques were applied to isolate sequences representing the 5' end of the cDNA. For this purpose polyA+ RNA was isolated from leaf tissue of maize according to standard methods. The isolated RNA was used for a polymerase chain reaction using the Titan™ One Tube RT-PCR system (Boehringer Mannheim, Germany) according to the instructions of the manufacturer. In this reaction the RNA is transcribed in a first step into cDNA which is then used as a template for the PCR. As primers the following oligonuleotides were used:

Primer 1 (Seq ID No. 9):

5' GCAAAGTTTT CAAGGACAAG ACTGATGAAG 3'

Primer 2 (Seq ID No. 10):

5' CCAGATGGCA CGACAGTGTA CAAGAACA 3' and

Primer 6 (Seq ID No. 11):

5' AATGACTGCA AAGGIGGIAT GATGGA 3'

The combination of primers 1 and 6 led to a 560 bp fragment. The primer combination 1 and 2 led to a PCR fragment of 2289 bp. Both fragments were sequenced. The obtained sequence represents most of the 5' end of the cDNA. The complete sequence of the partial cDNA clone and the sequences obtained by PCR as described above is depicted in Seq ID No. 7. The derived amino acid sequence is depicted in Seq ID No. 8. Comparison with the full-length cDNA of potato revealed that the obtained sequence is probably not yet complete and that about 420 bp of the 5'end are missing. This missing sequence can be completed by methods well known to the person skilled in the art. It is, for example, possible to isolate the 5'end of the cDNA using the 5'-RACE method (rapid amplification of cDNA ends). With this method an unknown 5'-end of a cDNA can be amplified by PCR. This method is normally used to produce cDNA which, in comparison to a known cDNA, is extended at the 5'-end. In order to apply the 5'-RACE method one can use, e.g., the Marathon-cDNA amplification kit (Clontech).

Other possibilities to isolate the complete cDNA are further PCRs using, for example, a lambda ZAP cDNA library of maize (Stratagene), immuno screening of expression libraries or the use of standard hybridization methods.

The invention claimed is:

1. An isolated nucleic acid molecule comprising regulatory elements operably linked to a nucleic acid sequence selected from the group consisting of:
   (a) nucleotides 33–1943 of SEQ ID NO: 5 or nucleotides 2–4009 of SEQ ID NO: 7; or
   (b) a nucleic acid sequence that has more than 95% overall sequence identity to a nucleic acid sequence of (a); and
   (c) a fragment of a nucleic acid sequence of (a) or (b), wherein the fragment is of sufficient length to mediate a cosuppression effect in a maize plant cell;
   wherein a maize plant cell comprising said nucleic acid molecule produces starch with reduced phosphate content compared to starch from a non-transformed maize plant cell.

2. The nucleic acid molecule of claim 1, wherein the nucleic acid sequence is nucleotides 33–1943 of SEQ ID NO: 5 or nucleotides 2–4009 of SEQ ID NO: 7.

3. The nucleic acid molecule of claim 1, wherein the nucleic acid sequence is a fragment of a nucleic acid sequence represented by nucleotides 33–1943 of SEQ ID NO: 5 or nucleotides 2–4009 of SEQ ID NO: 7, wherein the fragment is of sufficient length to mediate a cosuppression effect in a maize plant cell.

4. The nucleic acid molecule of claim 1, wherein the nucleic acid sequence is a nucleic acid sequence that has more than 95% overall sequence identity to a sequence represented by nucleotides 33–1943 of SEQ ID NO: 5 or nucleotides 2–4009 of SEQ ID NO: 7.

5. The nucleic acid molecule of claim 1, wherein the nucleic acid sequence is a fragment of a nucleic acid sequence that has more than 95% overall sequence identity to a sequence represented by nucleotides 33–1943 of SEQ ID NO: 5 or nucleotides 2–4009 of SEQ ID NO: 7, wherein the fragment is of sufficient length to mediate a cosuppression effect in a maize plant cell.

6. A vector comprising the nucleic acid molecule of claim 1.

7. A cell, which is genetically modified with the nucleic acid molecule of claim 1 or with a vector comprising said nucleic acid molecule.

8. The cell of claim 7, which is a transgenic maize plant cell.

9. A maize plant comprising the cell of claim 8.

10. A process for the production of a modified starch comprising the step of extracting the starch from a maize plant comprising the cell of claim 8 and/or from starch storing parts of said maize plant.

11. The cell of claim 8, in which the activity of at least one further enzyme involved in starch biosynthesis or starch modification is reduced at least 30% when compared to non-transformed plants.

12. The cell of claim 11 in which the activity of a branching enzyme is reduced.

13. The cell of claim 8 in which the activity of a starch granule-bound starch synthase of isotype I (GBSS I) is reduced.

14. A method for producing a transgenic maize plant cell that synthesizes a modified starch comprising the steps of
 (a) genetically modifying a maize plant cell to express a nucleic acid molecule that comprises a nucleic acid sequence selected from the group consisting of:
  (i) nucleotides 33–1943 of SEQ ID NO: 5 or nucleotides 2–4009 of SEQ ID NO: 7; or
  (ii) a nucleic acid sequence that has more than 95% overall sequence identity to a nucleic acid sequence of (i); and
  (iii) a fragment of a nucleic acid sequence of (i) or (ii), wherein the fragment is of sufficient length to mediate a cosuppression effect in a maize plant cell;
 and wherein said expressing leads to the maize plant cell producing starch with reduced phosphate content compared to starch from a non-transformed maize plant cell, and
 (b) isolating the maize plant cell expressing said nucleic acid molecule;
 thereby producing the maize plant cell synthesizing a modified starch.

15. The method according to claim 14, wherein the enzyme activity of at least one additional enzyme involved in starch biosynthesis and/or starch modification is reduced at least 30% when compared to non-transformed maize plants.

16. The method of claim 15 wherein the additional enzyme is a branching enzyme.

17. The method of claim 15 wherein the additional enzyme is a starch granule-bound starch synthase of isotype I (GBSS I).

18. A maize plant cell produced by the method of claim 14.

19. A transgenic maize plant comprising the maize plant cell of claim 18.

20. Propagation material of a plant, wherein the propagation material comprises the cell according to claim 8.

21. A process for the production of a modified starch comprising the step of extracting the starch from the plant of claim 19 and/or from a starch-storing part of said plant.

22. Propagation material of a plant, wherein the propagation material comprises the plant cell of claim 18.

23. A seed of the maize plant of claim 19.

* * * * *